United States Patent
Cua et al.

(10) Patent No.: US 11,697,681 B2
(45) Date of Patent: *Jul. 11, 2023

(54) ANTI-ANNEXIN A2 MONOCLONAL ANTIBODIES

(71) Applicant: AGENCY FOR SCIENCE, TECHNOLOGY AND RESEARCH, Singapore (SG)

(72) Inventors: Simeon Cua, Singapore (SG); Andre Boon Hwa Choo, Singapore (SG); Heng Liang Tan, Singapore (SG); Wey Jia Fong, Singapore (SG); Vanessa Mei Yee Ding, Singapore (SG); Leonard Wen Yan Leong, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 435 days.

This patent is subject to a terminal disclaimer.

(21) Appl. No.: 16/848,828

(22) Filed: Apr. 14, 2020

(65) Prior Publication Data

US 2020/0399353 A1 Dec. 24, 2020

Related U.S. Application Data

(63) Continuation of application No. 16/321,020, filed as application No. PCT/SG2017/050382 on Jul. 26, 2017, now Pat. No. 10,654,921.

(30) Foreign Application Priority Data

Jul. 26, 2016 (SG) .......................... 10201606178X

(51) Int. Cl.
*A61K 39/395* (2006.01)
*C07K 16/18* (2006.01)
(Continued)

(52) U.S. Cl.
CPC ............ *C07K 16/18* (2013.01); *A61K 31/282* (2013.01); *A61K 31/337* (2013.01); *A61K 31/5377* (2013.01); *A61K 38/1774* (2013.01); *A61K 39/3955* (2013.01); *A61K 47/6819* (2017.08); *A61K 47/6825* (2017.08); *A61K 47/6843* (2017.08); *A61P 35/00* (2018.01); *C07K 14/70521* (2013.01); *G01N 33/574* (2013.01); *A61K 2039/505* (2013.01); *A61K 2039/572* (2013.01); *C07K 2317/24* (2013.01); *C07K 2317/34* (2013.01); *C07K 2317/40* (2013.01); *C07K 2317/54* (2013.01); *C07K 2317/565* (2013.01); *C07K 2317/622* (2013.01); *C07K 2317/73* (2013.01); *C07K 2317/732* (2013.01); *C07K 2317/734* (2013.01); *C07K 2317/77* (2013.01); *C07K 2317/90* (2013.01); *C07K 2319/03* (2013.01); *C07K 2319/30* (2013.01); *C07K 2319/33* (2013.01); *G01N 2333/4718* (2013.01)

(58) Field of Classification Search
None
See application file for complete search history.

(56) References Cited

U.S. PATENT DOCUMENTS

2015/0105322 A1   4/2015  Wang

FOREIGN PATENT DOCUMENTS

| WO | 0029004 A1 | 5/2000 |
| WO | 2006129729 A1 | 7/2006 |
| WO | 2008/076454 A1 | 6/2008 |

OTHER PUBLICATIONS

Martin et al (Journal of the National Cancer Institute, vol. 92, No. 14: pp. 1126-1135, Jul. 19, 2000) (Year: 2000).*
Apantaku et al. (Breast cancer diagnosis and screening, American Family Physician 2000) (Year: 2000).*
Rudikoff et al. (Proc Natl Acad Sci USA 1982 vol. 79 p. 1979). (Year: 1979).*

(Continued)

Primary Examiner — Meera Natarajan
(74) Attorney, Agent, or Firm — Womble Bond Dickinson (US) LLP

(57) ABSTRACT

The present invention relates to an antigen-binding protein, or an antigen-binding fragment thereof, comprising (i) a heavy chain variable domain comprising a VHCDR1 having the amino acid sequence GYSITSGYSWH; a VHCDR2 having the amino acid sequence YIHYSGSTKYNPSLKS and a VHCDR3 having the amino acid sequence GSNYGFDY; and (ii) a light chain variable domain comprising a VLCDR1 having the amino acid sequence KSSQSLLYSNDQKNYLA, a VLCDR2 having the amino acid sequence WASIRES, and a VLCDR3 having the amino acid sequence QQYYIYPLT. The present invention also relates to an antigen-binding protein, or an antigen-binding fragment thereof, comprising (i) a heavy chain variable domain comprising a VHCDR1 having the amino acid sequence VYSITSGYSWH; a VHCDR2 having the amino acid sequence YIHYSGSTKYNPSLKS, and a VHCDR3 having the amino acid sequence GTDNAVDY; and (ii) a light chain variable domain comprising a VLCDR1 having the amino acid sequence KSSQSLLYSSNQKNYLA, a VLCDR2 having the amino acid sequence WAS SRES, and a VLCDR3 having the amino acid sequence QQYYIYPLT. Compositions comprising the antigen-binding protein, or antigen-binding fragment thereof, methods of use of the antigen-binding protein, or antigen-binding fragment thereof and kits comprising the antigen-binding protein, or antigen-binding fragment thereof are also provided.

17 Claims, 38 Drawing Sheets

Specification includes a Sequence Listing.

(51) Int. Cl.

| A61K 47/68 | (2017.01) |
| A61P 35/00 | (2006.01) |
| G01N 33/574 | (2006.01) |
| A61K 31/282 | (2006.01) |
| A61K 31/337 | (2006.01) |
| A61K 31/5377 | (2006.01) |
| A61K 38/17 | (2006.01) |
| C07K 14/705 | (2006.01) |
| A61K 39/00 | (2006.01) |

(56) References Cited

OTHER PUBLICATIONS

MacCallum et al. J. Mol. Biol. (1996) 262, 732-745 (Year: 1996).*
Pascalis et al. (The Journal of Immunology (2002) 169, 3076-3084) (Year: 2002).*
Casset et al. (BBRC 2003, 307:198-205) (Year: 2003).*
Vajdos et al. (J. Mol. Biol. (2002) 320, 415-428) (Year: 2002).*
Chen et al. (J. Mol. Bio. (1999) 293, 865-881) (Year: 1999).*
Wu et al. (J. Mol. Biol. (1999) 294, 151-162) (Year: 1999).*
Padlan et al. (PNAS 1989, 86:5938-5942) (Year: 1989).*
Lamminmaki et al. (JBC 2001, 276:36687-36694) (Year: 2001).*
Ausubel, et al., "Current Protocols in Molecular Biology," Dec. 4, 2003, 4648 pgs., John Wiley & Sons, Inc.
Chao, et al., "Dendritic cells respond to nasopharygeal carcinoma cells through annexin A2-recognizing DC-SIGN," Oncotarget, Nov. 6, 2014, pp. 159-170, vol. 6, No. 1.
Chaudhary, et al., "Inhibition of triple-negative and Herceptin-resistant breast cancer cell proliferation and migration by Annexin A2 antibodies," British Journal of Cancer, Oct. 2014, pp. 2328-2341, vol. 111, Cancer Research UK.
Choo, et al., "Selection Against Undifferentiated Human Embryonic Stem Cells by a Cytotoxic Antibody Recognizing Podocalyxin-Like Protein-1," Stem Cells, 2008, pp. 1454-1463, vol. 26.
Cibiel, et al., "From Ugly Duckling to Swan: Unexpected Identification from Cell-SELEX of an Anti-Annexin A2 Aptamer Targeting Tumors," PLoS One, Jan. 2014, 11 pgs., vol. 9, No. 1.
Cua, et al., "Targeting of embryonic annexin A2 expressed on ovarian and breast cancer by the novel monoclonal antibody 2448," Oncotarget, 2018, pp. 13206-13221, vol. 9, No. 2017.
The extended European search report for European Application No. 17834875 dated Feb. 27, 2020, 40 pages.
Gopalakrishnapillai, et al., "Disruption of Annexin II/p11 Interaction Suppresses Leukemia Cell Binding, Homing and Engraftment, and Sensitized the Leukemia Cells to Chemotherapy," Oct. 14, 2015, 18 pgs. , vol. 10, No. 10.
Green, et al., "Molecular Cloning, A Laboratory Manual," 2012, 34 pgs., Fourth Edition, Cold Spring Harbor Laboratory Press, Cold Spring Harbor, New York.
Ho, et al., "IRES-mediated Tricistronic vectors for enhancing generation of high monoclonal antibody expressing CHO cell lines," Journal of Biotechnology, 2012, pp. 130-139, vol. 157, Elsevier.
Holliger, et al., "Engineered antibody fragments and the rise of single domains," Nature Biotechnology, Sep. 2005, pp. 1126-1136, vol. 23, Nature Publishing Group.
Ji, et al., "Evaluation of annexin II as a potential serum marker for hepatocellular carcinoma using a developed sandwich ELISA method," International Journal of Molecular Medicine, 2009, pp. 765-771, vol. 24.
Kesavan, et al., "Annexin A2 Is a Molecular Target for TM601, a Peptide with Tumor-targeting and Anti-angiogenic Effects," The Journal of Biological Chemistry, Feb. 12, 2010, pp. 4366-4374, vol. 285, No. 7, The American Society for Biochemistry and Molecular Biology, Inc., USA.
Lokman, et al., "Annexin A2 is regulated by ovarian cancer-peritoneal cell interactions and promotes metastasis," Oncotarget, Aug. 2013, pp. 119-1211, vol. 4, No. 8.
Mukerjee, et al., "Targeted Nanocurcumin Therapy Using Annexin A2 Antibody Improves Tumor Accumulation and Therapeutic Efficacy Against Highly Metastatic Breast Cancer," Journal of Biomedical Nanotechnology, 2016, pp. 1374-1392, vol. 12, American Scientific Publishers.
Sharma, et al., "Angiogenesis-associated protein annexin II in breast cancer: Selective expression in invasive breast cancer and contribution to tumor invasion and progression," Experimental and Molecular Pathology, Apr. 27, 2006, pp. 146-156, vol. 81, Elsevier.
Sharma, et al., "Antibody-directed targeting of angiostatin's receptor annexin II inhibits Lewis Lung Carcinoma tumor growth via blocking of plasminogen activation: Possible biomedical mechanism of angiostatin's action," Experimental and Molecular Pathology, 2006, pp. 136-145, vol. 81, Elsevier.
Sharma, et al., "Antibody-directed neutralization of annexin Ii (ANX II) inhibits neoangiogenesis and human breast tumor growth in a xenograft model," Experimental and Molecular Pathology, 2012, pp. 175-184, vol. 92, Elsevier.
Shetty, et al., "Cell surface interaction of annexin A2 and galectin-3 modulates epidermal growth factor receptor signaling in Her-2 negative breast cancer cells," Molecular Cellular Biochemistry, 2016, pp. 221-233, vol. 411.
The International Preliminary Report on Patentability for PCT Application No. PCT/SG2017/050382 dated Jan. 29, 2019, 7 pages.
The International Search Report for PCT Application No. PCT/SG2017/050382 dated Sep. 25, 2017, 3 pages.
The first Written opinion for Singaporean Application No. 11201900703T dated Mar. 9, 2020, 9 pages.
The Written Opinion for PCT Application No. PCT/SG2017/050382 dated Sep. 25, 2017, 6 pages.
Tuszynski, et al., "Angiostatin Binds to Tyrosine Kinase Substrate Annexin II through the Lysine-Binding Domain in Endothelial Cells," Microvascular Research, 2002, pp. 448-432, vol. 64, Elsevier Science, USA.
Zheng, et al., "Tyrosine 23 Phosphorylation-Dependent Cell-Surface Localization of Annexin A2 Is Required for Invasion and Metastases of Pancreatic Cancer," PLos One, 2011, 14 pgs., vol. 6, No. 4.

* cited by examiner

Fig. 1A
C51 Gene Sequence (Heavy Chain) (SEQ ID NO.: 7)
CAGGTGAAACTGCAGGAGTCAGGACCTGACCAGGTGAAACCCTCTCAGTCACTTT
CACTCACCTGCACTGTCACTGTCTACTCCATCACCAGTGGTTATAGCTGGCACT
GGATCCGGCAGTTTCCAGGAAACAAACTGGAATGGATGGGCTACATACACTACA
GTGGTAGTACTAAGTACAACCCATCTCTCAAAAGTCGATTCTCTATCACTCGA
GACACATCCAAGAACCAGTTCTTCCTGCAGTTGAATTCTGTGACTACTGAGGACA
CAGCCACATATTACTGTGCAAGAGGGACCGACAATGCTGTGGACTACTGGGGC
CAAGGGACCACGGTCACCGTCTCCTCA C51 Gene Sequence (Light Chain) (SEQ ID NO.: 8)
GACATTGAGCTCACCCAGTCTCCATCCTCCCTAGCTGTGTCAGTTGGAGAGAAGG
TTAATATGAGCTGCAAGTCCAGTCAGAGCCTTTTATATAGTAGCAATCAAAAG
AACTACTTGGCCTGGTACCAGCAGAAACCAGGGCAGTCTCCTAAATTGCTGATT
TACTGGGCATCCAGTAGGGAATCTGGGGTCCCTGATCGCTTCACAGGCAGTGG
ATCTGGGACAGATTTCACTCTCACCATCAGCAGTGTGAAGGCTGAAGACCTGGCA
GTTTATTACTGTCAGCAATATTATATCTATCCTCTCACGTTCGGTGCTGGGACC
AAGCTGGAGCTGAAACGG Fig. 1B
C51 Amino Acid Sequence (Heavy Chain) (SEQ ID NO.: 5)
QVKLQESGPDQVKPSQSLSLTCTVTVYSITSGYSWHWIRQFPGNKLEWMG**YIHYSG
STKYNPSLKSRFSITRDTSKNQFFLQLNSVTTEDTATYYCARGTDNAVDY**WG
QGTTVTVSS C51 Amino Acid Sequence (Light Chain) (SEQ ID NO.: 6)
DIELTQSPSSLAVSVGEKVNMSCKSSQSLLYSSNQKNYLAWYQQKPGQSPKLLIY**W
ASSRESGVPDRFTGSGSGTDFTLTISSVKAEDLAVYYCQQYYIYPLT**FGAGTKLEL
KR

Fig. 1C

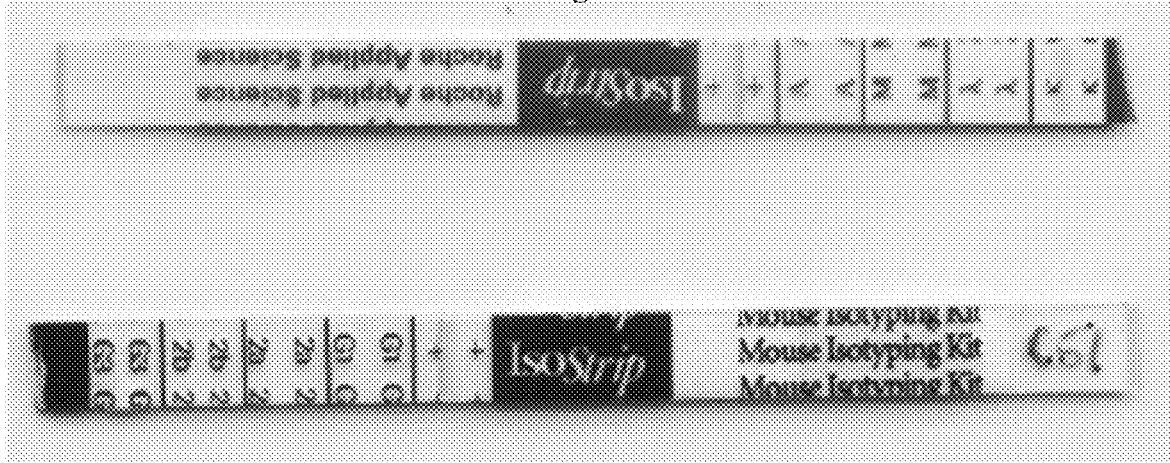

Fig. 2A

| Breast Cancer Cell Lines | | | | | |
|---|---|---|---|---|---|
| | BT474 | BT20 | CAMA-1 | HCC1937 | HCC1954 | HCC2218 |
| C51 | 4 | 4 | 4 | 3 | 4 | 4 |

| Breast Cancer Cell Lines | | | | |
|---|---|---|---|---|
| | HS578T | MCF7 | MDA MB453 | SKBR3 | T47D |
| C51 | 2 | 4 | 4 | 4 | 4 |

| Colorectal Cancer Cell Lines | | | | | | | |
|---|---|---|---|---|---|---|---|
| | COLO 205 | HCC2998 | HCT15 | HCT116 | HT29 | KM12 | LS174T | SW620 |
| C51 | 4 | 0 | 0 | 0 | 2 | 2 | 2 | 2 |

| Kidney Cancer Cell Lines | | | | | | | |
|---|---|---|---|---|---|---|---|
| | 786O | A498 | ACHN | CAKI1 | UO31 | RXF393 | SN12C | TK10 |
| C51 | 4 | 3 | 4 | 3 | 3 | 3 | 0 | 4 |

| Liver Cancer Cell Lines | | | |
|---|---|---|---|
| | HEP3B | HEPG2 | HUH7 | PLC |
| C51 | 3 | 1 | 4 | 4 |

| Ovarian Cancer Cell Lines | | | | | |
|---|---|---|---|---|---|
| | CAOV3 | CH1 | IGROV1 | OV17R | OV90 | OVCA432 |
| C51 | 3 | 0 | 3 | 0 | 2 | 3 |

| Ovarian Cancer Cell Lines | | | | |
|---|---|---|---|---|
| | OVCAR3 | OVCAR8 | OVCA433 | PEA1 | SKOV3 |
| C51 | 3 | 4 | 2 | 4 | 3 |

| Normal Cell Lines | | | | |
|---|---|---|---|---|
| | IMR90 | IOSE523 | HEK293 | HFF | hTERT-HME1 |
| C51 | 0 | 0 | 0 | 0 | 0 |

| Legend | | |
|---|---|---|
| | 4 | >80% binding |
| | 3 | 60-80% binding |
| | 2 | 40-60% binding |
| | 1 | 10-40% binding |
| | 0 | <10% binding |

Fig. 2B

| EMT Category† | Ovarian Cell line | mAb clone C51* |
|---|---|---|
| E | CaOV3 | +++ |
| E | OVCAR3 | ++++ |
| E | OVCAR8 | ++++ |
| E | OV90 | ++ |
| E | IGROV1 | +++ |
| IE | OV17R | - |
| IE | OVCA432 | +++ |
| IE | OVCA433 | ++ |
| IM | CH1 | - |
| IM | HEY | - |
| IM | HEYC2 | - |
| IM | SKOV3 | +++ |
| IM | SKOV3(D10) | + |
| M | A2780 | - |
| M | COLO720E | - |
| M | HEYA8 | - |
| M | OVCAR10 | - |
| M | TOV112 | - |
| U | IOSE523 | - |

| EMT Category† | Breast Cell line | mAb clone C51* |
|---|---|---|
| E | BT474 | ++++ |
| E | CAMA1 | ++++ |
| E | HCC2218 | ++++ |
| E | MDA453 | ++++ |
| E | MCF7 | ++++ |
| E | SKBR3 | ++++ |
| E | T47D | ++++ |
| IE | BT20 | ++++ |
| IE | HCC1937 | +++ |
| IM | HCC1954 | ++++ |
| M | MCF10A | ++ |
| M | MDA-MB-231 | + |
| M | BT549 | - |
| M | HS578T | ++++ |
| U | 184B5 | ++++ |
| U | HCC1395 | - |

Fig. 10A

Gene Sequence 2448 (Heavy Chain ) (SEQ ID NO.:3)
GTACAGCTGCAGGAGTCAGGACCTGACCTGGTGAAACCTTCTCGGTCACTTTCAC
TCACCTGCACTGTCACTG<u>GCTACTCCATCACCAGTGGTTATAGCTGGCAC</u>TGG
ATCCGGCAGTTTCCAGGAAACAAACTGGAATGGATGGGCT<u>ACATACACTACAGT
GGTAGCACTAAGTACAACCCATCTCTCAAAAGTC</u>GAATCTCTATCACTCGAGA
CACATCCAAGAACCAGTTCTTCCTGCAGTTGAATTCTGTGACTACTGAGGACGCA
GCCACATATTACTGTGCAAGGG<u>GGAGTAACTACGGATTTGACTACT</u>GGGGCCA
AGGCACCACTCTCACAGTCTCCTCA

Gene Sequence 2448 (Light Chain ) (SEQ ID NO.:4)
GACATTGAGCTCACCCAGTCTCCATCCTCCCTAGCTGTGTCAGTTGGAGAGAAGG
TTACTATGAGCTGCA<u>AGTCCAGTCAGAGCCTTTTATATAGTAACGATCAAAAG
AACTACTTGGCCT</u>GGTACCAACAGAAACCAGGGCAGTCTCCTAAACTGCTGATT
TACT<u>GGGCATCTATTAGGGAATCTG</u>GGGTCCCTGATCGCTTCACAGGCAGTGGA
TCTGGGACAGATTTCACTCTCACCATCAGCAGTGTGAAGGCTGAAGACCTGGCAG
TTTATTACTGTC<u>AGCAATATTATATCTATCCTCTCACGT</u>TCGGTGCTGGGACCA
AGCTGGAAATAAAACGG

Fig. 10B

Amino Acid Sequence 2448 (Heavy Chain ) (SEQ ID NO.:1)
VQLQESGPDLVKPSRSLSLTCTVT<u>GYSITSGYSWH</u>WIRQFPGNKLEWMG<u>YIHYSGST
KYNPSLKS</u>RISITRDTSKNQFFLQLNSVTTEDAATYYCAR<u>GSNYGFDY</u>WGQGTTLTV
SS

Amino Acid Sequence 2448 (Light Chain ) (SEQ ID NO.:2)
DIELTQSPSSLAVSVGEKVTMSC<u>KSSQSLLYSNDQKNYLA</u>WYQQKPGQSPKLLIY<u>W
ASIRES</u>GVPDRFTGSGSGTDFTLTISSVKAEDLAVYYC<u>QQYYIYPLT</u>FGAGTKLEIKR

Fig. 10C

Fig. 11A

| 2448 | Breast Cancer Cell Lines | | | | | |
|---|---|---|---|---|---|---|
| | BT474 | BT20 | CAMA-1 | HCC1937 | HCC1954 | HCC2218 |
| | 4 | 4 | 4 | 4 | 4 | 4 |

| 2448 | Breast Cancer Cell Lines | | | | |
|---|---|---|---|---|---|
| | HS578T | MCF7 | MDA MB453 | SKBR3 | T47D |
| | 4 | 4 | 4 | 4 | 4 |

| 2448 | Colorectal Cancer Cell Lines | | | | | | | |
|---|---|---|---|---|---|---|---|---|
| | COLO 205 | HCC2998 | HCT15 | HCT116 | HT29 | KM12 | LS174T | SW620 |
| | 3 | 0 | 0 | 0 | 4 | 4 | 1 | 4 |

| 2448 | Kidney Cancer Cell Lines | | | | | | | |
|---|---|---|---|---|---|---|---|---|
| | 786O | A498 | ACHN | CAKI1 | UO31 | RXF393 | SN12C | TK10 |
| | 4 | 4 | 4 | 3 | 4 | 4 | 2 | 4 |

| 2448 | Liver Cancer Cell Lines | | | |
|---|---|---|---|---|
| | HEP3B | HEPG2 | HUH7 | PLC |
| | 4 | 1 | 4 | 3 |

| 2448 | Ovarian Cancer Cell Lines | | | | | |
|---|---|---|---|---|---|---|
| | CAOV3 | CH1 | IGROV1 | OV17R | OV90 | OVCA432 |
| | 3 | 1 | 4 | 1 | 3 | 4 |

| 2448 | Ovarian Cancer Cell Lines | | | | |
|---|---|---|---|---|---|
| | OVCAR3 | OVCAR8 | OVCA433 | PEA1 | SKOV3 |
| | 4 | 4 | 4 | 4 | 3 |

| 2448 | Normal Cell Lines | | | | |
|---|---|---|---|---|---|
| | IMR90 | IOSE523 | HEK293 | HFF | hTERT-HME1 |
| | 1 | 0 | 0 | 0 | 1 |

| Legend | 4 | >80% binding |
|---|---|---|
| | 3 | 60-80% binding |
| | 2 | 40-60% binding |
| | 1 | 10-40% binding |
| | 0 | <10% binding |

Fig. 11B

| Ovarian | | mAb clone | Breast | | mAb clone |
|---|---|---|---|---|---|
| EMT Category† | Cell line | 2448* | EMT Category† | Cell line | 2448* |
| E | CaOV3 | +++ | E | BT474 | ++++ |
| E | OVCAR3 | +++ | E | CAMA1 | ++++ |
| E | OVCAR8 | ++++ | E | HCC2218 | ++++ |
| E | OV90 | +++ | E | MDA453 | ++++ |
| E | IGROV1 | ++++ | E | MCF7 | ++++ |
| IE | OV17R | + | E | SKBR3 | ++++ |
| IE | OVCA432 | ++++ | E | T47D | ++++ |
| IE | OVCA433 | +++ | IE | BT20 | ++++ |
| IM | CH1 | + | IE | HCC1937 | ++++ |
| IM | HEY | - | IM | HCC1954 | ++++ |
| IM | HEYC2 | - | M | MCF10A | ++ |
| IM | SKOV3 | +++ | M | MDA-MB-231 | - |
| IM | SKOV3(D10) | + | M | BT549 | - |
| M | A2780 | - | M | HS578T | ++ |
| M | COLO720E | - | U | 184B5 | ++++ |
| M | HEYA8 | - | U | HCC1395 | - |
| M | OVCAR10 | - | | | |
| M | TOV112 | - | | | |
| U | IOSE523 | - | | | |

Fig. 11C
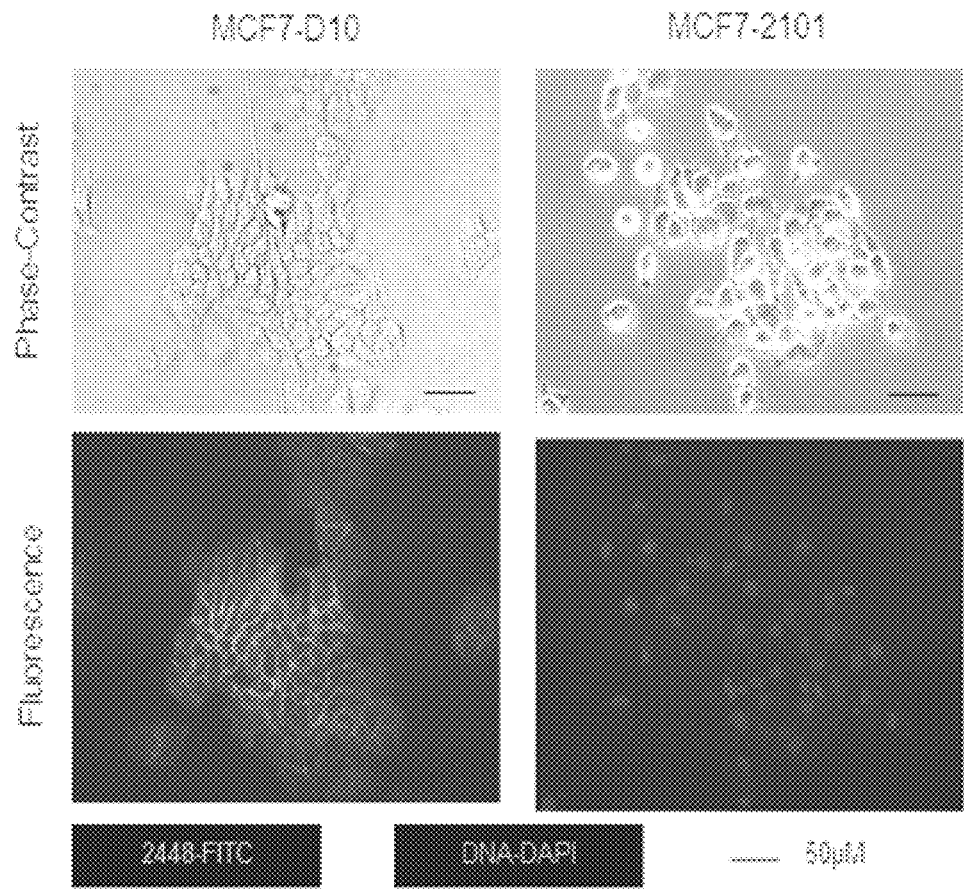
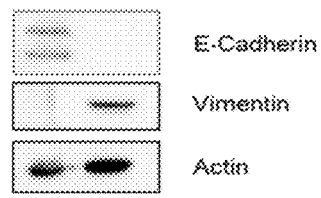
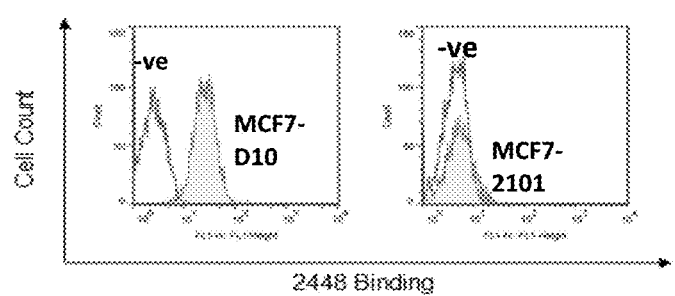

Fig. 12A

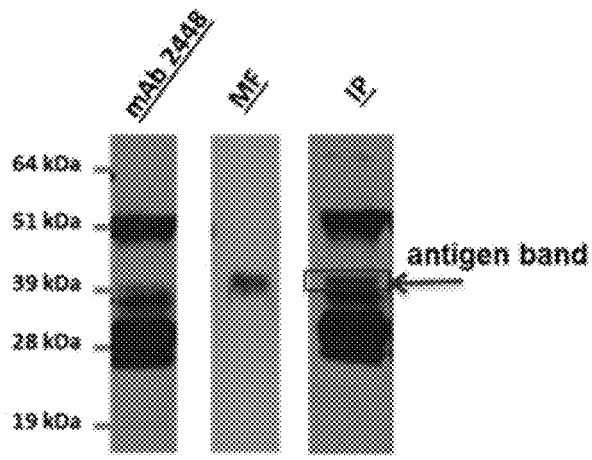

Fig. 12B

| Accession | # Peptides | # AAs | MW [kDa] | Description |
|---|---|---|---|---|
| P07355 | 4 | 339 | 38.6 | Annexin A2 OS=Homo sapiens GN=ANXA2 PE=1 SV=2 - [ANXA2_HUMAN] |

Fig. 12C

MSTVHEILCKLSLEGDHSTPPSAYGSVKAYTNFDAERDALNIETAIKTKGVDEVTIV
NILTNRSNAQRQDIAFAYQRRTKKELASALKSALSGHLETVILGLLKTPAQYDASEL
KASMKGLGTDEDSLIEIICSRTNQELQEINRVYKEMYKTDLEKDIISDTSGDFRKLM
VALAKGRRAEDGSVIDYELIDQDARDLYDAGVKRKGTDVPKWISIMTERSVPHLQ
KVFDRYKSYSPYDMLESIRKEVKGDLENAFLNLVQCIQNKPLYFADRLYDSMKGK
GTRDKVLIRIMVSRSEVDMLKIRSEFKRKYGKSLYYYIQQDTKGDYQKALLYLCGG
DD (SEQ ID NO: 30)

Fig. 18
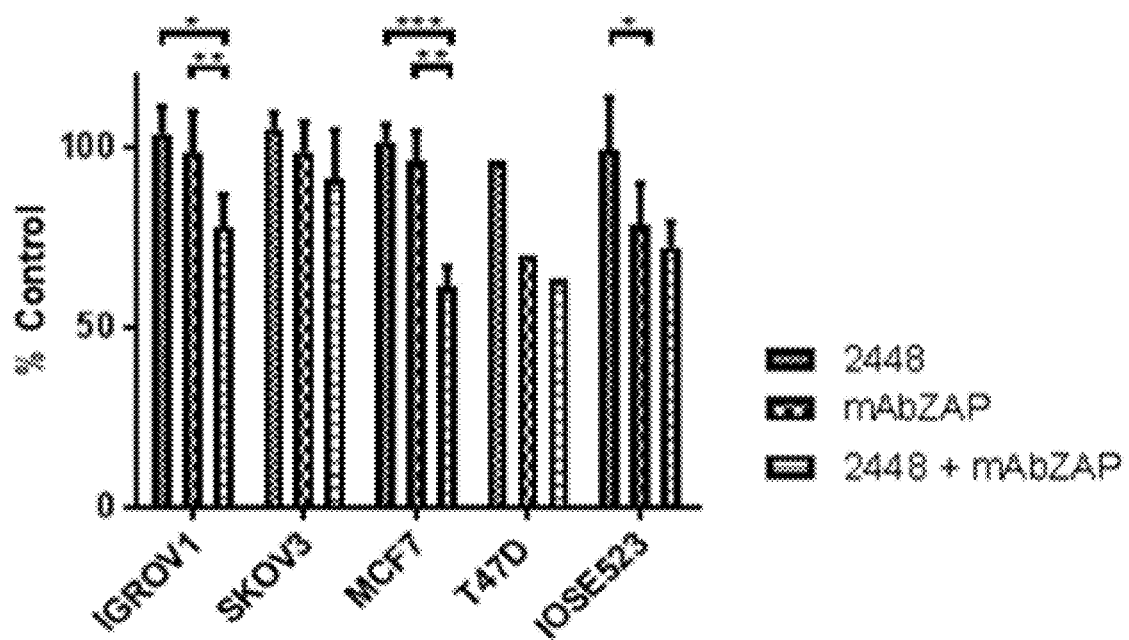
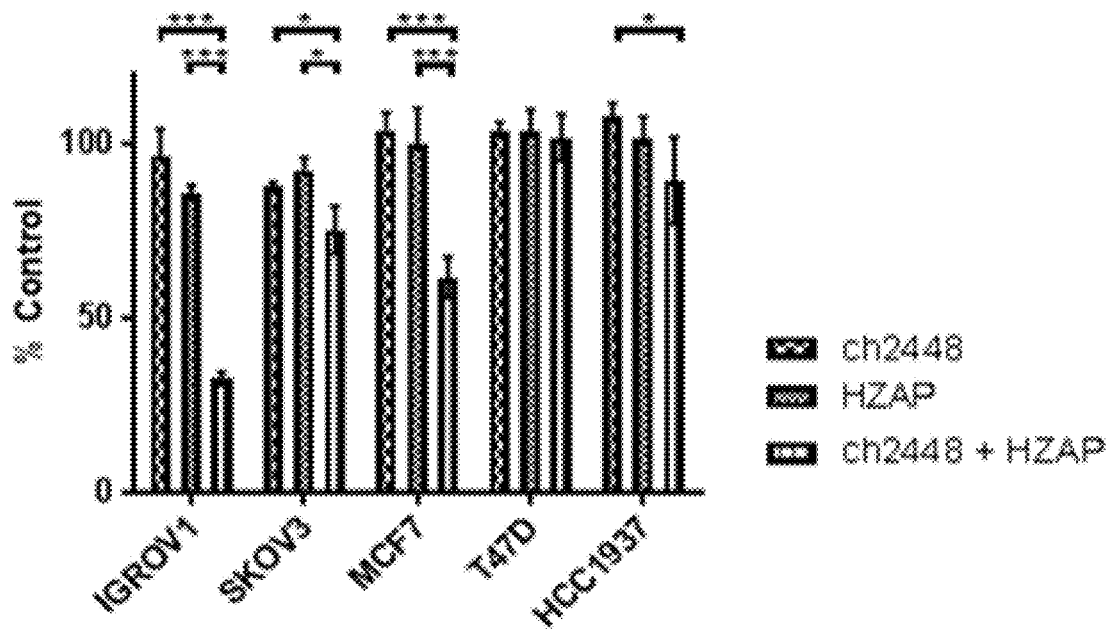

Fig. 22A
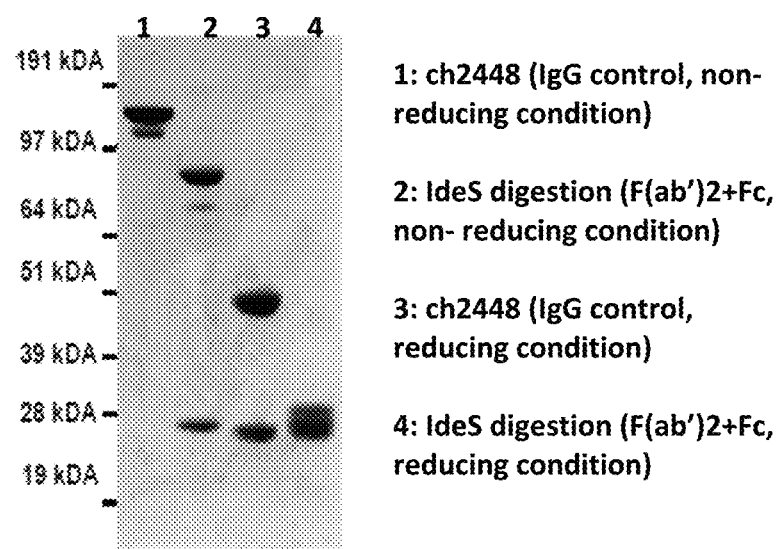
1: ch2448 (IgG control, non-reducing condition)
2: IdeS digestion (F(ab')2+Fc, non- reducing condition)
3: ch2448 (IgG control, reducing condition)
4: IdeS digestion (F(ab')2+Fc, reducing condition)
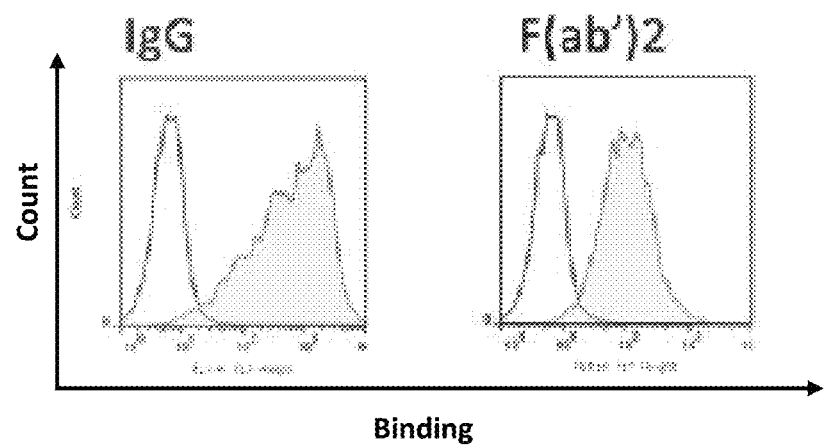

Fig. 26A
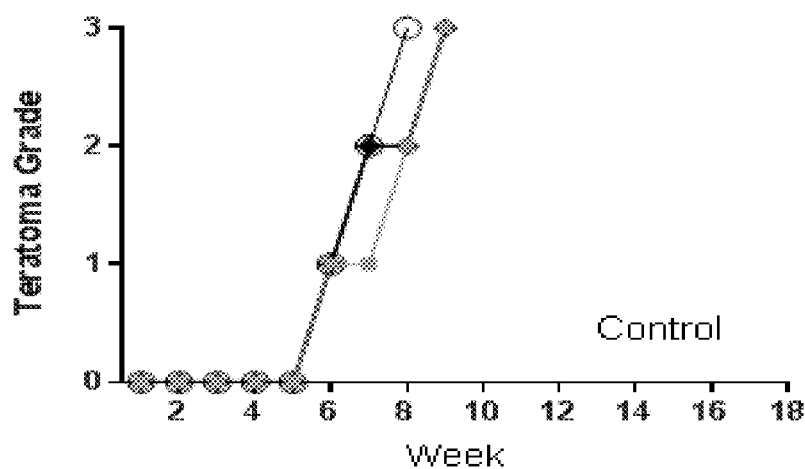
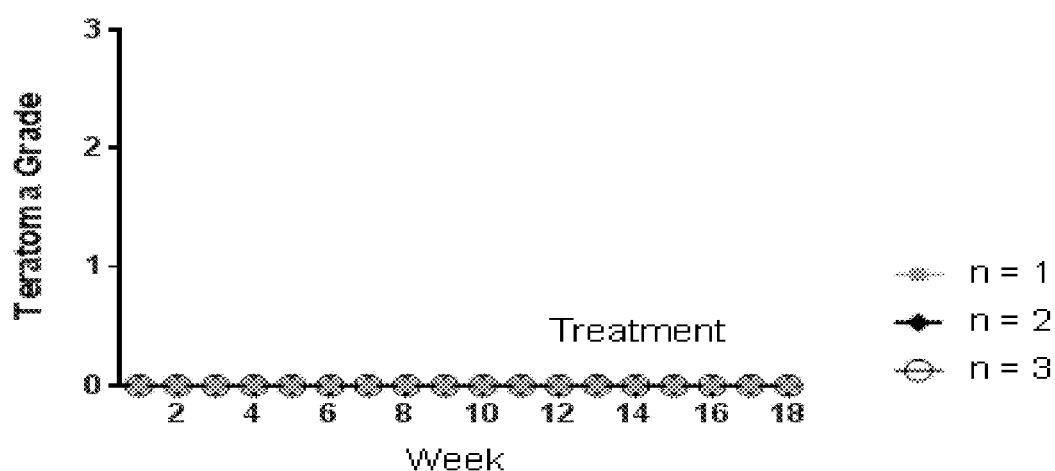

Fig. 26B
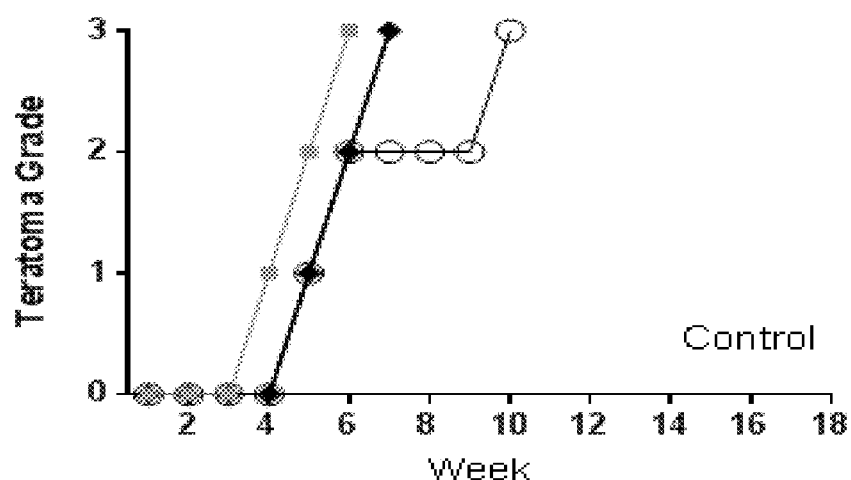
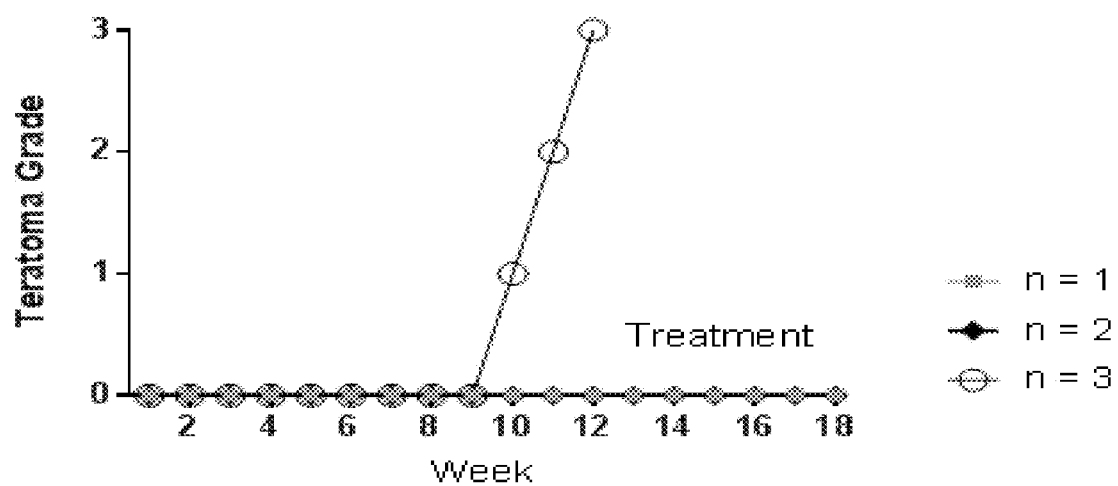

```
                        SEQUENCE LISTING

<160> NUMBER OF SEQ ID NOS: 30

<210> SEQ ID NO 1
<211> LENGTH: 116
<212> TYPE: PRT
<213> ORGANISM: Artificial Sequence
<220> FEATURE:
<223> OTHER INFORMATION: Isolated antibody

<400> SEQUENCE: 1

Val Gln Leu Gln Glu Ser Gly Pro Asp Leu Val Lys Pro Ser Arg Ser
1               5                   10                  15

Leu Ser Leu Thr Cys Thr Val Thr Gly Tyr Ser Ile Thr Ser Gly Tyr
            20                  25                  30

Ser Trp His Trp Ile Arg Gln Phe Pro Gly Asn Lys Leu Glu Trp Met
        35                  40                  45

Gly Tyr Ile His Tyr Ser Gly Ser Thr Lys Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Val Thr Thr Glu Asp Ala Ala Thr Tyr Tyr Cys Ala
                85                  90                  95

Arg Gly Ser Asn Tyr Gly Phe Asp Tyr Trp Gly Gln Gly Thr Thr Leu
            100                 105                 110

Thr Val Ser Ser
        115

<210> SEQ ID NO 2
<211> LENGTH: 114
<212> TYPE: PRT
<213> ORGANISM: Artificial Sequence
<220> FEATURE:
<223> OTHER INFORMATION: Isolated antibody

<400> SEQUENCE: 2

Asp Ile Glu Leu Thr Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Asn Asp Gln Lys Asn Tyr Leu Ala Trp Tyr Gln Gln Lys Pro Gly Gln
        35                  40                  45

Ser Pro Lys Leu Leu Ile Tyr Trp Ala Ser Ile Arg Glu Ser Gly Val
```

```
                50                  55                  60
Pro Asp Arg Phe Thr Gly Ser Gly Ser Gly Thr Asp Phe Thr Leu Thr
65                      70                  75                  80

Ile Ser Ser Val Lys Ala Glu Asp Leu Ala Val Tyr Tyr Cys Gln Gln
                    85                  90                  95

Tyr Tyr Ile Tyr Pro Leu Thr Phe Gly Ala Gly Thr Lys Leu Glu Ile
                100                 105                 110

Lys Arg

<210> SEQ ID NO 3
<211> LENGTH: 348
<212> TYPE: DNA
<213> ORGANISM: Artificial Sequence
<220> FEATURE:
<223> OTHER INFORMATION: Isolated antibody

<400> SEQUENCE: 3
gtacagctgc aggagtcagg acctgacctg gtgaaacctt ctcggtcact ttcactcacc      60
tgcactgtca ctggctactc catcaccagt ggttatagct ggcactggat ccggcagttt     120
ccaggaaaca aactggaatg gatgggctac atacactaca gtggtagcac taagtacaac     180
ccatctctca aaagtcgaat ctctatcact cgagacacat ccaagaacca gttcttcctg     240
cagttgaatt ctgtgactac tgaggacgca gccacatatt actgtgcaag ggggagtaac     300
tacggatttg actactgggg ccaaggcacc actctcacag tctcctca                  348

<210> SEQ ID NO 4
<211> LENGTH: 342
<212> TYPE: DNA
<213> ORGANISM: Artificial Sequence
<220> FEATURE:
<223> OTHER INFORMATION: Isolated antibody

<400> SEQUENCE: 4
gacattgagc tcacccagtc tccatcctcc ctagctgtgt cagttggaga gaaggttact      60
atgagctgca gtccagtca gagcctttta tatagtaacg atcaaaagaa ctacttggcc     120
tggtaccaac agaaaccagg gcagtctcct aaactgctga tttactgggc atctattagg     180
gaatctgggg tccctgatcg cttcacaggc agtggatctg ggacagattt cactctcacc     240
atcagcagtg tgaaggctga agacctggca gtttattact gtcagcaata ttatatctat     300
cctctcacgt tcggtgctgg gaccaagctg gaaataaaac gg                        342

<210> SEQ ID NO 5
<211> LENGTH: 117
<212> TYPE: PRT
<213> ORGANISM: Artificial Sequence
<220> FEATURE:
<223> OTHER INFORMATION: Isolated antibody

<400> SEQUENCE: 5

Gln Val Lys Leu Gln Glu Ser Gly Pro Asp Val Lys Pro Ser Gln
1               5                   10                  15

Ser Leu Ser Leu Thr Cys Thr Val Thr Val Tyr Ser Ile Thr Ser Gly
                20                  25                  30

Tyr Ser Trp His Trp Ile Arg Gln Phe Pro Gly Asn Lys Leu Glu Trp
            35                  40                  45

Met Gly Tyr Ile His Tyr Ser Gly Ser Thr Lys Tyr Asn Pro Ser Leu
        50                  55                  60
```

```
Lys Ser Arg Phe Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Ala Arg Gly Thr Asp Asn Ala Val Asp Tyr Trp Gly Gln Gly Thr Thr
            100                 105                 110

Val Thr Val Ser Ser
        115

<210> SEQ ID NO 6
<211> LENGTH: 114
<212> TYPE: PRT
<213> ORGANISM: Artificial Sequence
<220> FEATURE:
<223> OTHER INFORMATION: Isolated antibody

<400> SEQUENCE: 6

Asp Ile Glu Leu Thr Gln Ser Pro Ser Ser Leu Ala Val Ser Val Gly
 1               5                  10                  15

Glu Lys Val Asn Met Ser Cys Lys Ser Ser Gln Ser Leu Leu Tyr Ser
             20                  25                  30

Ser Asn Gln Lys Asn Tyr Leu Ala Trp Tyr Gln Lys Pro Gly Gln
         35                  40                  45

Ser Pro Lys Leu Leu Ile Tyr Trp Ala Ser Ser Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ile Tyr Pro Leu Thr Phe Gly Ala Gly Thr Lys Leu Glu Leu
            100                 105                 110

Lys Arg

<210> SEQ ID NO 7
<211> LENGTH: 351
<212> TYPE: DNA
<213> ORGANISM: Artificial Sequence
<220> FEATURE:
<223> OTHER INFORMATION: Isolated antibody

<400> SEQUENCE: 7
caggtgaaac tgcaggagtc aggacctgac caggtgaaac cctctcagtc actttcactc      60
acctgcactg tcactgtcta ctccatcacc agtggttata gctggcactg gatccggcag     120
tttccaggaa acaaactgga atggatgggc tacatacact acagtggtag tactaagtac     180
aacccatctc tcaaaagtcg attctctatc actcgagaca catccaagaa ccagttcttc     240
ctgcagttga attctgtgac tactgaggac acagccacat attactgtgc aagagggacc     300
gacaatgctg tggactactg gggccaaggg accacggtca ccgtctcctc a              351

<210> SEQ ID NO 8
<211> LENGTH: 342
<212> TYPE: DNA
<213> ORGANISM: Artificial Sequence
<220> FEATURE:
<223> OTHER INFORMATION: Isolated antibody

<400> SEQUENCE: 8
gacattgagc tcacccagtc tccatcctcc ctagctgtgt cagttggaga gaaggttaat      60
```

-continued

```
atgagctgca agtccagtca gagccttttta tatagtagca atcaaaagaa ctacttggcc    120
tggtaccagc agaaaccagg gcagtctcct aaattgctga tttactgggc atccagtagg    180
gaatctgggg tccctgatcg cttcacaggc agtggatctg ggacagattt cactctcacc    240
atcagcagtg tgaaggctga agacctggca gtttattact gtcagcaata ttatatctat    300
cctctcacgt tcggtgctgg gaccaagctg gagctgaaac gg                       342
```

<210> SEQ ID NO 9
<211> LENGTH: 11
<212> TYPE: PRT
<213> ORGANISM: Artificial Sequence
<220> FEATURE:
<223> OTHER INFORMATION: Isolated antibody

<400> SEQUENCE: 9

Gly Tyr Ser Ile Thr Ser Gly Tyr Ser Trp His
1               5                   10

<210> SEQ ID NO 10
<211> LENGTH: 16
<212> TYPE: PRT
<213> ORGANISM: Artificial Sequence
<220> FEATURE:
<223> OTHER INFORMATION: Isolated antibody

<400> SEQUENCE: 10

Tyr Ile His Tyr Ser Gly Ser Thr Lys Tyr Asn Pro Ser Leu Lys Ser
1               5                   10                  15

<210> SEQ ID NO 11
<211> LENGTH: 8
<212> TYPE: PRT
<213> ORGANISM: Artificial Sequence
<220> FEATURE:
<223> OTHER INFORMATION: Isolated antibody

<400> SEQUENCE: 11

Gly Ser Asn Tyr Gly Phe Asp Tyr
1               5

<210> SEQ ID NO 12
<211> LENGTH: 17
<212> TYPE: PRT
<213> ORGANISM: Artificial Sequence
<220> FEATURE:
<223> OTHER INFORMATION: Isolated antibody

<400> SEQUENCE: 12

Lys Ser Ser Gln Ser Leu Leu Tyr Ser Asn Asp Gln Lys Asn Tyr Leu
1               5                   10                  15
Ala

<210> SEQ ID NO 13
<211> LENGTH: 7
<212> TYPE: PRT
<213> ORGANISM: Artificial Sequence
<220> FEATURE:
<223> OTHER INFORMATION: Isolated antibody

<400> SEQUENCE: 13

Trp Ala Ser Ile Arg Glu Ser
1               5

<210> SEQ ID NO 14

<211> LENGTH: 9
<212> TYPE: PRT
<213> ORGANISM: Artificial Sequence
<220> FEATURE:
<223> OTHER INFORMATION: Isolated antibody

<400> SEQUENCE: 14

Gln Gln Tyr Tyr Ile Tyr Pro Leu Thr
1               5

<210> SEQ ID NO 15
<211> LENGTH: 32
<212> TYPE: DNA
<213> ORGANISM: Artificial Sequence
<220> FEATURE:
<223> OTHER INFORMATION: Isolated antibody

<400> SEQUENCE: 15
gctactccat caccagtggt tatagctggc ac                                       32

<210> SEQ ID NO 16
<211> LENGTH: 48
<212> TYPE: DNA
<213> ORGANISM: Artificial Sequence
<220> FEATURE:
<223> OTHER INFORMATION: Isolated antibody

<400> SEQUENCE: 16
acatacacta cagtggtagc actaagtaca acccatctct caaaagtc                      48

<210> SEQ ID NO 17
<211> LENGTH: 24
<212> TYPE: DNA
<213> ORGANISM: Artificial Sequence
<220> FEATURE:
<223> OTHER INFORMATION: Isolated antibody

<400> SEQUENCE: 17
ggagtaacta cggatttgac tact                                                24

<210> SEQ ID NO 18
<211> LENGTH: 51
<212> TYPE: DNA
<213> ORGANISM: Artificial Sequence
<220> FEATURE:
<223> OTHER INFORMATION: Isolated antibody

<400> SEQUENCE: 18
agtccagtca gagccttta tatagtaacg atcaaaagaa ctacttggcc t                   51

<210> SEQ ID NO 19
<211> LENGTH: 21
<212> TYPE: DNA
<213> ORGANISM: Artificial Sequence
<220> FEATURE:
<223> OTHER INFORMATION: Isolated antibody

<400> SEQUENCE: 19
gggcatctat tagggaatct g                                                   21

<210> SEQ ID NO 20
<211> LENGTH: 27
<212> TYPE: DNA
<213> ORGANISM: Artificial Sequence
<220> FEATURE:
<223> OTHER INFORMATION: Isolated antibody

<400> SEQUENCE: 20
agcaatatta tatctatcct ctcacgt                                              27

<210> SEQ ID NO 21
<211> LENGTH: 11
<212> TYPE: PRT
<213> ORGANISM: Artificial Sequence
<220> FEATURE:
<223> OTHER INFORMATION: Isolated antibody

<400> SEQUENCE: 21

Val Tyr Ser Ile Thr Ser Gly Tyr Ser Trp His
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Isolated antibody

<400> SEQUENCE: 22

Gly Thr Asp Asn Ala Val Asp Tyr
1               5

<210> SEQ ID NO 23
<211> LENGTH: 17
<212> TYPE: PRT
<213> ORGANISM: Artificial Sequence
<220> FEATURE:
<223> OTHER INFORMATION: Isolated antibody

<400> SEQUENCE: 23

Lys Ser Ser Gln Ser Leu Leu Tyr Ser Ser Asn Gln Lys Asn Tyr Leu
1               5                   10                  15

Ala

<210> SEQ ID NO 24
<211> LENGTH: 7
<212> TYPE: PRT
<213> ORGANISM: Artificial Sequence
<220> FEATURE:
<223> OTHER INFORMATION: Isolated antibody

<400> SEQUENCE: 24

Trp Ala Ser Ser Arg Glu Ser
1               5

<210> SEQ ID NO 25
<211> LENGTH: 33
<212> TYPE: DNA
<213> ORGANISM: Artificial Sequence
<220> FEATURE:
<223> OTHER INFORMATION: Isolated antibody

<400> SEQUENCE: 25
tctactccat caccagtggt tatagctggc act                                       33

<210> SEQ ID NO 26
<211> LENGTH: 48
<212> TYPE: DNA
<213> ORGANISM: Artificial Sequence
<220> FEATURE:
<223> OTHER INFORMATION: Isolated antibody

<400> SEQUENCE: 26

```
acatacacta cagtggtagt actaagtaca acccatctct caaaagtc        48
```

<210> SEQ ID NO 27
<211> LENGTH: 24
<212> TYPE: DNA
<213> ORGANISM: Artificial Sequence
<220> FEATURE:
<223> OTHER INFORMATION: Isolated antibody

<400> SEQUENCE: 27

```
ggaccgacaa tgctgtggac tact                                  24
```

<210> SEQ ID NO 28
<211> LENGTH: 51
<212> TYPE: DNA
<213> ORGANISM: Artificial Sequence
<220> FEATURE:
<223> OTHER INFORMATION: Isolated antibody

<400> SEQUENCE: 28

```
agtccagtca gagcctttta tatagtagca atcaaaagaa ctacttggcc t    51
```

<210> SEQ ID NO 29
<211> LENGTH: 21
<212> TYPE: DNA
<213> ORGANISM: Artificial Sequence
<220> FEATURE:
<223> OTHER INFORMATION: Isolated antibody

<400> SEQUENCE: 29

```
gggcatccag tagggaatct g                                     21
```

<210> SEQ ID NO 30
<211> LENGTH: 339
<212> TYPE: PRT
<213> ORGANISM: Artificial Sequence
<220> FEATURE:
<223> OTHER INFORMATION: Isolated antibody

<400> SEQUENCE: 30

Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45

Lys Gly Val Asp Glu Val Thr Ile Val Asn Ile Leu Thr Asn Arg Ser
    50                  55                  60

Asn Ala Gln Arg Gln Asp Ile Ala Phe Ala Tyr Gln Arg Arg Thr Lys
65                  70                  75                  80

Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
    130                 135                 140

Arg Val Tyr Lys Glu Met Tyr Lys Thr Asp Leu Glu Lys Asp Ile Ile
145                 150                 155                 160

```
Ser Asp Thr Ser Gly Asp Phe Arg Lys Leu Met Val Ala Leu Ala Lys
            165             170             175

Gly Arg Arg Ala Glu Asp Gly Ser Val Ile Tyr Glu Leu Ile Asp
            180             185             190

Gln Asp Ala Arg Asp Leu Tyr Asp Ala Gly Val Lys Arg Lys Gly Thr
            195             200             205

Asp Val Pro Lys Trp Ile Ser Ile Met Thr Glu Arg Ser Val Pro His
        210             215             220

Leu Gln Lys Val Phe Asp Arg Tyr Lys Ser Tyr Ser Pro Tyr Asp Met
225             230             235             240

Leu Glu Ser Ile Arg Lys Glu Val Lys Gly Asp Leu Glu Asn Ala Phe
            245             250             255

Leu Asn Leu Val Gln Cys Ile Gln Asn Lys Pro Leu Tyr Phe Ala Asp
            260             265             270

Arg Leu Tyr Asp Ser Met Lys Gly Lys Gly Thr Arg Asp Lys Val Leu
            275             280             285

Ile Arg Ile Met Val Ser Arg Ser Glu Val Asp Met Leu Lys Ile Arg
        290             295             300

Ser Glu Phe Lys Arg Lys Tyr Gly Lys Ser Leu Tyr Tyr Tyr Ile Gln
305             310             315             320

Gln Asp Thr Lys Gly Asp Tyr Gln Lys Ala Leu Leu Tyr Leu Cys Gly
            325             330             335

Gly Asp Asp
```

ANTI-ANNEXIN A2 MONOCLONAL ANTIBODIES

CROSS-REFERENCE TO RELATED APPLICATIONS

This patent application is a continuation of U.S. patent application Ser. No. 16/321,020 filed 26 Jan. 2019, which is a U.S. National Phase application under 35 U.S.C. § 371 of International Application No. PCT/SG2017/050382, filed 26 Jul. 2017, which claims the benefit of priority of Singapore application No. 10201606178X, filed 26 Jul. 2016, the contents of which were incorporated by reference in the entirety for all purposes.

INCORPORATION BY REFERENCE

This patent application incorporates by reference the material (i.e., Sequence Listing) in the ASCII text file named 9322P150_Seq_List.txt, created on Jan. 25, 2019, having a file size of 14,109 bytes.

FIELD OF THE INVENTION

The present invention relates generally to antibodies. Specifically, the invention relates to anti-annexin A2 monoclonal antibodies and uses thereof.

BACKGROUND OF THE INVENTION

Annexin A2 (ANXA2) is involved in diverse cellular processes and clinical associations, especially in cancer progression. It is a calcium-dependent phospholipid-binding protein whose function is to help organize exocytosis of intracellular proteins to the extracellular domain. ANXA2 is a pleiotropic protein meaning that its function is dependent on place and time in the body.

Increased expression of ANXA2 is frequently observed in a broad spectrum of cancer cells. ANXA2 is overexpressed in acute lymphoblastic leukemia (ALL), APL, breast cancer, colorectal carcinoma (CRC), gastric cancer, glioma, hepatocellular carcinoma (HCC), lung cancer, multiple myeloma (MM), oral squamous cell carcinoma (OSCC), and pancreatic cancer. The up-regulation of ANXA2 in cancer may have several clinical applications, including as a diagnostic marker for early detection, a predictive factor for prognosis, or a marker for drug resistance.

To date there are no anti-ANXA2 monoclonal antibodies that could be used for antibody therapy or as antibody-drug conjugates for cancer treatment. In addition, there are no reported antibodies targeting unique cancer specific glycoforms of ANXA2. There is therefore a need to develop novel antibodies against ANXA2 that address the disadvantages of the antibodies that are currently available.

SUMMARY

In one aspect, there is provided an antigen-binding protein, or an antigen-binding fragment thereof, comprising (i) a heavy chain variable domain comprising a VHCDR1 having the amino acid sequence GYSITSGYSWH (SEQ ID NO: 9); a VHCDR2 having the amino acid sequence YIHYSGSTKYNPSLKS (SEQ ID NO: 10) and a VHCDR3 having the amino acid sequence GSNYGFDY (SEQ ID NO: 11); and (ii) a light chain variable domain comprising a VLCDR1 having the amino acid sequence KSSQSLLY-SNDQKNYLA (SEQ ID NO: 12), a VLCDR2 having the amino acid sequence WASIRES (SEQ ID NO: 13), and a VLCDR3 having the amino acid sequence QQYYIYPLT (SEQ ID NO: 14).

In another aspect, there is provided an antigen-binding protein, or an antigen-binding fragment thereof, comprising (i) a heavy chain variable domain comprising a VHCDR1 having the nucleic acid sequence GCTACTCCAT-CACCAGTGGTTATAGCTGGCAC (SEQ ID NO: 15); a VHCDR2 having the nucleic acid sequence ACATACAC-TACAGTGGTAGCACTAAGTACAACCCATCTCT-CAAAAGTC (SEQ ID NO: 16), and a VHCDR3 having the nucleic acid sequence GGAGTAACTACGGATTTGAC-TACT (SEQ ID NO: 17); and (ii) a light chain variable domain comprising a VLCDR1 having the nucleic acid sequence AGTCCAGTCAGAGCCTTTTATATAGTAAC-GATCAAAAGAACTACTTGGCCT (SEQ ID NO: 18), a VLCDR2 having the nucleic acid sequence GGGCATCT-ATTAGGGAATCTG (SEQ ID NO: 19), and a VLCDR3 having the nucleic acid sequence AGCAATATTATATC-TATCCTCTCACGT (SEQ ID NO: 20).

In another aspect, there is provided an antigen-binding protein, or an antigen-binding fragment thereof, comprising (i) a heavy chain variable domain comprising a VHCDR1 having the amino acid sequence VYSITSGYSWH (SEQ ID NO: 21); a VHCDR2 having the amino acid sequence YIHYSGSTKYNPSLKS (SEQ ID NO: 10), and a VHCDR3 having the amino acid sequence GTDNAVDY (SEQ ID NO: 22); and (ii) a light chain variable domain comprising a VLCDR1 having the amino acid sequence KSSQSLLY-SSNQKNYLA (SEQ ID NO: 23), a VLCDR2 having the amino acid sequence WASSRES (SEQ ID NO: 24), and a VLCDR3 having the amino acid sequence QQYYIYPLT (SEQ ID NO: 14).

In another aspect, there is provided, an antigen-binding protein, or an antigen-binding fragment thereof, comprising (i) a heavy chain variable domain comprising a VHCDR1 having the nucleic acid sequence TCTACTCCAT-CACCAGTGGTTATAGCTGGCACT (SEQ ID N: 25); a VHCDR2 having the nucleic acid sequence ACATACAC-TACAGTGGTAGTACTAAGTACAACCCATCTCT-CAAAAGTC (SEQ ID NO: 26), and a VHCDR3 having the nucleic acid sequence GGACCGACAATGCTGTGGAC-TACT (SEQ ID NO: 27); and (ii) a light chain variable domain comprising a VLCDR1 having the nucleic acid sequence AGTCCAGTCAGAGCCTTT-TATATAGTAGCAATCAAAAGAACTACTTGGCCT (SEQ ID NO: 28), a VLCDR2 having the nucleic acid sequence GGGCATCCAGTAGGGAATCTG (SEQ ID NO: 29), and a VLCDR3 having the nucleic acid sequence AGCAATATTATATCTATCCTCTCACGT (SEQ ID NO: 20).

In another aspect, there is provided a composition comprising a physiologically acceptable carrier and a therapeutically effective amount of the antigen-binding protein, or an antigen-binding fragment thereof, as described herein.

In another aspect, there is provided use of an antigen-binding protein, or an antigen-binding fragment thereof, as described herein, in the manufacture of a medicament for treating or preventing cancer.

In another aspect, there is provided a method for detecting cancer in a subject, the method comprising: contacting a sample obtained from the subject with an antigen-binding protein, or an antigen-binding fragment thereof as described herein in vitro; detecting the binding of the antigen-binding protein, or an antigen-binding fragment thereof in the sample; correlating the binding with a level of binding in a control sample to determine the level of binding in the sample, wherein an increase in the level of binding in the sample relative to the control sample is indicative of cancer.

In another aspect, there is provided a method for identifying a subject susceptible to cancer the method comprising: contacting a sample obtained from the subject with an antigen-binding protein, or an antigen-binding fragment thereof as described herein in vitro; detecting the binding of the antigen-binding protein, or an antigen-binding fragment thereof in the sample; correlating the binding with a level of binding in a control sample to determine the level of binding in the sample, wherein an increase in the level of binding in the sample relative to the control sample indicates that the subject is susceptible to cancer.

In another aspect, there is provided a kit when used in the method as described herein, comprising an antigen-binding protein, or antigen-binding fragment thereof as described herein, together with instructions for use.

DEFINITIONS

The following are some definitions that may be helpful in understanding the description of the present invention. These are intended as general definitions and should in no way limit the scope of the present invention to those terms alone, but are put forth for a better understanding of the following description.

The term "antigen binding protein" as used herein refers to antibodies, antibody fragments and other protein constructs, such as domains, which are capable of binding to ANXA2.

The term "antibody" is used herein in the broadest sense to refer to molecules with an immunoglobulin-like domain and includes monoclonal, recombinant, polyclonal, chimeric, humanised, bispecific and heteroconjugate antibodies; a chimeric antigen receptor (CAR), a single variable domain, a domain antibody, antigen binding fragments, immunologically effective fragments, single chain Fv, diabodies, Tandabs™, etc (for a summary of alternative "antibody" formats see Holliger and Hudson, Nature Biotechnology, 2005, Vol 23, No. 9, 1126-1136).

A "chimeric antigen receptor" may comprise an extracellular domain comprising the antigen binding domain, a transmembrane domain and an intracellular signalling domain. The extracellular domain may be linked to the transmembrane domain by a linker. The extracellular domain may also comprise a signal peptide.

The phrase "single variable domain" refers to an antigen binding protein variable domain (for example, $V_H$, $V_{HH}$, $V_L$) that specifically binds an antigen or epitope independently of a different variable region or domain.

A "domain antibody" or "dAb" may be considered the same as a "single variable domain" which is capable of binding to an antigen. A single variable domain may be a human antibody variable domain, but also includes single antibody variable domains from other species such as rodent (for example, as disclosed in WO 00/29004), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanised according to standard techniques available in the art, and such domains are considered to be "domain antibodies". As used herein $V_H$ includes camelid $V_{HH}$ domains.

As used herein the term "domain" refers to a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A domain can bind an antigen or epitope independently of a different variable region or domain.

An antigen binding fragment may be provided by means of arrangement of one or more CDRs on non-antibody protein scaffolds such as a domain. The domain may be a domain antibody or may be a domain which is a derivative of a scaffold selected from the group consisting of CTLA-4, lipocalin, SpA, an Affibody, an avimer, GroEl, transferrin, GroES and fibronectin/adnectin, which has been subjected to protein engineering in order to obtain binding to an antigen, such as ANXA2, other than the natural ligand.

An antigen binding fragment or an immunologically effective fragment may comprise partial heavy or light chain variable sequences. Fragments are at least 5, 6, 8 or 10 amino acids in length. Alternatively the fragments are at least 15, at least 20, at least 50, at least 75, or at least 100 amino acids in length.

The term "specifically binds" as used throughout the present specification in relation to antigen binding proteins means that the antigen binding protein binds to ANXA2 with no or insignificant binding to other (for example, unrelated) proteins. However, the term does not exclude the fact that the antigen binding proteins may also be cross-reactive with closely related molecules. The antigen binding proteins described herein may bind to ANXA2 with at least 2, 5, 10, 50, 100, or 1000 fold greater affinity than they bind to closely related molecules.

The term "neutralises" as used throughout the present specification means that the biological activity of ANXA2 is reduced in the presence of an antigen binding protein as described herein in comparison to the activity of ANXA2 in the absence of the antigen binding protein, in vitro or in vivo. Neutralisation may be due to one or more of blocking ANXA2 binding to its receptor, preventing ANXA2 from activating its receptor, down regulating ANXA2 or its receptor, or affecting effector functionality. The reduction or inhibition in biological activity may be partial or total. A neutralising antigen binding protein may neutralise the activity of ANXA2 by at least 20%, 30% 40%, 50%, 55%, 60%, 65%, 70%, 75%, 80%, 82%, 84%, 86%, 88%, 90%, 92%, 94%, 95%, 96%, 97%, 98%, 99% or 100% relative to ANXA2 activity in the absence of the antigen binding protein. Neutralisation may be determined or measured using one or more assays known to the skilled person or as described herein. For example, antigen binding protein binding to ANXA2 can be assessed in a sandwich ELISA, by BIAcore™, FMAT, FORTEbio, or similar in vitro assays.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs.

As used herein, the term "promoter" is intended to refer to a region of DNA that initiates transcription of a particular gene.

As used herein, the term "cancerous" relates to being affected by or showing abnormalities characteristic of cancer.

As used herein, the term "biological sample" or "sample" is meant a sample of tissue or cells from a patient that has been obtained from, removed or isolated from the patient.

The term "obtained or derived from" as used herein is meant to be used inclusively. That is, it is intended to encompass any nucleotide sequence directly isolated from a biological sample or any nucleotide sequence derived from the sample.

The method as described herein is suitable for use in a sample of fresh tissue, frozen tissue, paraffin-preserved tissue and/or ethanol preserved tissue. The sample may be a biological sample. Non-limiting examples of biological samples include whole blood or a component thereof (e.g. plasma, serum), urine, saliva lymph, bile fluid, sputum, tears, cerebrospinal fluid, bronchioalveolar lavage fluid, synovial fluid, semen, ascitic tumor fluid, breast milk and pus. In one embodiment, the sample of nucleic acid is obtained from blood, amniotic fluid or a buccal smear. In a preferred embodiment, the sample is a whole blood sample.

A biological sample as contemplated herein includes cultured biological materials, including a sample derived from cultured cells, such as culture medium collected from cultured cells or a cell pellet. Accordingly, a biological sample may refer to a lysate, homogenate or extract prepared from a whole organism or a subset of its tissues, cells or component parts, or a fraction or portion thereof. A biological sample may also be modified prior to use, for example, by purification of one or more components, dilution, and/or centrifugation.

As used herein, the term "detectable label" or "reporter" refers to a detectable marker or reporter molecules, which can be attached to nucleic acids. Typical labels include fluorophores, radioactive isotopes, ligands, chemiluminescent agents, metal sols and colloids, and enzymes. Methods for labeling and guidance in the choice of labels useful for various purposes are discussed, e.g., in Sambrook et al., in *Molecular Cloning: A Laboratory Manual*, Cold Spring Harbor Laboratory Press (1989) and Ausubel et al., in *Current Protocols in Molecular Biology*, Greene Publishing Associates and Wiley-Intersciences (1987).

As used herein, the term "about", in the context of concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

Unless the context requires otherwise or specifically stated to the contrary, integers, steps, or elements of the invention recited herein as singular integers, steps or elements clearly encompass both singular and plural forms of the recited integers, steps or elements.

The word "substantially" does not exclude "completely" e.g. a composition which is "substantially free" from Y may be completely free from Y. Where necessary, the word "substantially" may be omitted from the definition of the invention.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

BRIEF DESCRIPTION OF THE DRAWINGS

The invention will be better understood with reference to the detailed description when considered in conjunction with the non-limiting examples and the accompanying drawings, in which FIGS. 1A, 1B, and 1C: Antibody heavy and light chain sequences and isotype of mAb C51. FIG. 1A shows the nucleotide sequence of mAb C51. FIG. 1B shows the amino acid sequence of mAb C51. FIG. 1C shows the isotype of mAb C51 as identified from supernatant of mouse hybridoma culture expressing mAb C51 using the IsoStrip Mouse Monoclonal Antibody Isotyping Kit (Roche). Antibody Complementarity-Determining Regions are underlined.

FIGS. 2A and 2B: Reactivity of mAb C51 to Various Types of Cancer and Normal Cell Lines. FIG. 2A shows the heat map of C51 binding to various cancer cell lines. Reactivity was graded 0-4 based on percentage of mAb C51 binding to various cell populations via flow cytometry. FIG. 2B shows a Ttable of C51 binding to ovarian and breast cancer cell lines according to a classification based on the Epithelial-Mesenchymal Transition (EMT).

FIG. 3A shows immunoprecipitation (IP) with mAb C51 and a commercially available α-ANXA2 mAb were cross-probed using Western Blot analysis. Similar antigen bands appeared around 39 kDA. FIG. 3B shows that ANXA2 siRNA was used to knockdown ANXA2 in IGROV1 cells. Western Blot analysis was performed to evaluate loss of mAb C51 binding to ANXA2-knockdown cell lysate.

FIG. 4A shows treatment of the membrane fraction of MCF7 cells with PNGase-F showed loss of C51-binding to the 39-kDa band antigen band. FIG. 4B shows when cells were treated with tunicamycin and lysed. Western blot analysis showed a loss of the target antigen for C51.

FIGS. 10A, 10B, and 10C: Antibody heavy and light chain sequences and isotype of mAb 2448. FIG. 10A shows the nucleotide sequence of mAb 2448. FIG. 10B shows the amino acid sequence of mAb 2448. Antibody Complementarity-Determining Regions are underlined FIG. 10C shows the isotype of mAb 2448 as identified from supernatant of mouse hybridoma culture expressing mAb 2448 using the IsoStrip Mouse Monoclonal Antibody Isotyping Kit (Roche).

FIGS. 11A, 11B, and 11C: Reactivity of mAb 2448 to Various Types of Cancer and Normal Cell Lines. FIG. 11A shows a heat map of mAb 2448 binding to various cancer cell lines. Reactivity was graded 0-4 based on percentage of mAb 2448 binding to various cell populations via flow cytometry. FIG. 11B shows a table of mAb 2448 binding to ovarian and breast cancer cell lines according to a classification based on the Epithelial-Mesenchymal Transition (EMT). FIG. 11C shows isogenic breast cancer cell lines MCF7-D10 and MCF7-2101 displayed epithelial and mesenchymal phenotypes of EMT, respectively. Significantly higher levels of the epithelial marker E-Cadherin and lower levels of the mesenchymal marker Vimentin were expressed in MCF7 cells versus MCF72101 cells, respectively. Phase contrast microscopy images revealed EMT-like morphological changes. MCF7-D10 cells were more epithelial with cuboidal or "cobblestone-like" cells compared to MCF7-2101 cells which were more isolated and elongated. Membranous binding of 2448 was observed on MCF7-D10 cells but not on the isogenic MCF7-2101 cells by immunocytochemistry. mAb 2448 demonstrated binding (shaded histogram) on live MCF7-D10 cells, but not on MCF7-2101 cells by flow cytometry.

FIGS. 12A, 12B, and 12C: Validation of ANXA2 as the antigen target of mAb 2448. FIG. 12A shows immunoprecipitation from the membrane fraction of cell lysate (MF) using mAb 2448 coupled Protein G beads was identified by Western Blot analysis. FIG. 12B shows the corresponding band (↑) on a silver-stained gel was excised and sent for identification using liquid chromatography tandem-mass spectrometry (LC/MS-MS). After a protein database search using MS data, the potential target of ANXA2 was identified. FIG. 12C shows peptide matches (boxed) from multiple rounds of mass spectrometry spanned across the peptide sequence of ANXA2 (SEQ ID NO: 30).

FIG. 13A shows the Western blot analysis of antigen immunoprecipitated from human embryonic stem cells and the membrane fraction of T47D breast cancer cell lines using mAb 2448 coupled Protein G beads. FIG. 13B shows the corresponding band on a silver stained gel was excised and identified as ANXA2 using mass spectrometry analysis.

FIG. 14A shows immunoprecipitation (IP) using a commercially available α-annexin 2 (ANXA2) mAb and mAb 2448 were cross-probed using Western Blot analysis. Similar antigen bands appeared around 39 kDA. FIG. 14B shows that ANXA2 siRNA was used to knockdown ANXA2 in IGROV1 cells. Western Blot analysis was performed to evaluate loss of mAb 2448 binding to ANXA2-knockdown cells lysate.

FIG. 16A shows binding of mAb 2448 was sensitive to periodate treatment of Western Blot membranes run with IGROV1 lysate. (B) FIG. 16B shows treatment of the membrane fraction of cells with PNGase-F results in loss of 2448-binding to the 39-kDa band antigen band.

FIG. 18: ADC activity of mAb 2448, ch2448 and ch2448ATS. Cytotoxicity of antibodies (2448 and ch2448) in complex with secondary saporin conjugates (ZAP) was evaluated on ovarian and breast cancer cells. Antibody 2448 and ch2448 were pre-mixed with anti-mouse IgG (mAbZAP) or anti-human IgG (HZAP) saporin conjugates, respectively. Cancer cells were incubated with mixtures, primary mAb alone (2448 or ch2448), saporin conjugate alone (mAbZAP or HZAP) or buffer as a control. Post 72 h incubation, live cells were measured as a percentage of the control cells treated with buffer alone. Cytotoxicity was observed by a significant difference in live cells treated with mAbs in-complex with secondary conjugates compared to those treated with primary mAb or secondary conjugate alone. Results are represented as mean±standard deviation of three independent experiments with triplicate wells (*, P<0.05; , P<0.01; and *, P<0.001, unpaired t-test). T47D cells were tested once in quadruplicate wells.

FIG. 19A showscell proliferation of IGROV1 and IOSE523 cultures were monitored in real time with the xCELLigence System (Roche). Sustained inhibition of cell growth was observed on target IGROV1 cells but not on control IOSE2523 cells. FIG. 19B shows cytotoxicity of ch2448ATS was observed in a dose-dependent manner. Post 72 h, the half maximal inhibitory concentration was measured in IGROV1 and SKOV3 cultures.

FIG. 21A shows ch2448 suppressed IGROV1 tumor cell growth. Treatment of ch2448 (1 mg) or buffer vehicle control (↓) was administered via intraperitoneal injection.

FIG. 21B shows that no drastic weight loss was observed throughout treatment regime. All values and bars are represented as standard error of the mean (S.E.M.) Two-sided unpaired Student's t-test. *, , and * indicate p<0.05, 0.01 and 0.005.

FIGS. 22A, 22B, and 22C: In vitro and in vivo effects of ch2448-F(ab')2. FIG. 22A shows IdeS digestion was used to generate F(ab')2 fragments of ch2448. Digestion products were separated by SDS-PAGE and visualized with Coomassie Blue staining. FIG. 22B shows that after digestion, the loss of ADCC activity was observed compared to ch2448, in vitro. FIG. 22C shows that in vivo, F(ab'2) did not demonstrate any suppression of tumor growth.

FIG. 23A shows that similar binding profiles of afucosylated ch2448 and ch2448 was demonstrated by flow cytometry analysis. FIG. 23B shows afucosylated ch2448 exhibited enhanced (>10 fold) ADCC activity compared to the wild-type. ADCC activity was measured as fold induction of the NFAT ADCC pathway using an ADCC reporter bioassay (Promega). Compared to the original ch2448, to elicit the same ADCC effect, the concentration of afucosylated ch2448 required is more than 100× less.

FIG. 24A shows mAb 2448 was raised against hESC and specifically binds to hESC but not differentiated embryoid bodies (EB). FIG. 24B shows as a naked antibody, mAb 2448 is able to prevent the formation of teratoma in vivo.

FIG. 25A shows ch2448 internalizes into undifferentiated hESC as observed in the pH-Rodo assay but not into differentiated cells ch2448 can potentially be used as an ADC to specifically eliminate undifferentiated hESC.

FIG. 25B shows as an ADC, ch2448 kills undifferentiated hESC in vitro but does not kill differentiated EBs. ch2448 can potentially be used as an ADC to specifically eliminate undifferentiated hESC in regenerative therapy. FIG. 25C shows F(ab')2 ch2448 can also be used as an ADC to specifically eliminate undifferentiated hESC in vitro.

FIGS. 26A and 26B. The ability of ch2448 to prevent or delay teratoma formation. FIG. 26A shows single-cell suspension of human embryonic stem cells ($5 \times 10^6$ cells per animal) were pre-incubated with either buffer (upper figure) or the ADC at 4° C. for 20 minutes (lower figure) and then injected into the right hind leg muscle of SCID mice (n=3). Teratoma formation was then evaluated with a grading method developed previously. FIG. 26B shows single-cell suspension of human embryonic stem cells ($5 \times 10^6$ cells per animal) were injected into the right hind leg muscle of SCID mice (n=3). Buffer (upper figure) and ADC (lower figure) were administered intra-peritoneal. Teratoma formation was then evaluated with a grading method developed previously.

DETAILED DESCRIPTION OF THE PRESENT INVENTION

Figure 3A:
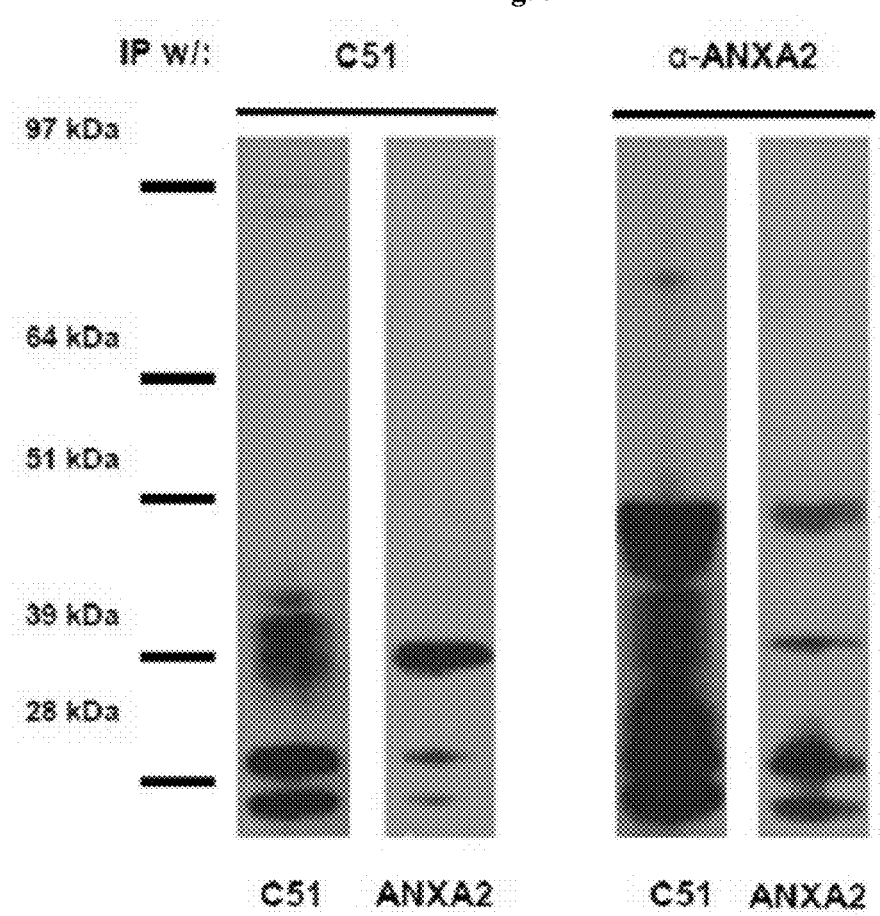
FIGS. 3A and 3B: Validation of ANXA2 as the antigen target of mAb C51.

In a first aspect, there is provided an antigen-binding protein, or an antigen-binding fragment thereof. The antigen-binding protein, or an antigen-binding fragment thereof comprises (i) a heavy chain variable domain comprising a VHCDR1 having the amino acid sequence GYSITSGYSWH (SEQ ID NO: 9); a VHCDR2 having the amino acid sequence YIHYSGSTKYNPSLKS (SEQ ID NO: 10) and a VHCDR3 having the amino acid sequence GSNYGFDY (SEQ ID NO: 11); and (ii) a light chain variable domain comprising a VLCDR1 having the amino acid sequence KSSQSLLYSNDQKNYLA (SEQ ID NO: 12), a VLCDR2 having the amino acid sequence WASIRES (SEQ ID NO: 13), and a VLCDR3 having the amino acid sequence QQYYIYPLT (SEQ ID NO: 14).

The antigen-binding protein, or antigen-binding fragment thereof, may comprise heavy and light chain CDR regions that are about 80%, about 85%, about 90%, about 95%, about 96%, about 97%, about 98% or about 99% identical to the heavy and light chain CDR regions of (i) and (ii).

In one embodiment, the heavy chain variable region comprises the amino acid sequence set forth in SEQ ID NO:1. Alternatively, the heavy chain variable region may comprise an amino acid sequence having about 80%, about 85%, about 90%, about 95%, about 96%, about 97%, about 98% or about 99% identity to the amino acid sequence set forth in SEQ ID NO:1.

In one embodiment, the light chain variable region may comprise the amino acid sequence set forth in SEQ ID NO:2. Alternatively, the light chain variable region may comprise an amino acid sequence having about 80%, about 85%, about 90%, about 95%, about 96%, about 97%, about 98% or about 99% identity to the amino acid sequence set forth in SEQ ID NO:2.

In another aspect, there is provided an antigen-binding protein, or an antigen-binding fragment thereof, comprising (i) a heavy chain variable domain comprising a VHCDR1 having the nucleic acid sequence GCTACTCCATCACCAGTGGTTATAGCTGGCAC (SEQ ID NO: 15); a VHCDR2 having the nucleic acid sequence ACATACACTACAGTGGTAGCACTAAGTACAACCCATCTCTCAAAAGTC (SEQ ID NO: 16), and a VHCDR3 having the nucleic acid sequence GGAGTAACTACGGATTTGACTACT (SEQ ID NO: 17); and (ii) a light chain variable domain comprising a VLCDR1 having the nucleic acid sequence AGTCCAGTCAGAGCCTTTTATATAGTAACGATCAAAAGAACTACTTGGCCT (SEQ ID NO: 18), a VLCDR2 having the nucleic acid sequence GGGCATCTATTAGGGAATCTG (SEQ ID NO: 19), and a VLCDR3 having the nucleic acid sequence AGCAATATTATATCTATCCTCTCACGT (SEQ ID NO: 20).

In one embodiment, the antigen-binding protein, or antigen-binding fragment thereof, may comprise heavy and light chain CDR regions that are about 60%, 65%, 70%, 75%, 80%, about 85%, about 90%, about 95%, about 96%, about 97%, about 98% or about 99% identical to the heavy and light chain CDR regions of (i) and (ii).

In one embodiment, the heavy chain variable region may comprise the nucleic acid sequence set forth in SEQ ID NO:3. Alternatively, the antigen-binding protein, or antigen-binding fragment thereof, may comprise a heavy chain variable region which comprises a nucleic acid sequence having about 60%, 65%, 70%, 75%, 80%, about 85%, about 90%, about 95%, about 96%, about 97%, about 98% or about 99% identity to the nucleic acid sequence set forth in SEQ ID NO:3.

In one embodiment, the light chain variable region may comprise the nucleic acid sequence set forth in SEQ ID NO:4. Alternatively, the antigen-binding protein, or antigen-binding fragment thereof, may comprise a light chain variable region which comprises a nucleic acid sequence having about 60%, 65%, 70%, 75%, 80%, about 85%, about 90%, about 95%, about 96%, about 97%, about 98% or about 99% identity to the amino acid sequence set forth in SEQ ID NO:4.

In one embodiment the antigen-binding protein, or antigen-binding fragment thereof, may be selected from the group consisting of monoclonal, recombinant, polyclonal, chimeric, humanised, bispecific and heteroconjugate antibodies; a chimeric antigen receptor (CAR), a single variable domain, a domain antibody, antigen binding fragments, immunologically effective fragments, single chain Fv, a single chain antibody, a univalent antibody lacking a hinge region, a minibody, diabodies, and Tandabs™.

In one embodiment, the binding protein may be a monoclonal antibody. The monoclonal antibody may be 2448. In one embodiment, the monoclonal antibody may be humanised. Alternatively, the monoclonal antibody may be chimeric.

The monoclonal antibody may be defucosylated. The degree of fucosylation is may be less than 10%, less than 5%, or less than 1.5% relative to the wild-type antibody.

In another aspect there is provided an antigen-binding protein, or an antigen-binding fragment thereof, comprising (i) a heavy chain variable domain comprising a VHCDR1 having the amino acid sequence VYSITSGYSWH (SEQ ID NO: 21); a VHCDR2 having the amino acid sequence YIHYSGSTKYNPSLKS (SEQ ID NO: 10), and a VHCDR3 having the amino acid sequence GTDNAVDY (SEQ ID NO: 22); and (ii) a light chain variable domain comprising a VLCDR1 having the amino acid sequence KSSQSLLYSSNQKNYLA (SEQ ID NO: 23), a VLCDR2 having the amino acid sequence WASSRES (SEQ ID NO: 24), and a VLCDR3 having the amino acid sequence QQYYIYPLT (SEQ ID NO: 14).

In one embodiment, the antigen-binding protein, or antigen-binding fragment thereof, may comprise heavy and light chain CDR regions that are about 80%, about 85%, about 90%, about 95%, about 96%, about 97%, about 98% or about 99% identical to the heavy and light chain CDR regions of (i) and (ii).

In one embodiment, the heavy chain variable region may comprise the amino acid sequence set forth in SEQ ID NO:5. Alternatively, the heavy chain variable region may comprise an amino acid sequence having about 80%, about 85%, about 90%, about 95%, about 96%, about 97%, about 98% or about 99% identity to the amino acid sequence set forth in SEQ ID NO:5.

In one embodiment, the light chain variable region may comprise the amino acid sequence set forth in SEQ ID NO:6. Alternatively, the antigen-binding protein, or antigen-binding fragment thereof, may comprise a light chain variable region which comprises an amino acid sequence having about 80%, about 85%, about 90%, about 95%, about 96%, about 97%, about 98% or about 99% identity to the amino acid sequence set forth in SEQ ID NO:6.

In another aspect, there is provided an antigen-binding protein, or an antigen-binding fragment thereof, comprising (i) a heavy chain variable domain comprising a VHCDR1 having the nucleic acid sequence TCTACTCCAT-CACCAGTGGTTATAGCTGGCACT (SEQ ID NO: 25); a VHCDR2 having the nucleic acid sequence ACATACAC-TACAGTGGTAGTACTAAGTACAACCCATCTC-TCAAAAGTC (SEQ ID NO: 26), and a VHCDR3 having the nucleic acid sequence GGACCGACAATGCTGTGGAC-TACT (SEQ ID NO: 27); and (ii) a light chain variable domain comprising a VLCDR1 having the nucleic acid sequence AGTCCAGTCAGAGCCTTT-TATATAGTAGCAATCAAAAGAACTACTTGGCCT (SEQ ID NO: 28), a VLCDR2 having the nucleic acid sequence GGGCATCCAGTAGGGAATCTG (SEQ ID NO: 29), and a VLCDR3 having the nucleic acid sequence AGCAATATTATATCTATCCTCTCACGT (SEQ ID NO: 20).

The antigen-binding protein, or antigen-binding fragment thereof, may comprise heavy and light chain CDR regions that are about 60%, 65%, 70%, 75%, 80%, about 85%, about 90%, about 95%, about 96%, about 97%, about 98% or about 99% identical to the heavy and light chain CDR regions of (i) and (ii).

The heavy chain variable region may comprise the nucleic acid sequence set forth in SEQ ID NO:7. The heavy chain variable region may comprise a nucleic acid sequence having about 60%, 65%, 70%, 75%, 80%, about 85%, about 90%, about 95%, about 96%, about 97%, about 98% or about 99% identity to the nucleic acid sequence set forth in SEQ ID NO:7.

The light chain variable region may comprise the nucleic acid sequence set forth in SEQ ID NO:8. The antigen-binding protein, or antigen-binding fragment thereof, may comprise a light chain variable region which comprises a nucleic acid sequence having about 60%, 65%, 70%, 75%, 80%, about 85%, about 90%, about 95%, about 96%, about 97%, about 98% or about 99% identity to the amino acid sequence set forth in SEQ ID NO:8.

In one embodiment, the antigen binding protein may be selected from the group consisting of monoclonal, recombinant, polyclonal, chimeric, humanised, bispecific and heteroconjugate antibodies; a chimeric antigen receptor (CAR), a single variable domain, a domain antibody, antigen binding fragments, immunologically effective fragments, single chain Fv, a single chain antibody, a univalent antibody lacking a hinge region, a minibody, diabodies, and Tandabs™.

In one embodiment, the binding protein may be a monoclonal antibody. The monoclonal antibody may be C51. The monoclonal antibody may be humanised. Alternatively, the monoclonal antibody may be chimeric.

In one embodiment, the antigen-binding protein, or antigen-binding fragment thereof, as described herein, may bind to ANXA2. In one embodiment, the antigen-binding protein, or antigen-binding fragment thereof, as described herein, may bind to a glycan on ANXA2. The antigen-binding protein, or an antigen-binding fragment thereof, as described herein, may bind to an N-linked glycan on ANXA2. The N-linked glycan may be located at amino acid residue 62 of ANXA2.

In another embodiment, the antigen-binding protein, or antigen-binding fragment thereof, as described herein, may comprise a radioisotope or a cytotoxin conjugated thereto. The antibody may be conjugated with a cytotoxin selected from the group consisting of monomethyl auristatin E (MMAE-1), mertansine (DM-1) and saporin.

In one embodiment, the antigen-binding protein, or an antigen-binding fragment, as described herein, may be internalized into a cell upon binding to ANXA2.

In one embodiment, the antigen-binding protein, or an antigen-binding fragment thereof, as described herein, may have a cytotoxic activity selected from one or more of the group consisting of complement dependent cytotoxic (CDC) activity, antibody dependent cellular cytotoxic (ADCC) activity and oncolytic activity.

In another aspect, there is provided a composition comprising a physiologically acceptable carrier and a therapeutically effective amount of the antigen-binding protein, or an antigen-binding fragment thereof, as described herein.

In one embodiment, the composition may comprise a further active pharmaceutical ingredient selected from the group consisting of bevacizumab, carboplatin, paclitaxel or gefitinib.

The percentage of the antigen-binding protein, or an antigen-binding fragment thereof, as described herein, in pharmaceutical compositions and preparations may, of course, be varied and, for example, may conveniently range from about 2% to about 90%, about 5% to about 80%, about 10% to about 75%, about 15% to about 65%; about 20% to about 60%, about 25% to about 50%, about 30% to about 45%, or about 35% to about 45%, of the weight of the dosage unit. The amount of compound in therapeutically useful compositions is such that a suitable dosage will be obtained.

The language "physiologically acceptable carrier" is intended to include solvents, dispersion media, coatings, anti-bacterial and anti-fungal agents, isotonic and absorption delaying agents, and the like. The use of such media and agents for pharmaceutically active substances is well known in the art. Except insofar as any conventional media or agent is incompatible with the compound, use thereof in the therapeutic compositions and methods of treatment and prophylaxis is contemplated. Supplementary active compounds may also be incorporated into the compositions according to the present invention. It is especially advantageous to formulate parenteral compositions in dosage unit form for ease of administration and uniformity of dosage. "Dosage unit form" as used herein refers to physically discrete units suited as unitary dosages for the individual to be treated; each unit containing a predetermined quantity of compound(s) is calculated to produce the desired therapeutic effect in association with the required pharmaceutical carrier. The compound(s) may be formulated for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

The composition may be conveniently administered by injection, for example, subcutaneous, intravenous, and the like. The composition may also be administered parenterally or intraperitoneally. In one embodiment, the compound may be administered by injection. In the case of injectable solutions, the carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by including various anti-bacterial and/or anti-fungal agents. Suitable agents are well known to those skilled in the art and include, for example, parabens, chlorobutanol, phenol, benzyl alcohol, ascorbic acid, thimerosal, and the like. In many cases, it may be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminium monostearate and gelatin.

Sterile injectable solutions can be prepared by incorporating the analogue in the required amount in an appropriate solvent with one or a combination of ingredients enumerated above, as required, followed by filtered sterilisation. Generally, dispersions are prepared by incorporating the analogue into a sterile vehicle which contains a basic dispersion medium and the required other ingredients from those enumerated above.

Under ordinary conditions of storage and use, pharmaceutical preparations may contain a preservative to prevent the growth of microorganisms. Preferably, the pharmaceutical composition may further include a suitable buffer to minimise acid hydrolysis. Suitable buffer agent agents are well known to those skilled in the art and include, but are not limited to, phosphates, citrates, carbonates and mixtures thereof.

Single or multiple administrations of the pharmaceutical compositions according to the invention may be carried out. One skilled in the art would be able, by routine experimentation, to determine effective, non-toxic dosage levels of the compound and/or composition of the invention and an administration pattern which would be suitable for treating the diseases and/or infections to which the compounds and compositions are applicable.

Further, it will be apparent to one of ordinary skill in the art that the optimal course of treatment, such as the number of doses of the compound or composition of the invention given per day for a defined number of days, can be ascertained using convention course of treatment determination tests.

Generally, an effective dosage per 24 hours may be in the range of about 0.0001 mg to about 1000 mg per kg body weight; suitably, about 0.001 mg to about 750 mg per kg body weight; about 0.01 mg to about 500 mg per kg body weight; about 0.1 mg to about 500 mg per kg body weight; about 0.1 mg to about 250 mg per kg body weight; or about 1.0 mg to about 250 mg per kg body weight. More suitably, an effective dosage per 24 hours may be in the range of about 1.0 mg to about 200 mg per kg body weight; about 1.0 mg to about 100 mg per kg body weight; about 1.0 mg to about 50 mg per kg body weight; about 1.0 mg to about 25 mg per kg body weight; about 5.0 mg to about 50 mg per kg body weight; about 5.0 mg to about 20 mg per kg body weight; or about 5.0 mg to about 15 mg per kg body weight.

Alternatively, an effective dosage may be up to about 500 mg/m$^2$. For example, generally, an effective dosage is expected to be in the range of about 25 to about 500 mg/m$^2$, about 25 to about 350 mg/m$^2$, about 25 to about 300 mg/m$^2$, about 25 to about 250 mg/m$^2$, about 50 to about 250 mg/m$^2$, and about 75 to about 150 mg/m$^2$.

In another aspect, there is provided use of an antigen-binding protein, or an antigen-binding fragment thereof, as described herein, in the manufacture of a medicament for treating or preventing cancer.

In one embodiment, the cancer may be selected from the group consisting of breast cancer, liver cancer, kidney cancer, colorectal cancer, ovarian cancer and teratoma.

In some embodiments the medicament may be administered with a further active pharmaceutical ingredient. Alternatively, the medicament may be administered with chemotherapy. The further pharmaceutical agent or chemotherapy may be administered separately, simultaneously or sequentially.

In another aspect, there is provided a method for detecting cancer in a subject, the method comprising: contacting a sample obtained from the subject with an antigen-binding protein, or an antigen-binding fragment thereof as described herein in vitro; detecting the binding of the antigen-binding protein, or an antigen-binding fragment thereof in the sample; correlating the binding with a level of binding in a control sample to determine the level of binding in the sample, wherein an increase in the level of binding in the sample relative to the control sample is indicative of cancer.

In another aspect, there is provided a method for identifying a subject susceptible to cancer the method comprising: contacting a sample obtained from the subject with an antigen-binding protein, or an antigen-binding fragment thereof as described herein in vitro; detecting the binding of the antigen-binding protein, or an antigen-binding fragment thereof in the sample; correlating the binding with a level of binding in a control sample to determine the level of binding in the sample, wherein an increase in the level of binding in the sample relative to the control sample indicates that the subject is susceptible to cancer.

In one embodiment, the control sample may be from the same subject. Alternatively, the control sample may be from a different subject.

In one embodiment, the antigen-binding protein, or antigen-binding fragment thereof as described herein may comprise a detectable label. The detectable label may be selected from the group consisting of a fluorescent label, a chemiluminescent label, an enzymatic label and a radionuclide label. In one embodiment, the detectable label is selected from the group consisting of biotin, alkaline phosphatase, horseradish peroxidase, FITC, PE and Cy Dyes. The detectable label may be detected in an assay selected from flow cytometry, tissue section, immunofluorescence, immunocytochemistry or immunohistochemistry.

In one aspect, there is provided a kit when used in the method as described herein, comprising an antigen-binding protein, or antigen-binding fragment thereof as described herein, together with instructions for use.

EXAMPLES

Non-limiting examples of the invention, including the best mode, and a comparative example will be further described in greater detail by reference to specific Examples, which should not be construed as in any way limiting the scope of the invention.

Materials and Methods

Antibody Generation and Purification

Monoclonals 2448 and C51 were generated by whole-cell immunization of human embryonic stem cells (HES-3) using mouse hybridoma technology as reported in Choo et al. (Choo A B, Tan H L, Ang S N, Fong W J, Chin A, Lo J, et al. Selection against undifferentiated human embryonic stem cells by a cytotoxic antibody recognizing podocalyxin-like protein-1. Stem Cells Dayt Ohio. 2008; 26:1454-63). Hybridomas were maintained in ClonaCell™-HY Medium E (Stem Cells Technologies) at 37° C. in a humidified incubator with 5% $CO_2$. Chimeric (including afucosylated) antibodies were expressed in DG44-CHO cells and maintained in BTI's proprietary serum-free media. Chimerisation was done by the Animal Cell Technology group at the Bioprocessing Technology Institute (Ho S C L, Bardor M, Feng H, Mariati null, Tong Y W, Song Z, et al. IRES-mediated Tricistronic vectors for enhancing generation of high monoclonal antibody expressing CHO cell lines. J Biotechnol. 2012; 157:130-9).

Purification was done using the AKTA Explorer 100 (GE Healthcare) system. Cultured supernatants were subjected to Protein A chromatography (Tosoh; Toyopearl AF-rProtein A-650F) and ion exchange chromatography (Biorad; UNO-sphere™ Q). Purified products were evaluated on a Superdex200 PC 3.2/30 column (GE Healthcare) using a high performance liquid chromatography system (Shimadzu). Antibodies were additionally analyzed by SDS-PAGE, and protein concentrations were determined by absorbance at $A_{280}$ using Nanodrop 1000 (Thermo Fisher Scientific). For in vivo studies, endotoxin was measured to ensure levels were below 0.1 EU/mL using the Endosafe® Endotoxin Testing System (Charles River).

Flow Cytometry and Analysis

Cells were harvested as single-cell suspensions using trypsin (Thermo Fisher Scientific). Each sample of $1-2 \times 10^5$ cells was thoroughly washed in 1% bovine serum albumin (BSA; Sigma Aldrich) in phosphate buffered saline (PBS) buffer (Thermo Fisher Scientific) Samples were incubated with primary antibody at 4° C. for 45 min, washed and then incubated with the appropriate fluorophore-conjugated secondary antibody (fluorescein isothiocyanate (FITC)-labeled goat anti-human kappa light chain mAbs (Sigma Aldrich) or FITC-labeled goat anti-mouse Ig polyclonal (Dako), for 15 min at 4° C. After incubation, cells were washed and sample data acquisition was done by on a BD FACSCalibur™ (BD Biosciences) or Guava® easyCyte (Millipore). Data analysis was done using FlowJo™ software v7.6.3 (Tree Star). Percentage of binding was determined using M-gating set at the 97th-98th-percentile based on the negative control.

Immunocytochemistry

Cell cultures were fixed with 4% paraformaldehyde for 20 min. For permeabilized cells, 0.1% Triton X-100/PBS (Bio-Rad) was added for 3×5 min, and finally blocked with either 10% goat serum/PBS (DAKO) for 1 h at room temperature. Cells were incubated at 4° C. with 2448 conjugated with DyLight™ 488 NHS Ester (Thermo Fisher Scientific). DNA was counterstained with DAPI (1:1000, Thermo Fisher Scientific). Images were taken using a Zeiss Axiovert 200 inverted microscope.

Gel Electrophoresis and Western Blot Analysis

Cells were harvested by manual scraping and as required, enriched for membrane proteins via the Membrane Protein Extraction Kit (BioVision) as per the manufacturer's instructions. Briefly, cells were re-suspended in homogenization buffer and centrifuged at 700 g for 10 min at 4° C. Supernatant was then aspirated and centrifuged at 10,000 g for 30 min at 4° C. Cell pellet of total membrane proteins was collected and lysed. Buffer for lysis contained 2% Triton X-100 (Bio-Rad) in PBS which was supplemented with protease inhibitors (Calbiochem) as needed. Total protein concentration was determined using the DC™ Protein Assay (Bio-Rad).

For gel electrophoresis, samples were prepared with loading dye at a final concentration of 50 mM Tris-HCl, 2% SDS, 10% glycerol, 0.02% bromophenol blue and for reducing conditions, 2-5% beta-mercaptoethanol. Samples along with SeeBlue Plus2® or Page2™ protein standards (Thermo Fisher Scientific) were subjugated to sodium dodecyl sulfate polyacrylamide gel electrophoresis (SDS-PAGE) using a 4-12% Bis-Tris gradient gel (Thermo Fisher Scientific) and 1× MOPS buffer (Thermo Fisher Scientific). If needed, Gels were stained using Coomasie Brilliant Blue or SilverQuest™ Silver Staining Kit)

For Western blot, products from gel run were transferred to polyvinylidene difluoride (PVDF) membranes (Bio-Rad) and blocked with 5% non-fat milk or Odyssey® Blocking Buffer (LI-COR) for 1 h. Incubation with primary mAb (mouse anti-annexin A2 mAb (BD Biosciences); mouse anti-annexin A2 mAb (Invitrogen); rabbit anti-annexin A2 pAb (Santa Cruz); mouse anti-E-Cadherin mAb (BD Biosciences); mouse monoclonal anti-Vimentin (Dako); mouse anti-human Fc-specific antibody (Sigma)) or biotinylated lectin (Aleuria Aurantia Lectin (Vector Labs)) was done overnight at 4° C. The blot was incubated for 1-2 h with an appropriate detection antibody (horseradish peroxidase (HRP)-conjugated goat anti-mouse Ig pAb, Dako) or streptavidin conjugated to horseradish peroxidase (Dako), and visualized upon addition of chemiluminescence substrate (GE Healthcare). Images were captured either on Medical X-ray Processor 2000 (Kodak) or the ChemiDoc™ Imaging System (Bio-Rad). Densitometry was done using Image Lab™ 5.2 software (BioRad) and normalized to beta-actin expression levels (Cell Signaling Technology).

Transient Knockdown of Annexin A2 (ANXA2)

IGROV1 cells were seeded on 6-well plates at $3 \times 10^5$ cells or T175 flasks at $1 \times 10^6$ cells and grown to 30 to 50% confluency. Transfection of a validated set of human annexin A2-specific siRNA (Thermo Fisher Scientific) and scramble siRNA control (Thermo Fisher Scientific) respectively both at concentration of 30 pM using Lipofectamine RNAiMAX (Thermo Fisher Scientific) in serum-free media. Post 5 h incubation at 37° C., transfection media was removed and replaced with fresh media containing 10% serum. Cells were harvested within 72 h for western blot analysis. Densitometry was done using IMageJ software (National Institutes of Health) and normalized using beta-actin (Cell Signaling Technology) expression levels.

Periodate Treatment

Lysate from IGROV1 cells was separated by SDS-PAGE and transferred to PVDF membranes (Bio-Rad). Subsequently, blots were washed twice with sodium acetate buffer (100 mM at pH 4.5; Merck Millipore), and incubated with sodium meta-periodate (100 mM, Sigma-Aldrich) for 30 min in the dark. Blots were subsequently washed four times with sodium acetate buffer, a PBS wash and quenched with 0.5 M of sodium borohydride (Sigma) for 30 min. Prior to incubation with primary antibodies, blots were blocked with Odyssey® Blocking Buffer (LI-COR) for 30 min. Control blots were similarly incubated with buffers but without the addition of sodium meta-periodate. Samples were analyzed using primary antibodies 2448, C51 and anti-beta-actin as a negative control.

Release of Glycans by PNGase-F and Beta-Elimination

For PNGase-F treatment, membrane protein enriched lysate (10 μg) was first denatured using 1 μl of 10× glycoprotein denaturing buffer (5% SDS without DTT) and water to make up a 10 μl reaction volume. Glycoproteins were heated to 100° C. for 5 min. A total reaction volume of 20 μl was prepared with the denatured glycoproteins by adding 2 μl of 10× G7 reaction buffer, 2 μl of 10% NP40, and 1 μl of PNGase F, and 5 μl of water. Samples were incubated in the reaction buffer for 1 h at 37° C. After incubation, samples were subjected to SDS-PAGE and western blot analysis. For alkaline beta-elimination treatment, western blots were incubated in 0.1 M sodium hydroxide solution at 60° C. overnight. The following day blots were subjected to western blot analysis.

Inhibition of Glycosylation by Tunicamycin

Inhibition of glycosylation was done in cell culture using tunicamycin, a nucleoside antibiotic that targets GlcNAc transferases. At high concentrations, tunicamycin can induce apoptosis in cancer cells however at lower concentrations, it can be used to inhibit synthesis of N-glycan in (eukaryotic) cells (127-129). IGROV1 cells at 60-70% confluency were treated with tunicamycin (Sigma-Aldrich) at a final concentration of 0.25 μg/mL. After 24 h incubation, cells harvested and analyzed by flow cytometry and western blot analysis.

Competitive Inhibition Assay

IGROV1 cells were incubated at saturating concentrations of a single antibody (2448 or ch2448) added alone, both antibodies added simultaneously and one mAb added after the other. Incubations were done for at least 15 min each at 4° C. and washed in 1% BSA/PBS. Secondary incubation was done using fluorophore conjugated secondary antibodies (Alexa fluor 647-conjugated anti-human pAb (Thermo Fisher Scientific) and Alexa Fluor 488-conjugated anti-mouse pAb (Thermo Fisher Scientific)). Binding was analyzed on a BD FACSCalibur flow cytometer (BD Biosciences) or Guava® easyCyte (Millipore).

Real-Time Monitoring of 2448-Saporin Cytotoxicity on Cell Growth

Cell growth was continuously cells was determined when cells treated at the lowest concentration were reaching a monitored over time by cell impedance measurements using the xCelligence® real-time cell analyzer (Roche) (130). Briefly, cell culture media was first loaded onto the 96-well E-plate to measure background impedance. IGROV1, IOSE523 and Sfilm.

V3 cells were plated at 1,000 cells per well and allowed to grow overnight in normal cell culture conditions. Cells were treated with antibody (ch2448) or antibody conjugates (ch2448-saporin or human IgG-saporin) at the beginning of the log phase of cell growth. Control wells were treated with buffer alone. All experiments were done in at least 5 wells per treatment condition. The outermost wells of the plate were not used. For dose response curves, IGROV1 were treated with dilutions of ch2448-saporin. The cells were monitored for growth until cells reached a death phase. Cell indices of wells were normalized after antibody treatment. The IC50 value on IGROV1 stationary phase of cell growth. The $IC_{50}$ value was calculated using the accompanying real-time cell analysis software (Roche).

Antibody Drug Conjugate (ADC) Assay with Secondary Saporin Conjugates

Cells were seeded in 96-well culture plates (Corning) at 1000 or 2000 cells per well as determined by growth curve. Primary antibody (2448, C51, ch2448 or chC51) at 10 μg/ml were complexed with appropriate secondary saporin conjugates: mAb-ZAP, Anti-M-ZAP, HUM-ZAP (Advanced Targeting Systems), at a 1:3 molar ratio for 15 min at room temperature. The pre-mixed complexes, the primary mAb, the secondary conjugate and buffer control were added to wells 24 h post-seeding. At 72 h post-treatment, viable (metabolically active) cells were measured based on the presence of ATP, using the CellTiter-Glo® Luminescent Cell Viability Assay kit (Promega). Data are expressed as the viability of treated cells as the percentage of the control cells treated with buffer alone.

Antibody Drug Conjugate (ADC) Assay with Ch2448-Saporin Conjugate

Direct conjugation of saporin to antibodies was outsourced to Advanced Targeting Systems (ATS). Drug to antibody molar ratios of ch2448-saporin, chTNA2-saporin and human Ig-saporin were 2.5, 2.9 and 3.1, respectively. Evaluation of the binding specificity was carried out by flow cytometry analysis as previously described.

Cytotoxicity of ch2448-saporin was evaluated on IGROV1, SKOV3 and IOSE523 cell lines. Cells were seeded in 96-well plates (Corning) at 1000 cells per well in 90 μl of media. The following day, ch2448-saporin and chTNA2-saporin were serially diluted and 10 μl of each dilution was added to wells. As a control, free saporin and ch2448 were added in a separate set of plates. Post 72 h incubation, the cell viability was measured using the CellTiter-Glo® Luminescent Cell Viability Assay kit (Promega) according to the manufacturer's instructions. Data are expressed as the % control, measuring the viability of treated cells with that of untreated cells. Dose response curves and $IC_{50}$ values were calculated using GraphPad Prism 6 (GraphPad).

Antibody-Dependent Cell-Mediated Cytotoxicity (ADCC) Assay

ADCC activity was measured using the ADCC Reporter Bioassay reporter bioassay (Promega) according to the manufacturer's protocol. Briefly, cells were seeded at 5,000 cells per well in a 96-well clear bottom black tissue culture plates (Corning) in low 4% IgG-serum (Promega) media. Serial dilutions of primary antibody were incubated in triplicate wells for approximately 15 min at 37° C., 5% CO2. Following incubation, engineered effector cells were added to the wells at approximately 150,000 cells per well. After 5 to 16 h (as indicated in results), Bio-Glo™ Luciferase Assay Substrate (Promega) was added to the wells and luminescence was measured using the Infinite® 200 microplate reader (Tecan). Estimated $EC_{50}$ values were calculated by on-linear regression on log-transformed data using GraphPad Prism 6 (GraphPad).

Tumor Xenograft Mouse Model

Four- to six-week-old female BALB/c nude mice (Invivos) were used in this study. On day 0, mice were inoculated with a total of $5 \times 10^6$ IGROV1 cells in 100 μl of cell media and high concentration matrigel (BD biosciences) at a 1:1 dilution volume. At 24 h post-inoculation, antibodies were injected intraperitoneally at 100 μl volumes of 1 mg per dose in 50 mM HEPES, 150 mM NaCl buffer. Subsequent administration was done weekly as indicated in results for 5 weeks. Size of the primary tumor was measured weekly by digital calipers. Tumor volumes (TV) were calculated based on the formula: TV=((L×L×W)/2), where W (width) and L (length) are the short and long diameter, respectively. A student's t-test was used to assess the statistical significance treated and untreated animals. For collection of tumors, animals were euthanized and immediately harvested for tumors. Samples were washed with PBS and either snap-frozen in liquid nitrogen or placed in paraformaldehyde (Merk) for 24 h which was subsequently replaced with 100% ethanol (Merk). Mice were euthanized when tumor size was >2000 mm$^3$ or when persistent side effects (e.g. swollen lymph nodes or drastic body weight loss) were observed over a period of more than two weeks. Euthanization was done by $CO_2$ inhalation followed by cervical dislocation. Animals were handled according to Biopolis IACUC Protocol No.: 151001 in accordance with the National Advisory Committee For Laboratory Animal Research (NACLAR) Guidelines.

Biodistribution Study

Female BALB/c nude mice were inoculated with a total of 5×10$^6$ IGROV1 cells in 100 µl of cell media and high concentration matrigel (BD biosciences) at a 1:1 dilution volume. When tumors reached 300-400 mm$^3$ (on week 10), dye-conjugated ch2448 and control conjugate chTNB1 were administered by i.p. injection at 100 µg per 100 µl of buffer (50 mM HEPES, 150 mM NaCl) per mouse. At 72 h and 94 h post injection, mice were anesthetized with 2-3% isoflurane and imaged using the IVIS® Spectrum imaging system (Caliper Life Sciences). Data was analyzed using the Living Image software 3.2 (Caliper Life Sciences).

Antibodies ch2448 and IgG control (Southern Biotech) were labelled with a near infrared fluorescent (NIR) dye CF750 using the XenoLight CF750 rapid antibody-labelling kit (Caliper Life Sciences) as per the manufacturer's instructions. Mice were handled according to Biopolis IACUC Protocol No.: 151001 in accordance with the National Advisory Committee For Laboratory Animal Research (NACLAR) Guidelines.

CAR Design and Vectors

CAR(2448) was designed in silico, and manufactured by GenScript. The CAR construct contained the GMCSFRa signal sequence, the anti-Annexin A2 $V_L$ and $V_H$ domains of the 2448 antibody connected via a Whitlow linker, the $IgG_4$ Fc linker region, the CD28 transmembrane and intracellular co-stimulatory domain, and the CD3ζ signalling domain. The CAR fragment was synthesised into the pcDNA3.1(+) plasmid, using HindIII and EcoRI restriction sites.

mRNA Production mRNA of the CAR constructs was in vitro transcribed utilising the HiScribe™ T7 ARCA mRNA Kit (with tailing) (New England BioLabs), according to the manufacturer's instructions. Briefly, CAR sequence plasmids were linearised utilising the XbaI restriction site, purified, and in vitro transcribed with ARCA capping. A subsequent poly(A) tailing reaction was conducted, before purification with lithium chloride. The final mRNA constructs were reconstituted in nuclease-free water, and stored at −80° C. in single-use aliquots.

Nucleofection of T Cells

T cells were isolated from human PBMCs using an EasySep human T cell isolation kit (StemCell Technologies). T cells were activated with Human T-Activator CD3/CD28 Dynabeads (Life Technologies) at a 1:1 bead:cell ratio. RPMI 1640, supplemented with 10% foetal calf serum (R10), and IL-7(20 U/mL), IL-15(10 U/mL), and IL-21(0.04 U/mL) was utilised as the T cell culture medium.

Prior to nucleofection, activating Dynabeads were removed, and T cells were resuspended in P3 Primary Cell Nucleofector™ Solution (Lonza) at 5×10$^4$ cells/µL. CAR mRNA (61 pg/µL) was added to the T cells, before nucleofection using program EO-115 of the 4D Nucleofector™ device. Cells were allowed to recover in R10 media at 37° C., 5% $CO_2$, with or without additional cytokine supplementation, depending on downstream application.

Cytotoxicity Assays

CAR-T cell cytotoxicity was assayed using the CytoTox 96® Non-Radioactive Cytotoxicity Assay (Promega), according to the manufacturer's instructions. Briefly, target IGROV-1 cells (1×10$^4$ cells/well) were co-incubated with effector CAR-T cells at varying effector:target ratios for 4 hours at 37° C., 5% $CO_2$. LDH release from lysed cells was detected using the kit solutions, and readout using an Infinite® M200 (TECAN).

For the cell growth assay, target IGROV-1 cells were seeded onto an E-plate 96 (ACEA Biosciences) at 1×10$^4$ cells per well. Cell growth was measured using the xCELLigence RCPA MP Instrument (ACEA Biosciences). After 24 hours, freshly nucleofected CAR-T cells were added into each well at 1:1, 2:1, 4:1, and 8:1 effector:target ratios. Cell growth was monitored for an additional 72 hours. No effector and no target cell wells were used as controls.

Cytokine Release Assay

CAR-T cells were incubated with target IGROV-1 cell at a 10:1 ratio for 6 hours at 37° C., 5% $CO_2$, without additional cytokine supplementation, before cytokine detection with the MACSPlex Cytokine 12 Kit (Miltenyi Biotec), according to the manufacturer's instructions. Briefly, cell supernatants were centrifuged and collected, before the addition of MPx Cytokine 12 Capture Beads. After a 2 hour incubation period at room temperature, capture beads were washed twice, and MPx Cytokine 12 Detection Reagent was added to detect bound cytokines. The beads were incubated for an additional hour at room temperature, before cytokine detection on the MACSQuant Analyzer 10 flow cytometer (Miltenyi Biotec).

Results

Antibody (Ab) heavy and light chain sequences and isotype of monoclonal antibody (mAb) C51 is an IgM-kappa.

Heavy and light chain gene sequences of mAb C51 were cloned from hybridoma cells by reverse transcription polymerase chain reaction (RT-PCR) and sequenced with complementarity-determining regions (CDRs) as underlined (FIGS. 1A and B). Isotyping of supernatant from hybridoma clone supernatant revealed that mAb C51 was an IgM-kappa immunoglobulin.

mAb C51 demonstrates reactivity to various cancers. mAb C51 binds to an epithelial phenotype according to a classification based on the Epithelial-Mesenchymal Transition (EMT).

High-throughput screening of mAb C51 was done on live cells by flow cytometry (FIG. 2A). Cell surface binding was observed on breast (BT474, BT20, CAMA1, HCC1937, HCC1954, HCC2218, MS578T, MCF7, MDAMB453, SKBR3, T47D), colorectal (COLO205, HT29, KM12, LS174T, SW620), kidney (786O, A498, ACHN, CAKI1, UO31, RXF393, TK10), liver (HEP3B, HEPG2, HUH7, PLC) and ovarian (CAOV3, IGROV1, OV90, OVCA432, OVCAR3, OVCAR8, OVCA433, PEA1, SKOV3) cancer cells. No binding was observed on normal cell lines (IMR90, IOSE523, HEK293, HFF, hTERT-HME1). Results showed that mAb C51 can specifically bind to multiple cancers. Binding of mAb C51 to ovarian and breast cancer cells was organized according to an Epithelial-Mesenchymal Transition (EMT) classification (FIG. 2B). mAb C51 was shown to preferentially bind to cells classified with an epithelial (E) and intermediate epithelial (IE) phenotype. Results showed that mAb C51 can potentially be used to monitor EMT.

Annexin A2 is the antigen target of mAb C51.

Figure 3B:
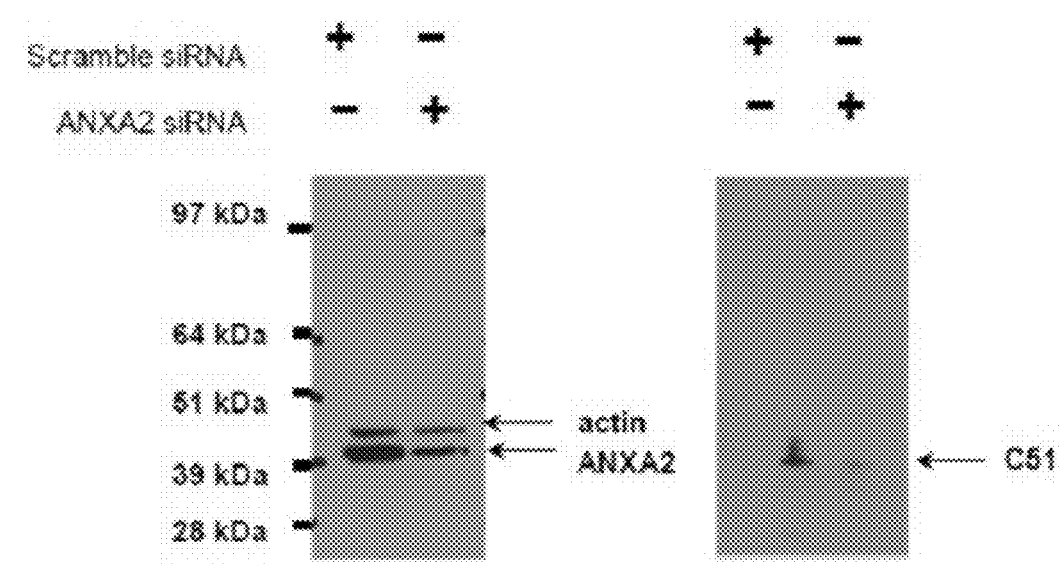

To validate ANXA2 as the antigen target of mAb C51, a forward and reverse-immunoprecipitation (IP) was carried out using a commercial anti-ANXA2 mAb. IP products were immunoblotted against mAb C51 and the commercial antibody (FIG. 3A). mAb C51 recognized similar antigen bands for both IP products. A transient siRNA knockdown study of ANXA2 was also carried out (FIG. 3B). Partial knockdown of ANXA2 corresponded to a loss of antigen recognition by mAb C51. Taken together, results demonstrated Annexin A2 as the antigen target of mAb C51.

mAb C51 targets an N-glycan epitope.

Figure 4A:
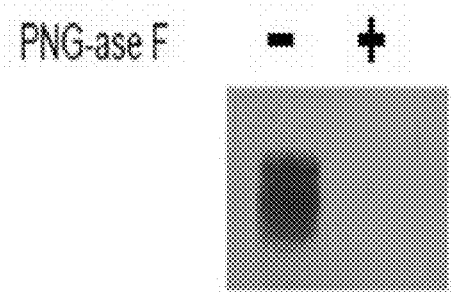
FIGS. 4A and 4B: Binding of mAb C51 to an N-glycan epitope.
Figure 4B:
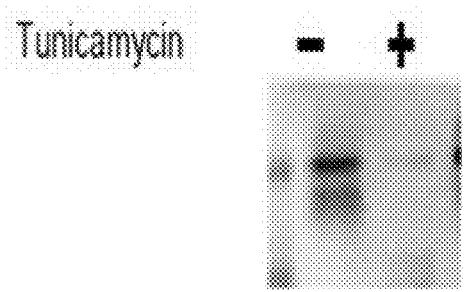

The binding of C51 was abolished when N-linked glycans were removed. This was demonstrated by both enzymatic digest of proteins with PNGase F treatment (FIG. 4A) and inhibition of N-linked glycosylation in cells with Tunicamycin (FIG. 4B). These results demonstrated that C51 was binding to N-glycan-epitope on ANXA2.

mAb C51 induces cell death via oncosis.

Figure 5:
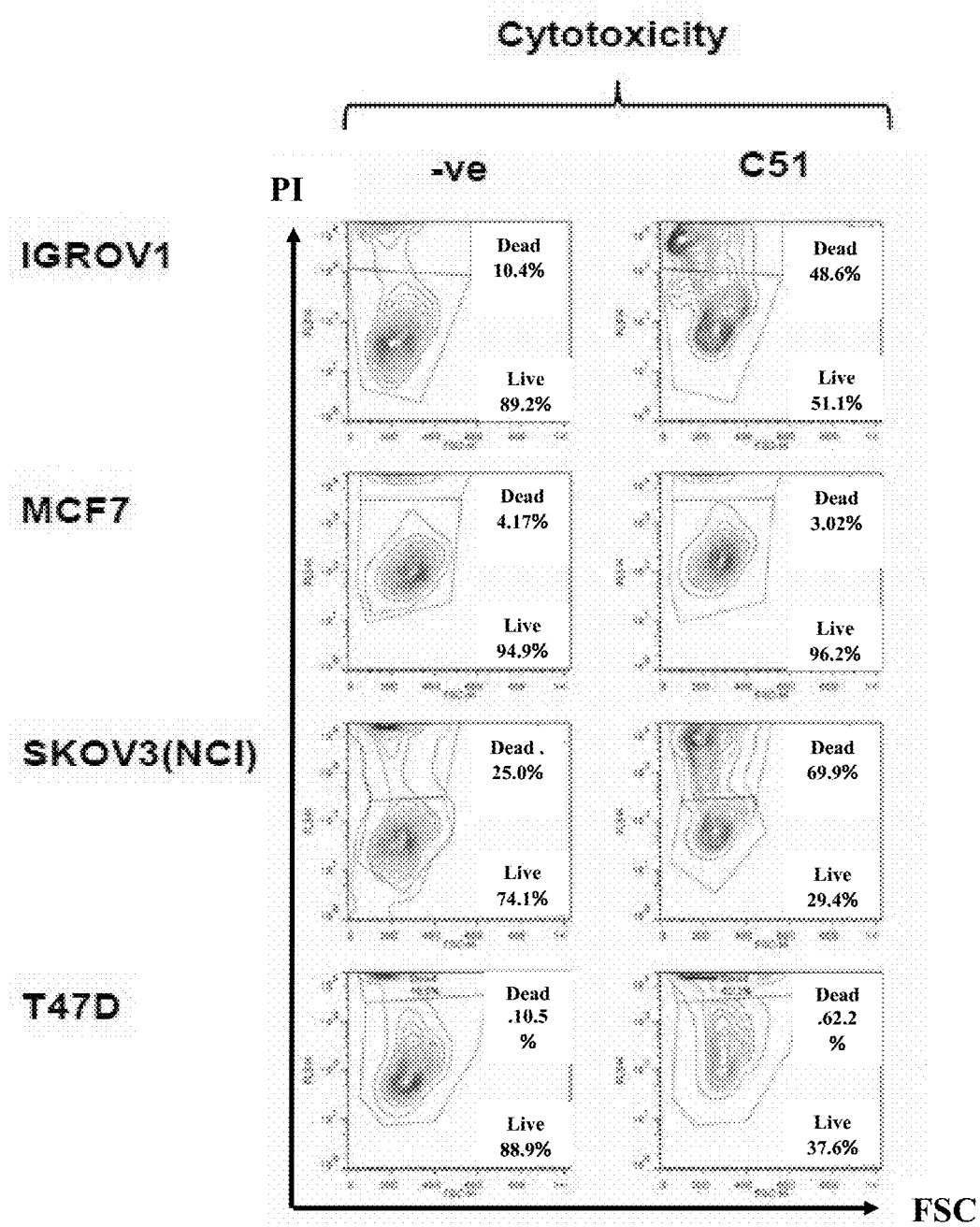
FIG. 5: Direct cytotoxicity of mAb 51 via oncosis. Increase in propidium iodide uptake by a range of tumor cell lines when suspended in the presence of mAb C51 (10 ug/ml).

Ovarian and breast cancer cells incubated with C51 had a significant and rapid increase in PI uptake, indicating a loss of membrane integrity (FIG. 5). A loss of relative viability was observed on IGROV1, MCF7, SKOV3 and T47D cells. Minimal cytotoxicity was observed in media-only controls. Results indicated cell-death via oncosis.

mAb C51 as an antibody-drug conjugate (ADC) kills cancer cells.

Figure 6:
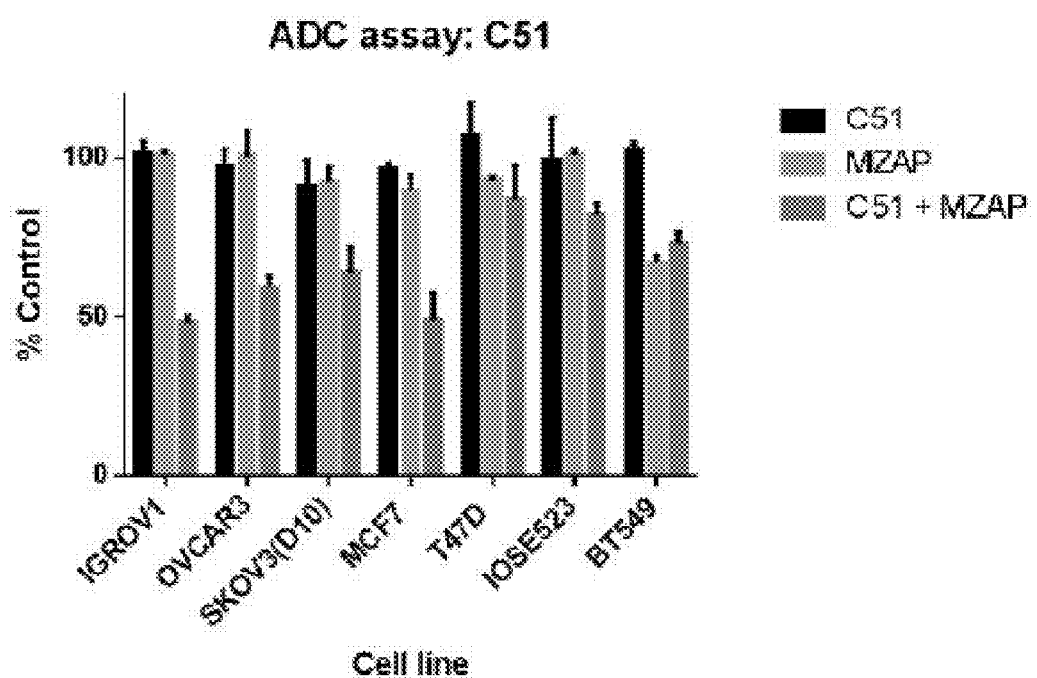
FIG. 6: Targeted delivery of a toxic payload by mAb C51. The ability of mAb C51 to deliver the ribosome inactivating protein, saporin into various cancer cell lines was assessed. Various cell lines were cultured in the presence of mAb C51 preincubated with a saporin-linked antimouse IgG for 72 hours and assessed via CellTiter-Glo® Assay (Promega). Significant anti-proliferative effects were observed in IGROV1, OVCAR3, SKOV3(D10) and MCF7 which are positive for C51 antigen target compared to the negative cell lines IOSE523 and BT549.
Figure 7:
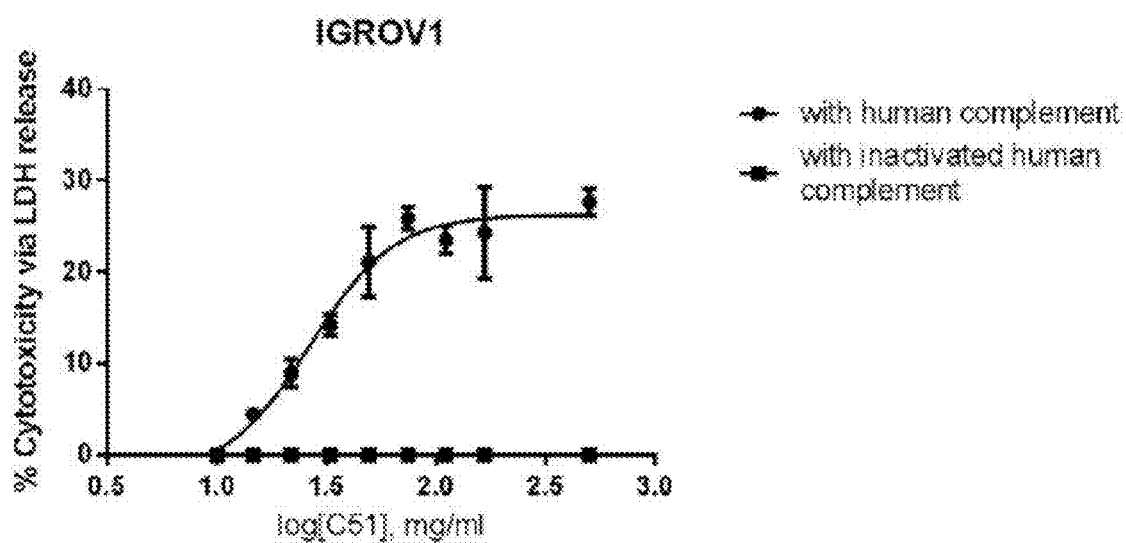
FIG. 7: Complement-Dependent Cytotoxicity (CDC) of mAb C51. The ability of mAb C51 to induce CDC was observed in a dose-dependent manner with up to 30% lysis. IGROV1 cells were incubated with increasing concentrations of mAb C51 in the presence of normal human serum for 2 hours. Cytotoxicity was assessed via LDH release by the CytoTox 96® assay (Promega).

Ovarian and breast cancer cells were incubated in culture with mAb C51 and secondary antibody conjugated to saporin (MZAP). After 72 h of incubation, relative cell viability was measured by the percentage of live cells in the treatment group compared to the buffer-treated control (FIG. 6). Up to 50% cytotoxicity with mAb C51 and secondary mAbs was demonstrated on both IGROV1 and MCF7 cell lines compared to the buffer control, mAb C51 alone or saporin secondary Ab alone. No cytotoxicity was observed for non-binding control cell lines IOSE523 and BT549. Overall, mAb C51 delivered saporin and induce potent cytotoxicity. Results demonstrated the use of mAb C51 as an antibody-drug conjugate (ADC).

mAb C51 induces complement-dependent cytotoxicity (CDC).

mAb C51 demonstrated detectable levels of cell lysis in the presence of human complement (FIG. 7). Up to 30% lysis was observed at high binding saturation concentrations of C51. For control, cells were incubated with mAb and heat-inactivated complement. Results showed that mAb C51 can be used to induce CDC activity on target cancer cells.

Chimeric mAb chC51 as an antibody-drug conjugate (ADC) kills cancer cells.

Figure 8:
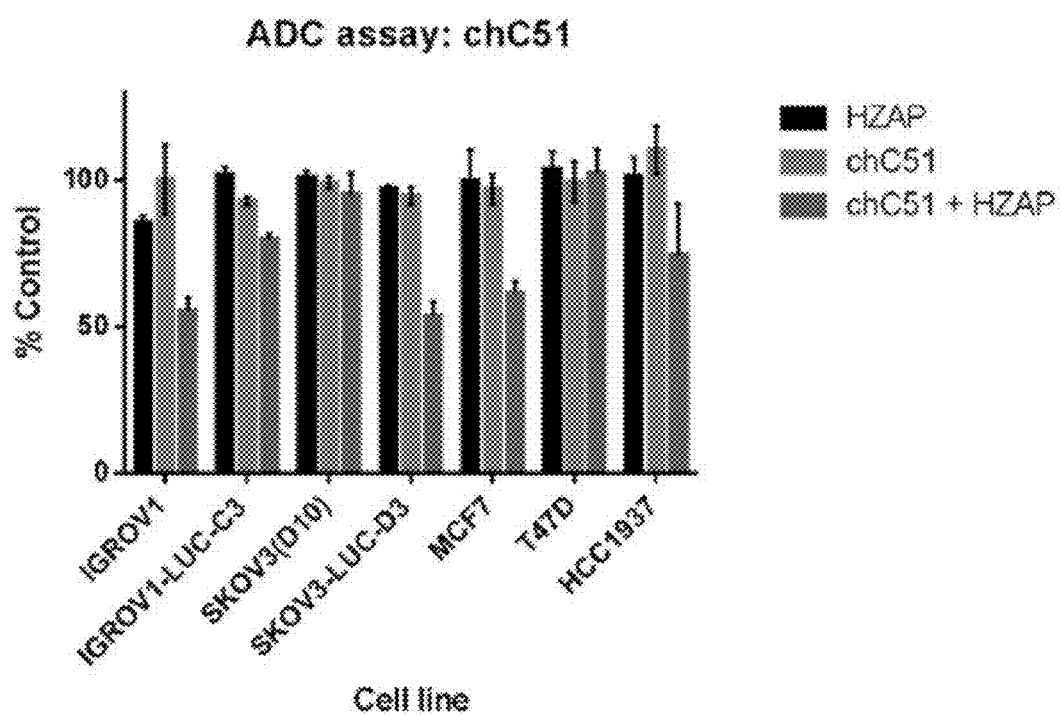
FIG. 8: Targeted delivery of a toxic payload by mAb chC51. The ability of mAb chC51 to deliver the ribosome inactivating protein, saporin into various cancer cell lines was assessed. Various cell lines were cultured in the presence of mAb chC51 preincubated with a saporin-linked antimouse IgG for 72 hours and assessed via CellTiter-Glo® Assay (Promega). Significant anti-proliferative effects were observed in IGROV1, SKOV3-LUC-D3, MCF7 and HCC1937 cell lines.

Ovarian and breast cancer cells were incubated in culture with chimeric C51 mAb (chC51) and secondary anti-human conjugated to saporin (HZAP). After 72 h of incubation, relative cell viability was measured by the percentage of live cells in the treatment group compared to the buffer-treated control (FIG. 8). Overall, chimeric mAb chC51 delivered saporin and induce potent cytotoxicity. Results demonstrated the use of chimeric mAb chC51 as an antibody-drug conjugate (ADC) comparable to the mouse C51 IgM antibody.

mAb chC51 induces antibody-dependent cell-mediated cytotoxicity (ADCC).

Figure 9:
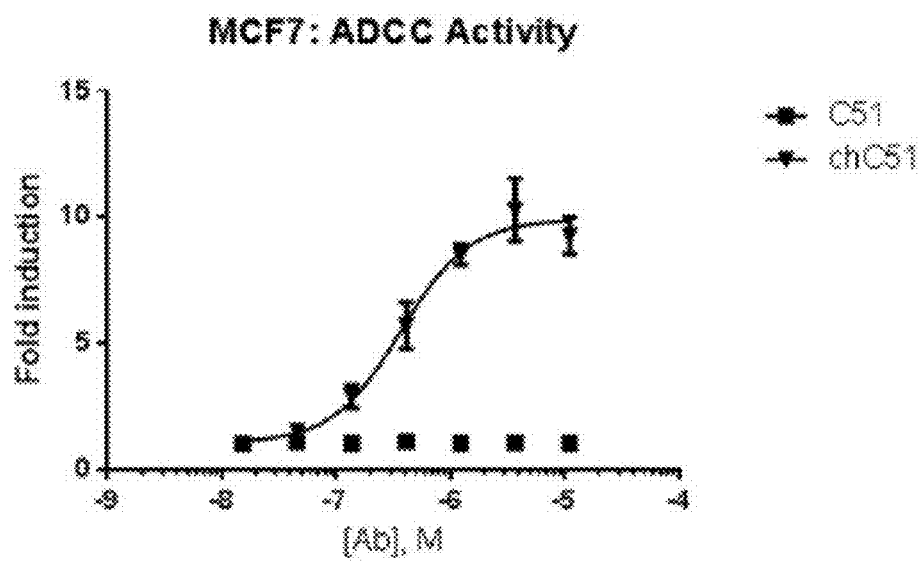
FIG. 9: ADCC activity of C51 vs chC51. chC51 but not C51 exhibited ADCC activity when cultured with MCF7 breast cancer cells. ADCC activity was measured within 6 hour as fold induction of the NFAT ADCC pathway using an ADCC reporter biossay (Promega).

The chimeric mAb chC51 induced ADCC against MCF7 breast cancer cells (FIG. 9). Positive ADCC activity corresponded to binding of chC51 on cells which was not observed on non-binding cancer cell lines.

Ab heavy and light chain sequences and isotype of mAb 2448 is IgG1-kappa.

Heavy and light chain gene sequences of mAb 2448 were cloned from hybridoma cells by reverse transcription polymerase chain reaction (RT-PCR) and sequenced with complementarity-determining regions (CDRs) underlined (FIGS. 10A and B). Isotyping of supernatant from hybridoma clone supernatant revealed that mAb 2448 was an IgG1-kappa immunoglobulin (FIG. 10C).

mAb 2448 demonstrates reactivity to various cancers. mAb 2448 binds to an epithelial phenotype according to a classification based on the Epithelial-Mesenchymal Transition (EMT).

High-throughput screening of mAb 2448 was done on live cells by flow cytometry (FIG. 11A). Cell surface binding was observed on breast (BT474, BT20, CAMA1, HCC1937, HCC1954, HCC2218, MS578T, MCF7, MDAMB453, SKBR3, T47D), colorectal (COLO205, HT29, KM12, LS174T, SW620), kidney (7860, A498, ACHN, CAKI1, UO31, RXF393, TK10), liver (HEP3B, HEPG2, HUH7, PLC) and ovarian (CAOV3, CH1, IGROV1, OV17R, OV90, OVCA432, OVCAR3, OVCAR8, OVCA433, PEA1, SKOV3) cancer cells. Minimal binding was observed on normal cell lines (IOSE523, HEK293, HFF). Results showed that mAb 2448 can specifically bind to multiple cancers. Binding of mAb 2448 to ovarian and breast cancer cells was re-organized according to an Epithelial-Mesenchymal Transition (EMT) classification (FIG. 11B). mAb 2448 was shown to preferentially bind to cells classified with an epithelial (E) and intermediate epithelial (IE) phenotype. Results showed that mAb 2448 can potentially be used to monitor EMT. Isogenic breast cancer cell lines MCF7-D10 and MCF7-2101 display epithelial and mesenchymal phenotypes of EMT, respectively. Significantly higher levels of the epithelial marker E-Cadherin and lower levels of the mesenchymal marker Vimentin are expressed in MCF7 cells versus MCF72101 cells, respectively. Microscopy images of 2448 on MCF-D10 and MCF7-2101 isogenic cell lines (FIG. 11C). Phase contrast images revealed EMT-like morphological changes. MCF7-D10 cells were more epithelial with cuboidal or "cobblestone-like" cells compared to MCF7-2101 cells which were more isolated and elongated. Membranous binding of 2448 was observed on MCF7-D10 cells but not on the isogenic MCF7-2101 cells by immunocytochemistry. mAb 2448 binds on live MCF7-D10 cells, but not on MCF7-2101 cells.

Annexin A2 is identified as the antigen target of mAb 2448 in an ovarian cancer cell line.

Immunoprecipitation (IP) was carried out on IGROV1 ovarian cancer cells to enrich for the antigen of mAb 2448. IP product was immunoblotted with 2448 (FIG. 12A). Corresponding bands on a silver stained gel were excised and analyzed by liquid chromatography tandem mass spectrometry (LC-MS/MS) Results demonstrated Annexin A2 as the antigen target of mAb 2448 (FIG. 12B). Peptide coverage spanned across the entire amino acid sequence of ANXA2 after multiple rounds of IP and LC-MS/MS.

Annexin A2 is identified as the antigen target of mAb 2448 in hESC and a breast cancer cell line.

Figures 13A, 13B:
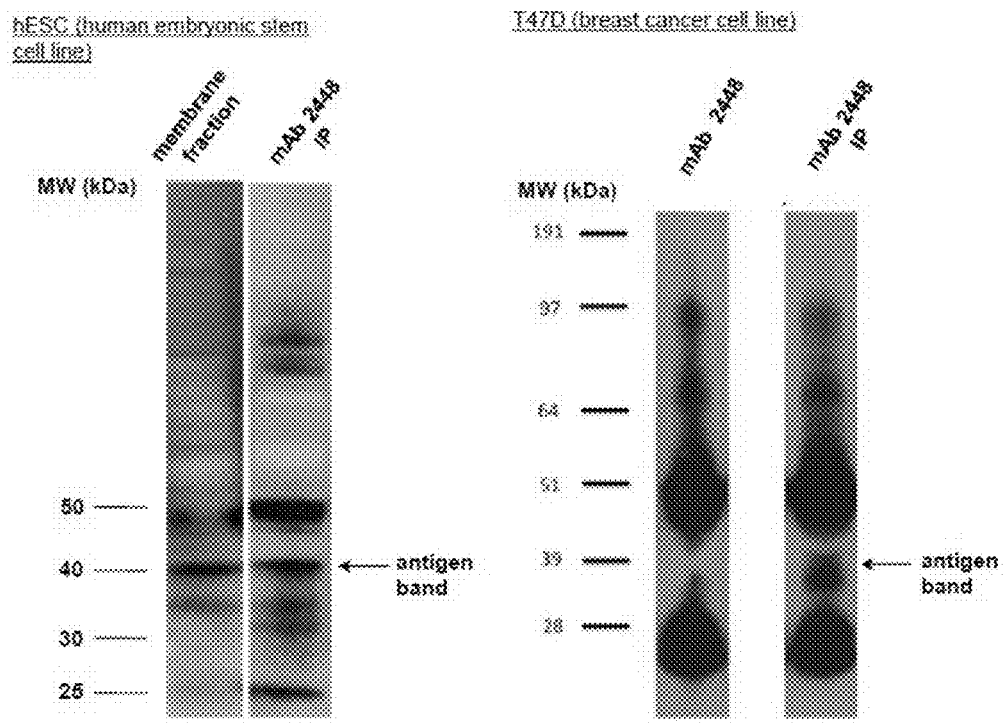
FIGS. 13A and 13B: Antigen target identification of 2448.

Immunoprecipitation (IP) was carried out on hESC and T47D breast cancer cells to enrich for the antigen of mAb 2448. IP product was immunoblotted with mAb 2448 (FIG. 13A). Corresponding bands on a silver stained gel were excised and analyzed by liquid chromatography tandem mass spectrometry (LC-MS/MS). Annexin A2 was identified as a top protein hit (FIG. 13B). Results demonstrated Annexin A2 as the antigen target of mAb 2448.

Annexin A2 is validated as the antigen target of mAb 2448 in human embryonic stem cells (hESC) and a breast cancer cell line.

Figure 14A:
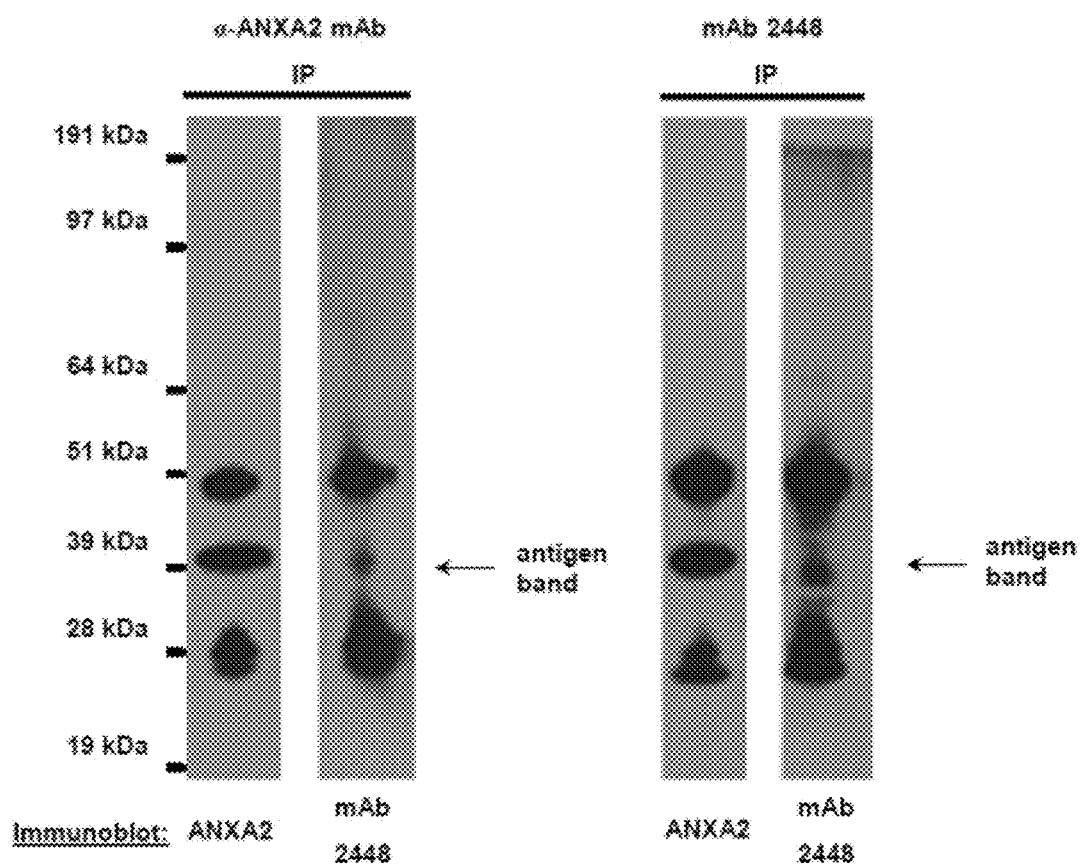
FIGS. 14A and 14B: Validation of ANXA2 as the antigen target of 2448.
Figure 14B:
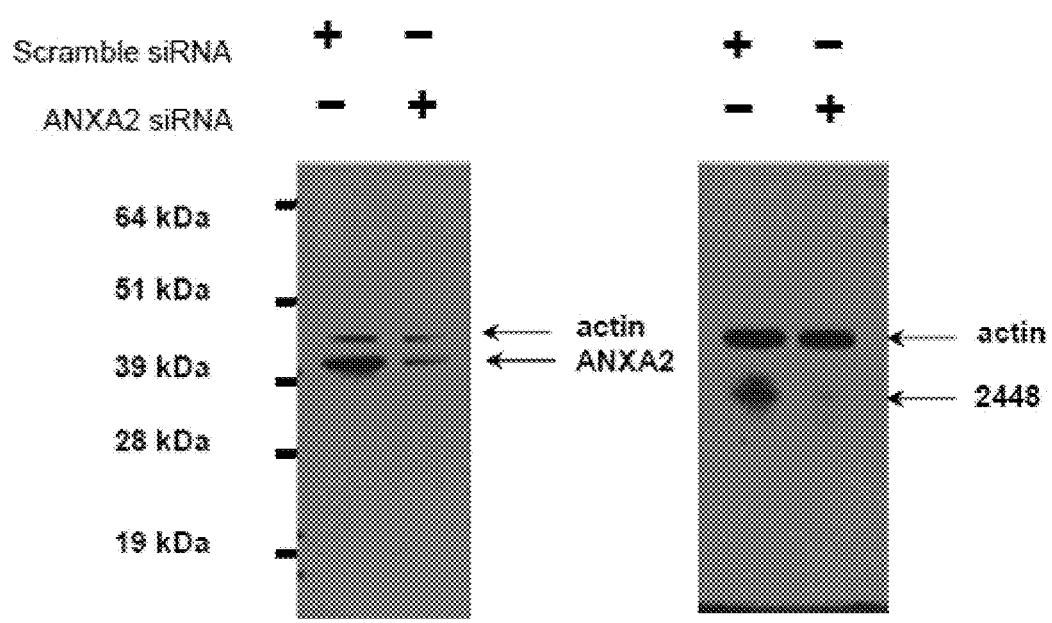

To validate ANXA2 as the antigen target of mAb 2448, a forward and reverse-immunoprecipitation (IP) was carried out using a commercial anti-ANXA2 mAb. IP products were immunoblotted against mAb 2448 and the commercial antibody (FIG. 14A). mAb 2448 recognized similar antigen bands for both IP products. A transient siRNA knockdown study of ANXA2 was also carried out (FIG. 14B). Partial knockdown of ANXA2 corresponded to a loss of antigen recognition by mAb 2448. Taken together, results demonstrated Annexin A2 as the antigen target of mAb 2448.

Figure 15:
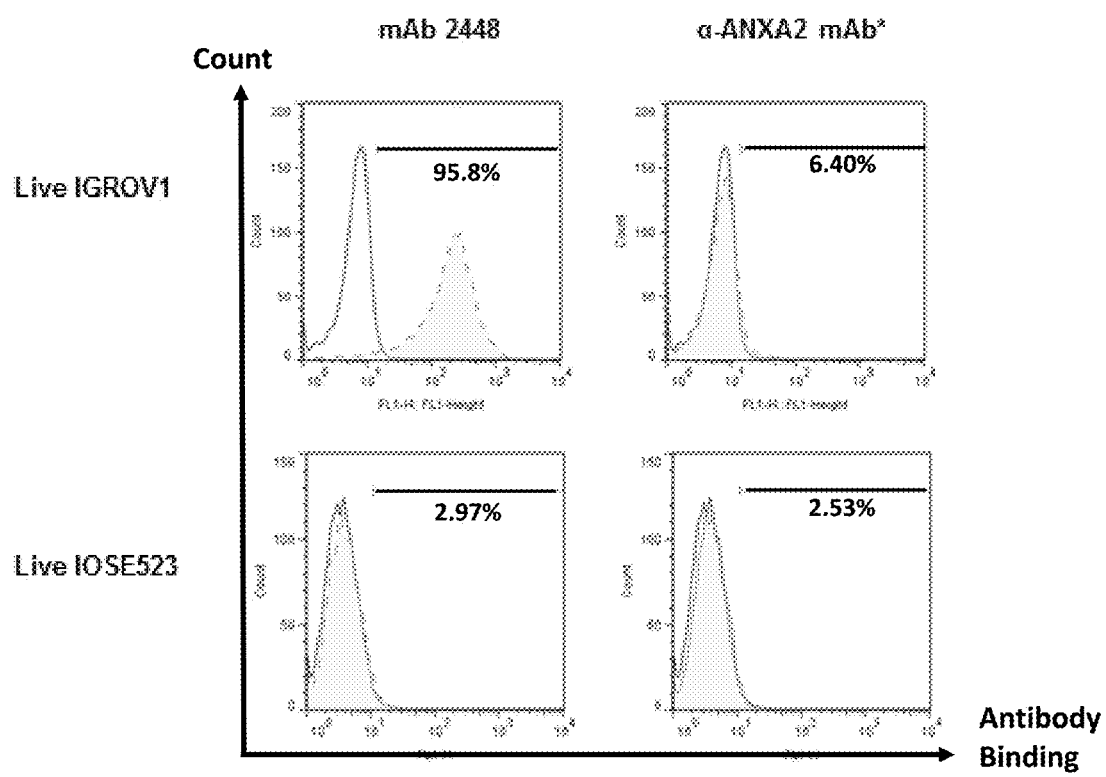
FIG. 15: Binding of 2448 to the cell surface. mAb 2448 bound on the cell surface of live IGROV1 cells via flow cytometry. Commercial α-ANXA2 antibodies such as those reported in literatures were unable to bind to live cells. Solid line is negative control; dashed line is mAb 2448.
Figure 16A:
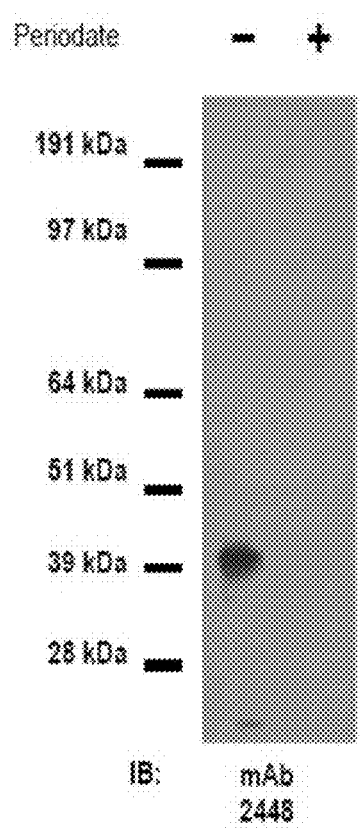
FIGS. 16A and 16b: Binding of mAb 2448 to an N-glycan epitope.
Figure 16B:
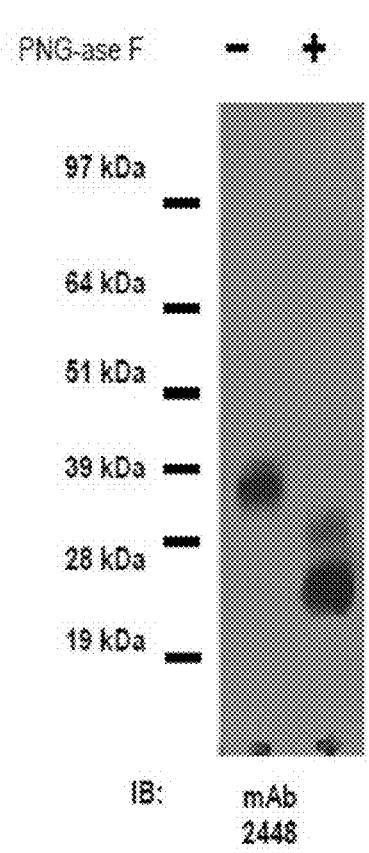
Figure 17A:
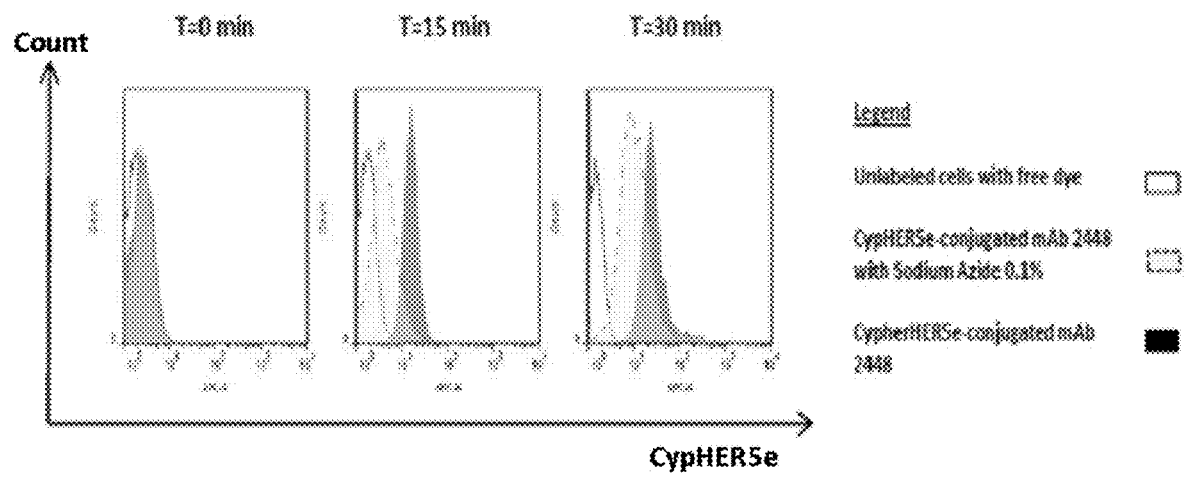
FIGS. 17A and 17B: Rapid cellular internalization of mAb 2448. mAb 2448 was labeled with two pH sensitive dyes, CypHER5E (FIG. 17A) and pH-RODO (FIG. 17B), that increased in fluorescence intensity in low pH environments. Dye-conjugated mAb 2448 internalizes into endosomal and lysosomal compartments as measured via flow cytometry analysis by an increase in total mean fluorescence.
Figure 17B:
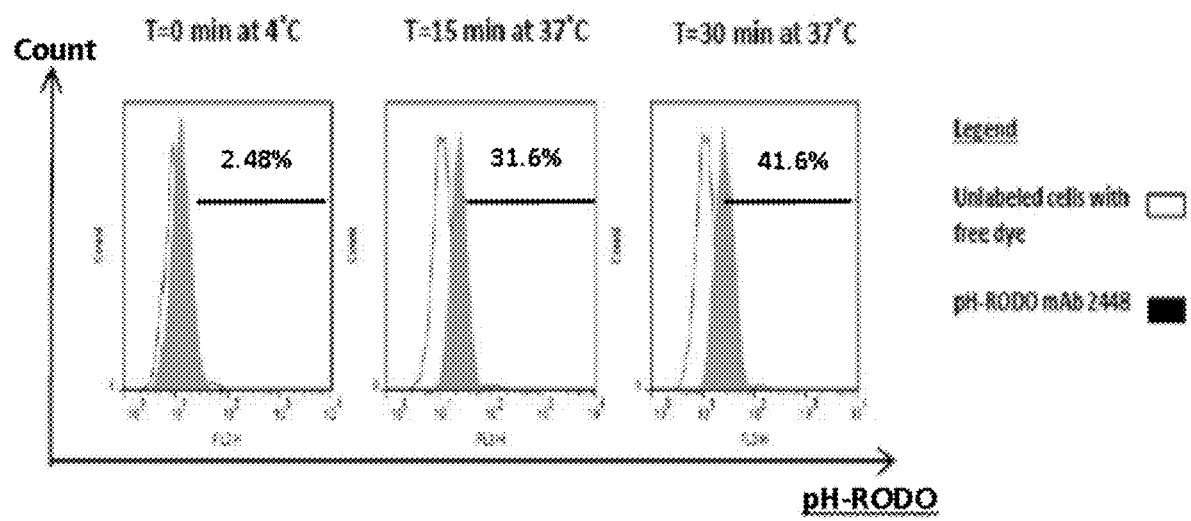

Only mAb 2448 binds to cell surface Annexin A2.

mAb 2448 was evaluated for binding on cancer cells. Strong cell surface binding was demonstrated for mAb 2448 unlike commercial anti-ANXA2 antibodies (FIG. 15). Commercial antibodies only demonstrated binding after cells were fixed and permeabilized. Results demonstrate that mAb 2448 binds to unique surface epitopes on cancer cells unlike other anti-ANXA2 mAbs.

mAb 2448 targets an N-glycan epitope.

mAb 2448 binding was loss after periodate treatment (FIG. 16A) and PNGase F enzymatic release (FIG. 16B). Loss of binding demonstrated that mAb 2448 was binding to N-glycan-dependent epitopes on ANXA2.

mAb 2448 internalizes into cancer cells.

mAb 2448 was conjugated to CypHER5E (FIG. 17A) and pHRodo dye (FIG. 17B). Results demonstrated the ability of mAb 2448 to efficiently internalize into target cancer cells.

mAb 2448 and chimeric mAb ch2448 kill target cancer cells as antibody drug conjugates (ADCs).

To demonstrate either 2448 or ch2448 as a potential ADC, mAbs were evaluated with secondary conjugates of the plant-derived toxin, saporin. Ovarian and breast cancer cells were incubated with primary mAb (2448 or ch2448), secondary saporin conjugate (mAb-ZAP or HUM-ZAP) or complexes of primary mAb and secondary conjugates (FIG. 18).

The complexes of primary mAb and secondary conjugates delivered saporin into cells and induced cytotoxicity. Overall, results indicated that both 2448 and ch2448 were viable targeting agents for development as an ADC.

Chimeric mAb ch2448 as an antibody-drug conjugate (ADC) kills target cancer cells in a dose-dependent manner.

Figure 19A:
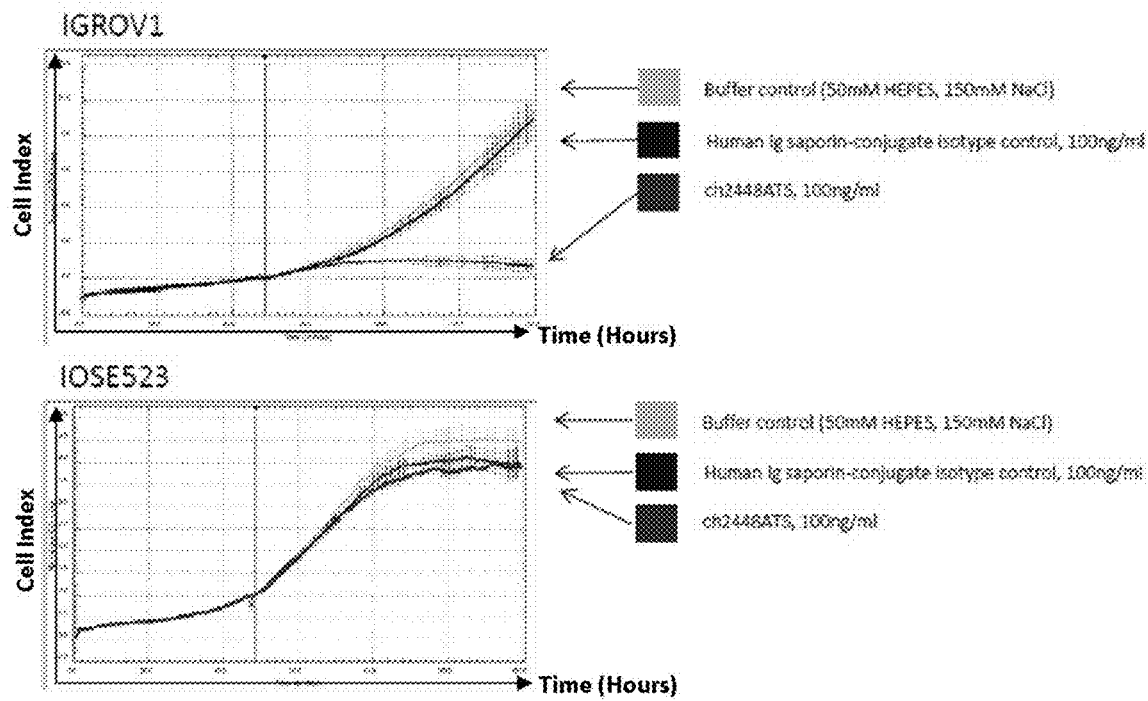
FIGS. 19A and 19B: Dose-dependent cytotoxicity of ch2448-saporin (ch2448ATS). Cells were incubated with either ch2448ATS or control (Human Ig saporin-conjugate or chTNA2ATS).
Figure 19B:
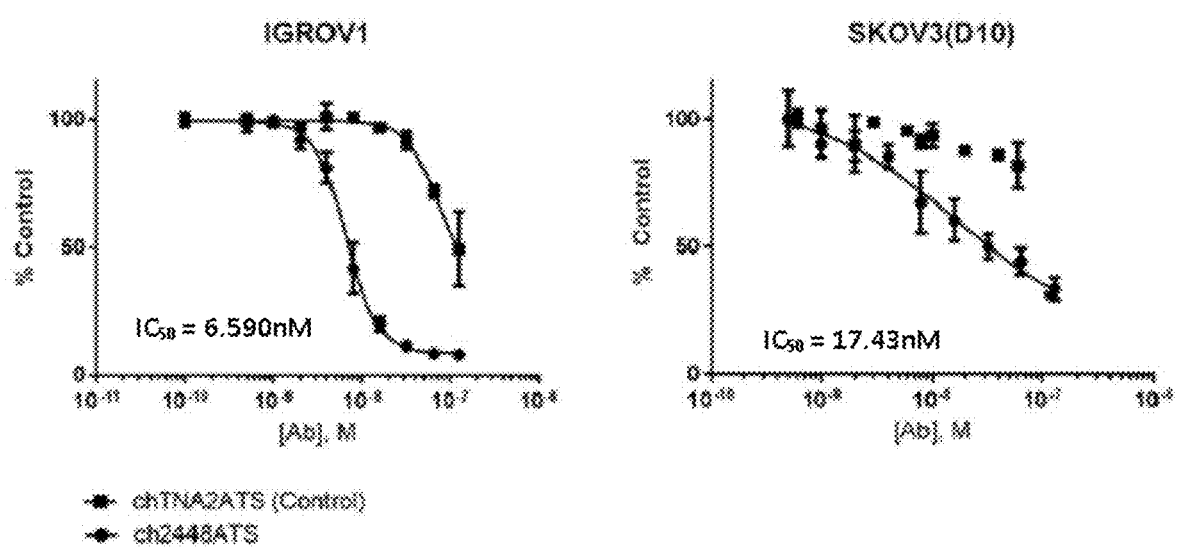

Chimeric mAb 2448 was conjugated to a plant-derived toxin (saporin) to create an antibody drug conjugate (ADC). As an ADC, ch2448 killed IGROV1 target ovarian cancer cells but not IOSE523 normal ovarian cells (FIG. 19A). Dose dependent cytotoxicity was observed on IGROV1 and SKOV3 ovarian cancer cell lines (FIG. 19B). Results demonstrated that chimeric mAb ch2448 can be used as an ADC with potent cytotoxicity.

Chimeric mAb ch2448 induces antibody-dependent cell-mediated cytotoxicity (ADCC).

Figure 20A:
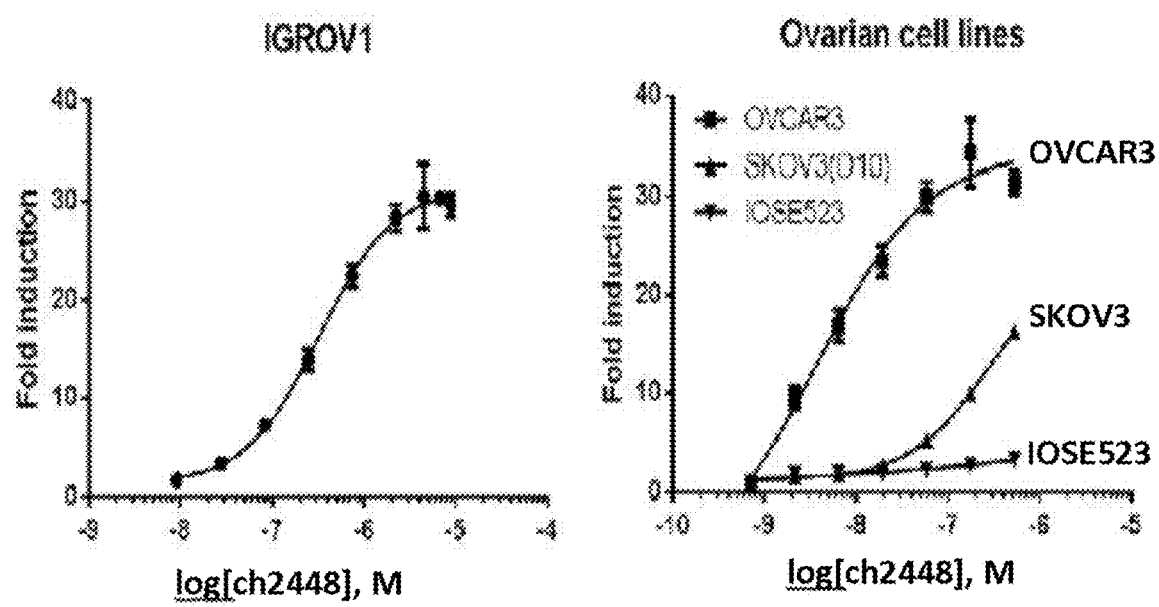
FIGS. 20A and 20B: ADCC activity of ch2448. ch2448 exhibited ADCC activity against ovarian (FIG. 20A) and breast cancer (FIG. 20B) cells. ADCC activity was measured as fold induction of the NFAT ADCC pathway using an ADCC reporter bioassay (Promega).
Figure 20B:
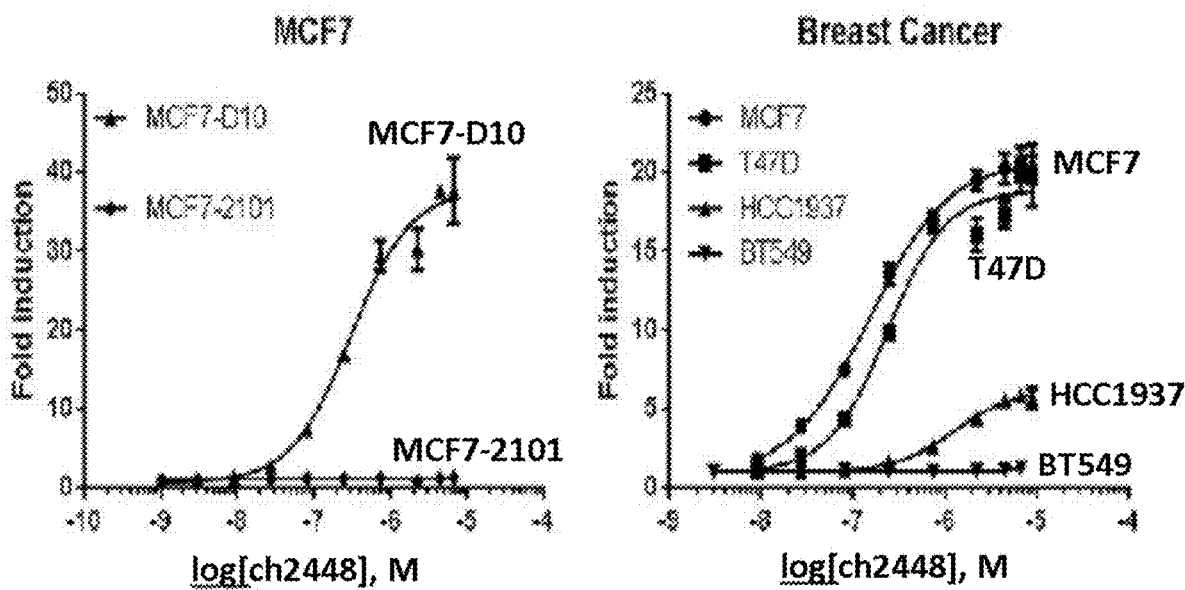

Chimeric mAb ch2448 was co-incubated with target cancer cell lines and effector cells. Dose dependent activation of the ADCC NFAT pathway was measured by luciferase readout. Chimeric mAb ch2448 can be used to activate ADCC activity against ovarian cancer cells (FIG. 20A) and breast cancer cells (FIG. 20B).

Chimeric mAb 2448 delays tumor growth in vivo.

Figure 21A:
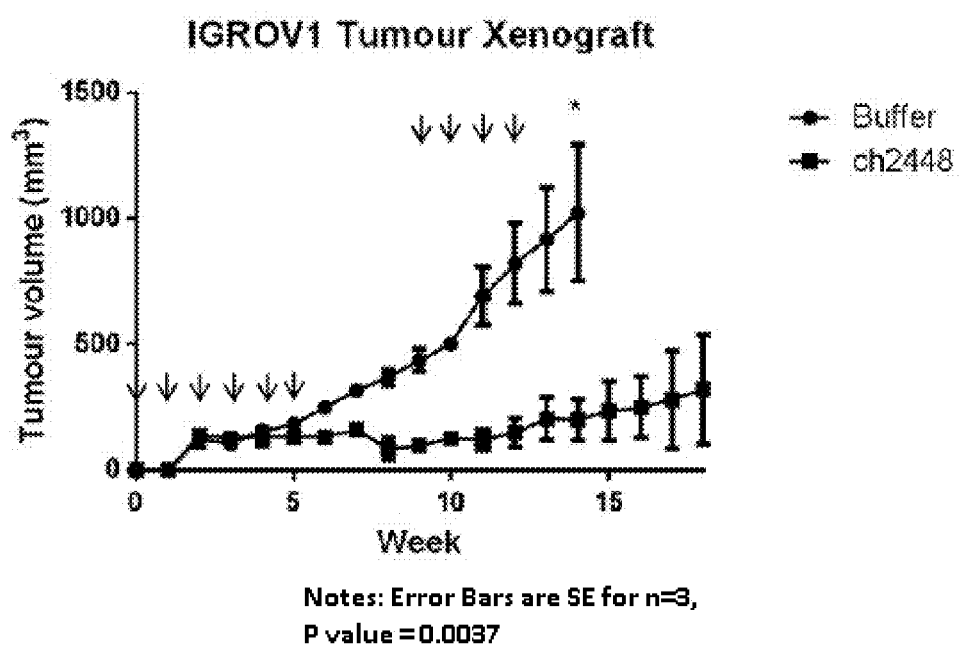
FIGS. 21A and 21B: In vivo activity of ch2448 in a nude mouse xenograft model.
Figure 21B:
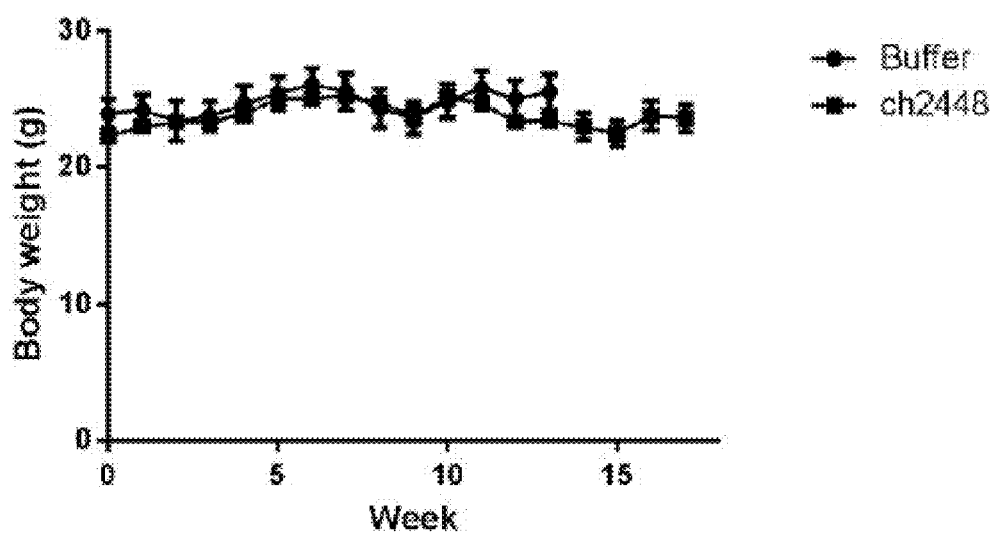

Chimeric mAb ch2448 delayed tumor growth in an IGROV1 ovarian cancer xenograft mouse model (FIG. 21A). No drastic changes in body weight were observed (FIG. 21B), suggesting no adverse effects of antibody treatment. Results suggest that ch2448 can be used as a naked antibody treatment for ovarian cancer.

Chimeric mAb ch2448 delays tumor growth in vivo via ADCC.

Figure 22B:
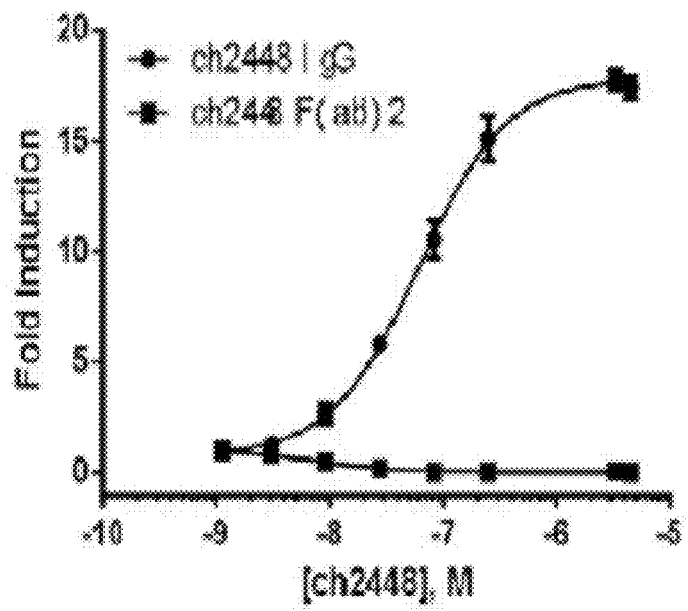
Figure 22C:
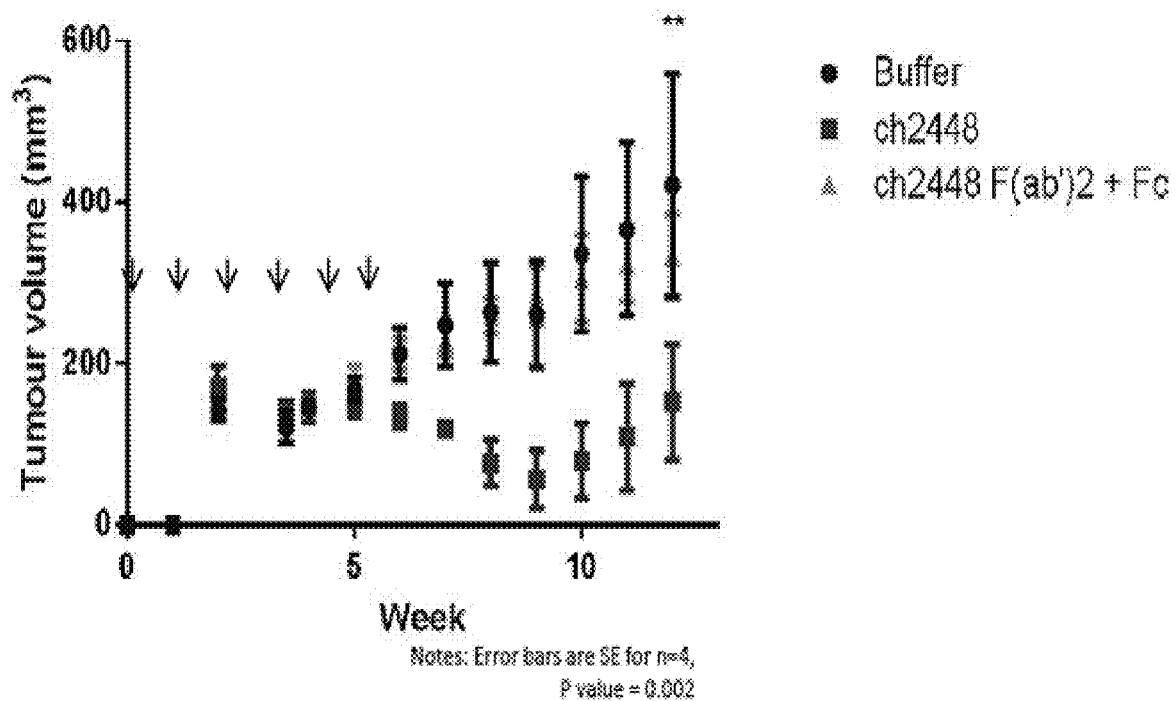

A F(ab)'2 of ch2448 was generated (FIG. 22A) with no ability to induce antibody-dependent cell-mediated cytotoxicity (ADCC) (FIG. 22B). Chimeric mAb ch2448 as an IgG but not as a F(ab')2 delayed human ovarian tumor growth in a mouse xenograft model (FIG. 22C). Results demonstrated the ability of ch2448 to delay tumor growth via ADCC.

Afucosylation enhances the ability of ch2448 to induce antibody-dependent cell-mediated cytotoxicity (ADCC).

Figure 23A:
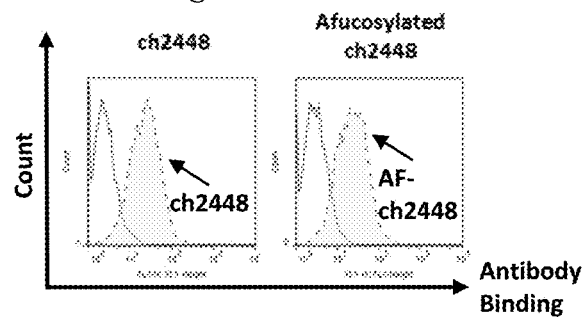
FIGS. 23A and 23B: Enhanced ADCC activity of an afucosylated ch2448.
Figure 23B:
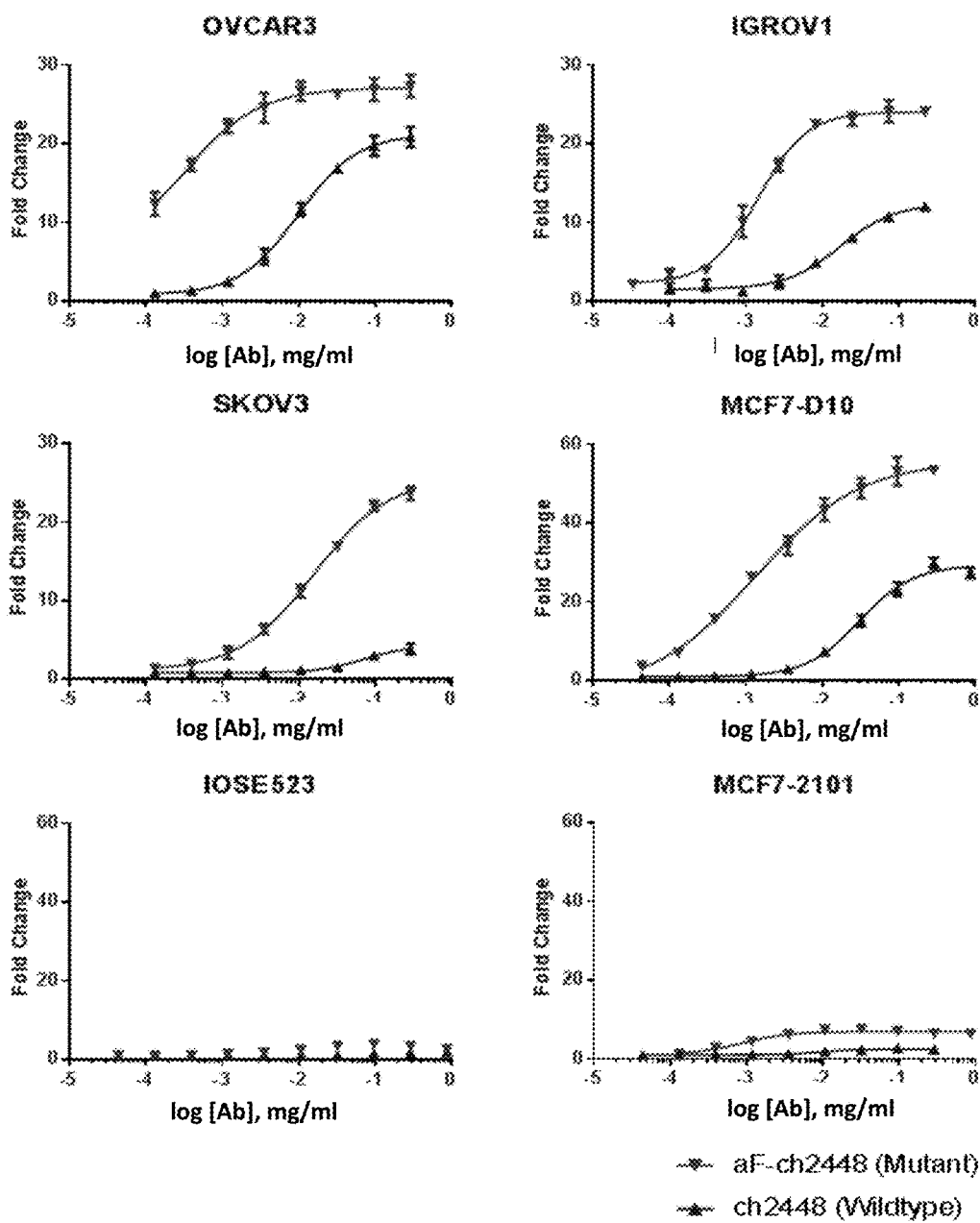
Figures 24A, 24B:
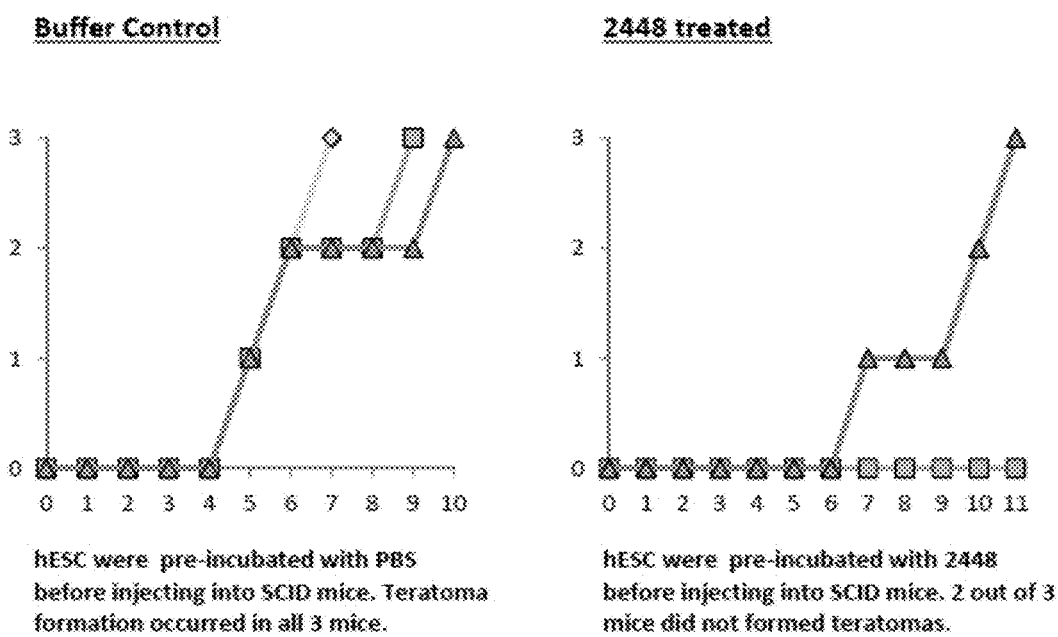
FIGS. 24A and 24B: mAb 2448 in hESC Therapy.
Figure 25A:
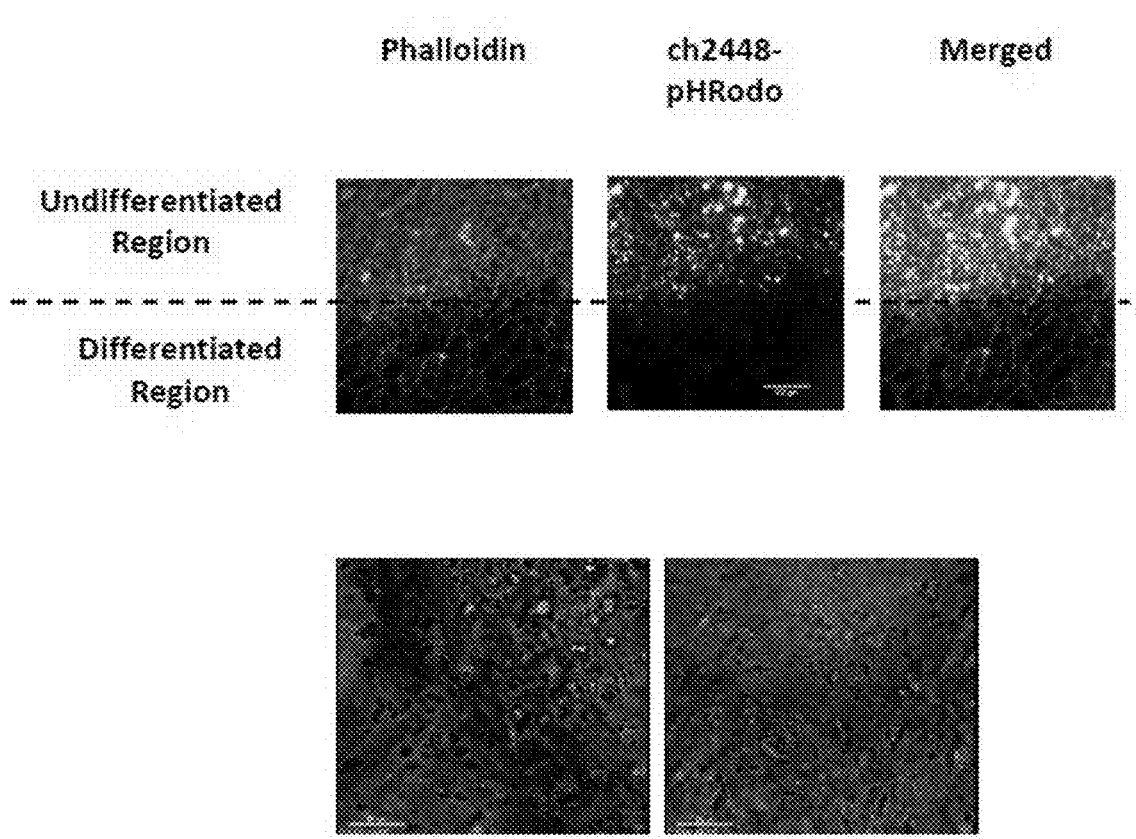
FIGS. 25A, 25B, and 25C Internalization of ch2448 in hESC. ch2448 internalizes into hESC as observed in the pH-Rodo assay.
Figure 25B:
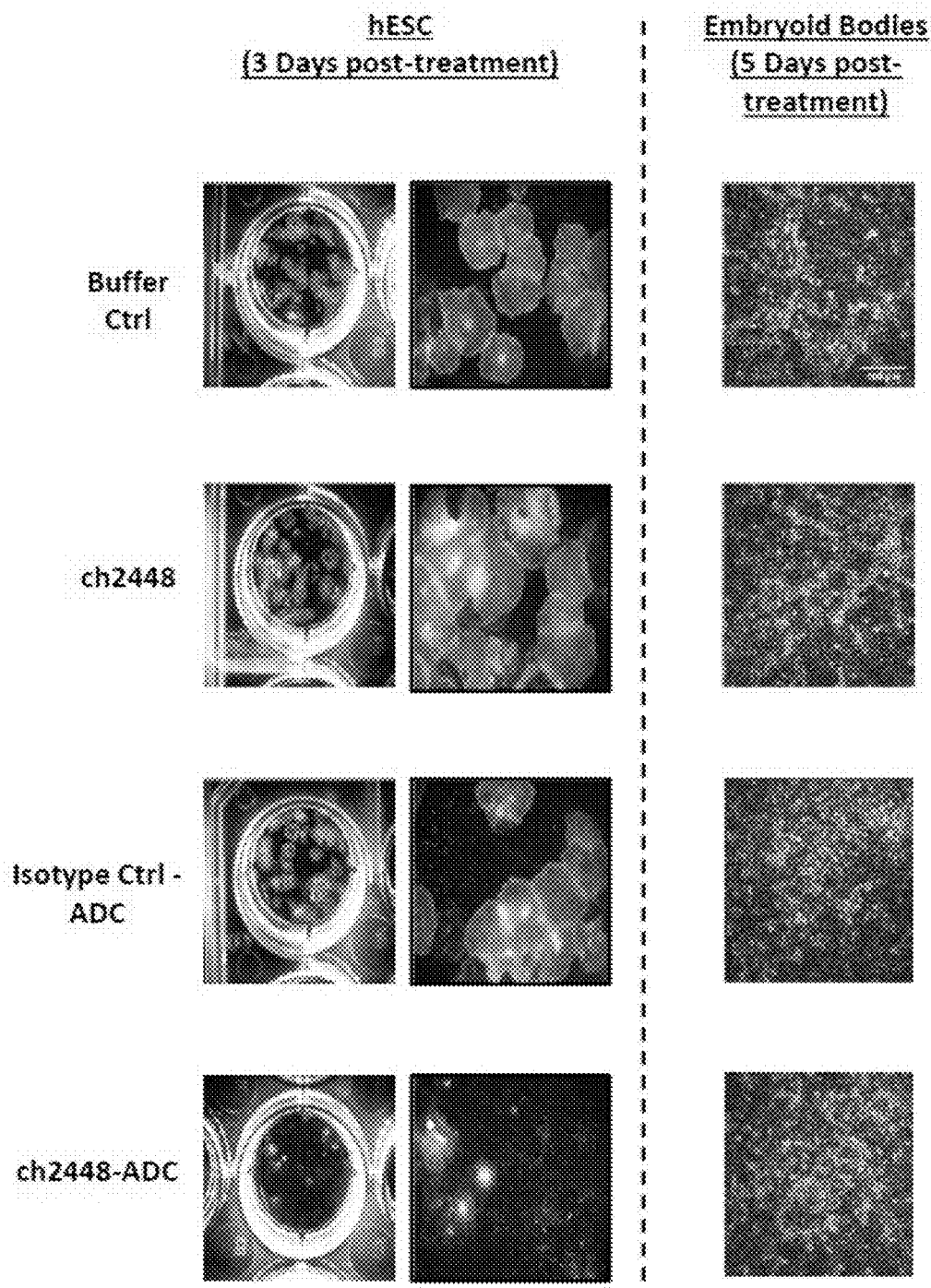
Figure 25C:
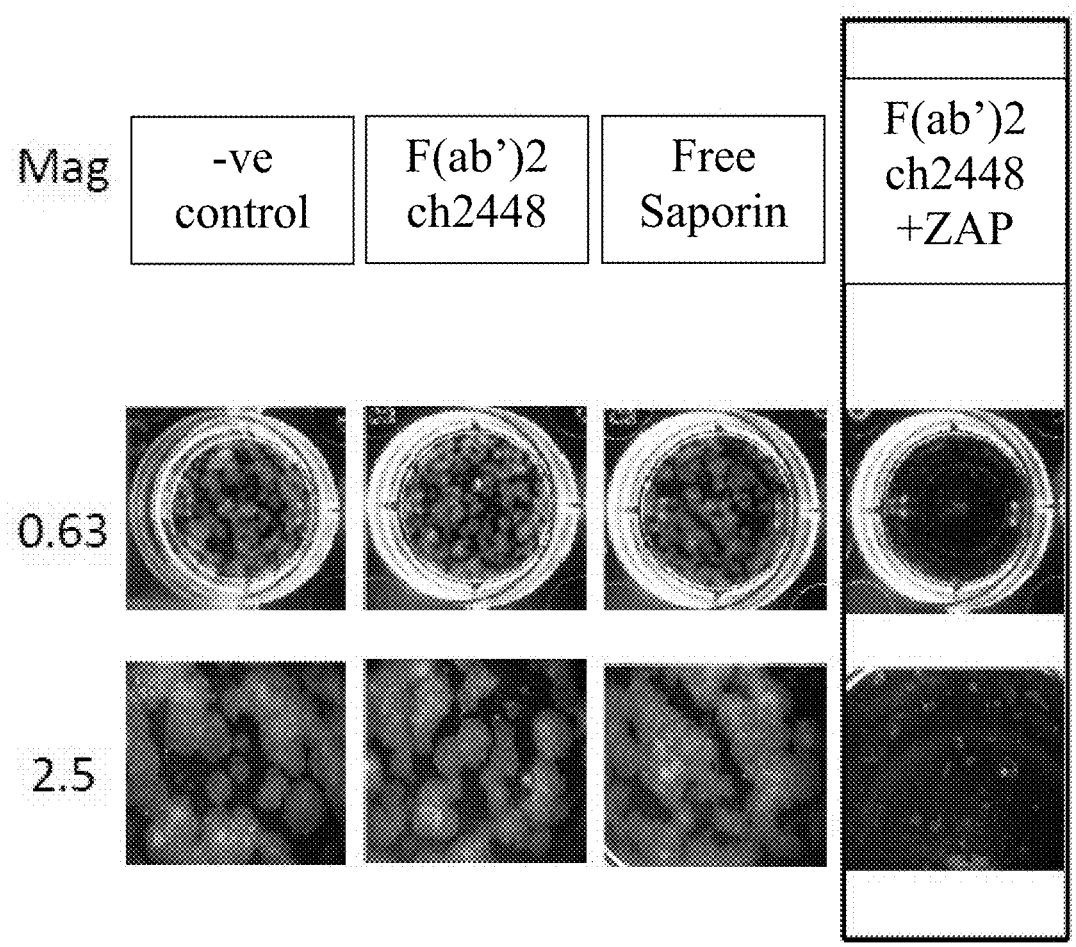

Afucosylated ch2448 retained similar binding to wildtype chimeric mAb ch2448 (FIG. 23A). mAb ch2448 and aF-ch2448 were incubated with target cancer cells and effector cells. aF-ch2448 induced greater ADCC activity compared to ch2448 as indicated by an increase in fold change (FIG. 23B). Results showed that afucosylation of ch2448 retained antibody-antigen specificity and significantly enhanced ADCC activity of ch2448.

mAb ch2448 binds strongly to undifferentiated hESC and prevents teratoma formation in vivo.

mAb 2448 binds specifically to undifferentiated hESC but not to differentiated embryoid bodies (EBs) (FIG. 24A). hESC were either pre-incubated with PBS buffer or with mAb 2448 prior to injecting into SCID mice intramuscularly (FIG. 24B). Teratomas formed within week 5 in all 3 mice in the buffer control. Cells treated with 2448 saw prevention in teratoma (n=2) or a delay in teratoma (n=1, week 7). Hence, as a naked mAb, 2448 can prevent or delay the formation of teratoma in SCID mice.

ch2448 internalizes into hESC and kills undifferentiated hESC as an ADC.

ch2448 was conjugated to pHRodo dye and internalization of ch2448 was observed over 24 hrs (FIG. 25A). hESC was partially differentiated spontaneously and actin stained with phalloidin. Undifferentiated hESC showed dense actin staining while differentiated cells had sparse actin staining. ch2448 (conjugated to pHRodo) binds to and internalizes into undifferentiated regions (FIG. 25B). ch2448 as a F(ab')2 can be conjugated to a toxin and potentially be used as an ADC to kill undifferentiated hESC. Hum-Zap was incubated with ch2448 as an ADC complex and spiked into undifferentiated hESC cultures. The ch2448-ADC killed the undifferentiated hESC within 3 days (FIG. 25C). No killing was observed for the buffer control, ch2448 alone and the isotype control ADC. The ch2448 ADC does not kill differentiated embryoid bodies. The Fc region of ch2448 was removed enzymatically and complexed with anti-Fab saporin as an ADC (FIG. 25C). The F(ab')2-ADC killed the undifferentiated hESC within 3 days. No killing was observed for the buffer control, F(ab)2 alone and the free saporin control.

mAb 2448 as a F(ab')2-ADC prevents or delays teratoma formation in vivo.

Single-cell suspension of human embryonic stem cells ($5 \times 10^6$ cells per animal) were pre-incubated with either buffer or mAb 2448 a F(ab')2-ADC at 4° C. for 20 minutes and then injected into the right hind leg muscle of SCID mice. The F(ab')2-ADC was able to prevent tumor formation compared to the control group (FIG. 26A). Single-cell suspension of human embryonic stem cells ($5 \times 10^6$ cells per animal) were injected into the right hind leg muscle of SCID mice (n=3). Buffer and ADC were subsequently administered intra-peritoneal.

Prevention or delayed teratoma formation by 2448-F(ab')2-ADC in SCID mouse was observed compared to the control group (FIG. 26B). Results demonstrated the ability of mAb 2448 to be used as an ADC to prevent or delay teratoma formation in vivo.

CAR(2448) was constructed using the CD28 co-stimulatory domain, and an IgG4 Fc region linker domain. A T2A element and eGFP were inserted downstream in the same open reading frame as the CAR construct.

Figure 27:
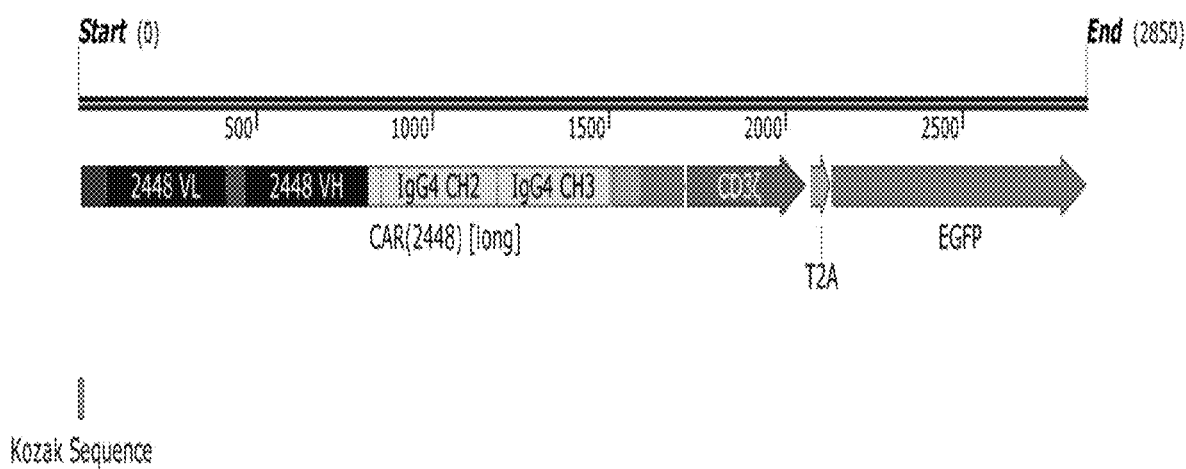
FIG. 27. Structure of CAR(2448). CAR(2448) was constructed as a 2nd generation CAR using the CD28 costimulatory domain, and an IgG4 Fc region linker domain. A T2A element and eGFP were inserted downstream in the same open reading frame as the CAR construct.

A second generation CAR utilising the $V_H$ and $V_L$ regions of mAb 2448 was constructed to determine the utility of the antibody in a CAR format. An eGFP element was utilised as a reporter for CAR expression (FIG. 27).

Key cytokines associated with T cell activation are upregulated upon co-incubation of CAR(2448) T cells with complement antigen-expressing target cells.

Figure 28:
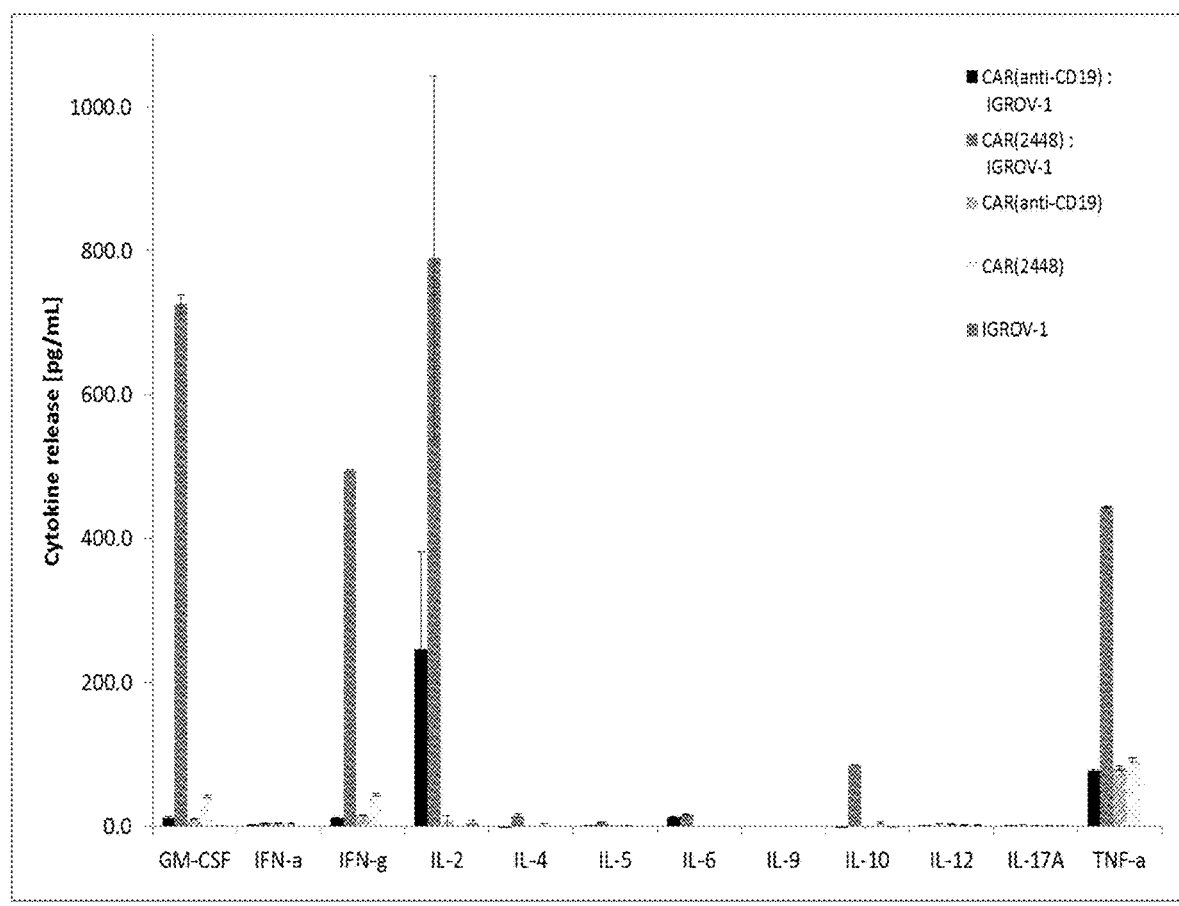
FIG. 28. Overview of cytokine secretion by CAR-T cells. Where indicated, T cells were co-incubated with target IGROV-1 cells at a 10:1 ratio. Cells were incubated for 6 hours at 37° C., 5% CO2 before capture with anti-cytokine beads. Results indicate a significant increase in T cell cytokines by CAR(2448) T cells upon exposure to IGROV-1 cells that express the target Annexin A2. In particular, granulocyte-macrophage colony-stimulating factor, interferon-γ, interleukin-2, and tumor necrosis factor-α, are the cytokines with the highest levels of secretion upon activation with target.

A significant increase in T cell cytokines by CAR(2448) T cells was observed upon exposure to IGROV-1 cells that express the target Annexin A2 (FIG. 28). High levels of IFN-γ, IL-2, GM-CSF, and TNF-α suggested the activation of T cell subsets necessary for tumor clearance.

After T cells were co-incubated with target IGROV1 cells, multiple cytokines show a significant increase in cytokine production compared to a non-target specific CAR control.

Figure 29:
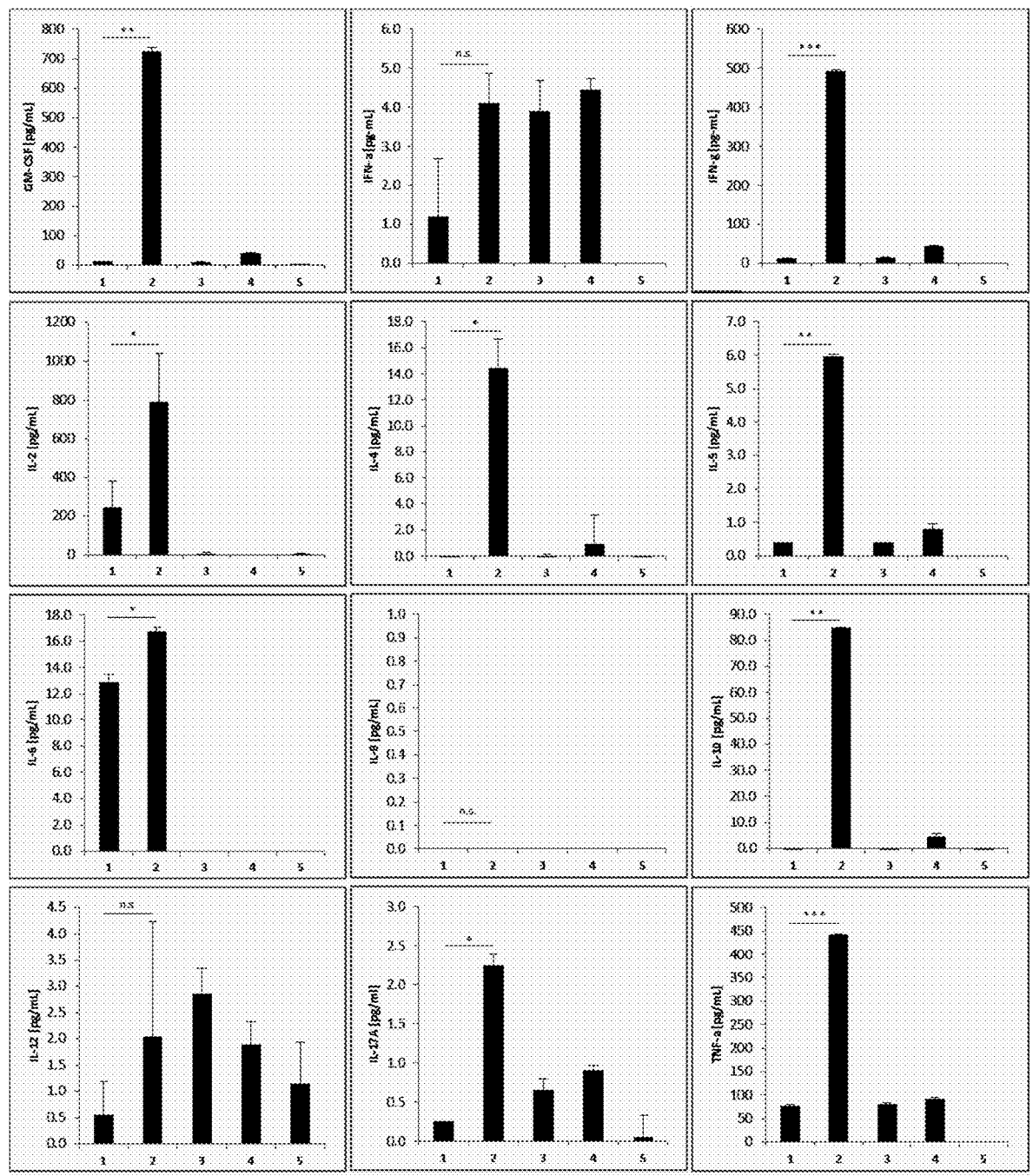
FIG. 29. Detailed Cytokine secretion profile by CAR-T cells. Where indicated, T cells were co-incubated with target IGROV-1 cells at a 10:1 ratio. Cells were incubated for 6 hours at 37° C., 5% CO2 before capture with anti-cytokine beads. The results indicated that multiple cytokines (GM-CSF, IFN-γ, IL-2, IL-4, IL-5, IL-6, IL-10, IL-17A, and TNF-α) showed a significant increase in cytokine production compared to a non-target specific CAR control. Condition 1: CAR(anti-CD19):IGROV-1; Condition 2: CAR(2448):IGROV-1; Condition 3: CAR(anti-CD19); Condition 4: CAR(2448); Condition 5: IGROV-1 (n=2 for all samples; n.s. —P>0.05; *—P<0.05; —P<0.01; *—P<0.001)

The upregulation of multiple cytokines (GM-CSF, IFN-γ, IL-2, IL-4, IL-5, IL-6, IL-10, IL-17A, and TNF-α) by CAR(2448) T cells incubated with IGROV-1 suggested that multiple T cell subsets were activated, indicating the capability of the CAR(2448) construct in activating a broad range of T cell subsets (FIG. 29).

CAR(2448) mediates T cell cytotoxicity against target cells compared to non-specific CAR control.

Figure 30:
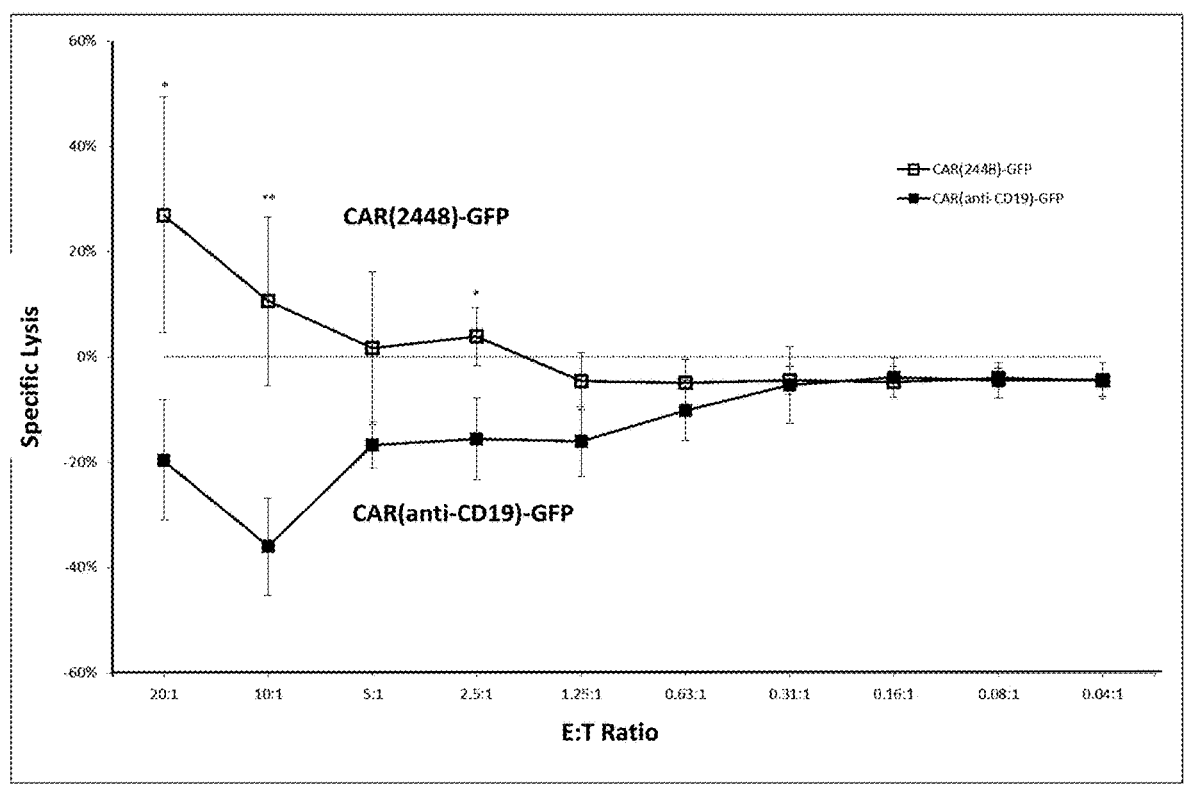
FIG. 30. Cytotoxicity of CAR(2448). CAR(2448) mediates T cell cytotoxicity against target cells compared to non-specific CAR control. Effector IGROV-1 cells were co-incubated with CAR-T cells at varying E:T ratios, in a 4 hour assay, before detection of LDH by lysed cells. The results indicate that T cells nucleofected to express the CAR(2448) construct are capable of mediating cytotoxicity against target IGROV-1 cells in a dose-dependent manner, compared to a non-target specific CAR construct. (n=3 for all samples; *—P<0.05; **—P<0.01).

CAR(2448) T cells mediated cytotoxicity against target IGROV-1 cells in a dose-dependent manner (FIG. 30).

CAR(2448) T cells mediates growth inhibition of target cells.

Figure 31:
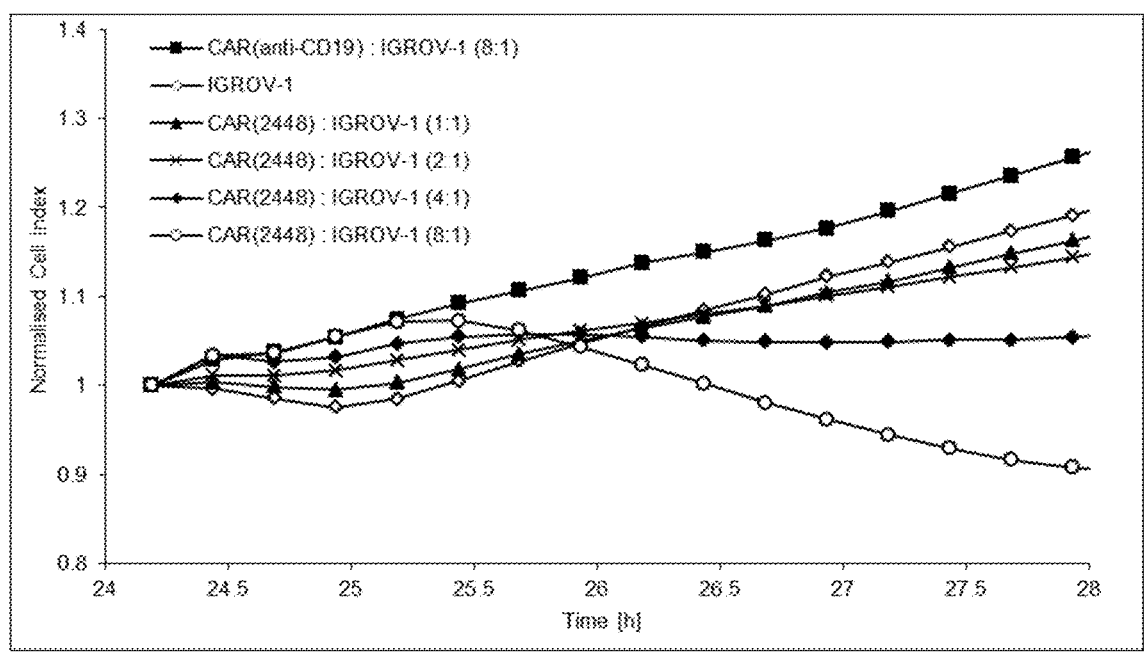
FIG. 31. Growth inhibition of CAR(2448). CAR(2448) T cells mediates growth inhibition of target cells. Target IGROV-1 cells were co-incubated with CAR-T cells at varying E:T ratios, and cell growth of adherent IGROV-1 cells was monitored via electrical impedance on the xCELLigence system. The results suggest that CAR(2448) T cells are capable of inhibiting the growth of target IGROV-1 cell in a dose-dependent, time-dependent manner, with the greatest rate of growth inhibition mediated by the highest CAR (2448) T cell dose. All dose levels of CAR(2448) T cells show inhibition of target cell growth compared to a non-target specific CAR control.

Target IGROV-1 cells were co-incubated with CAR-T cells. All dose levels of CAR(2448) T cells showed inhibition of target cell growth compared to a non-target specific CAR control (FIG. 31).

CAR(2448) T cells mediated their cytotoxic effect on IGROV1 target cells over the course of several hours.

What is claimed is:

1. A method of treating cancer in a subject in need thereof, comprising administering to the subject a therapeutically effective amount of an antigen-binding protein or an antigen-binding fragment thereof, or a composition comprising a physiologically acceptable carrier and a therapeutically effective amount of an antigen-binding protein or an antigen-binding fragment thereof, wherein said antigen-binding protein or antigen-binding fragment thereof binds to an N-linked glycan on annexin A2 (ANXA2), wherein said antigen-binding protein or antigen-binding fragment thereof comprises:
   a) (i) a heavy chain variable domain comprising a VHCDR1 having the amino acid sequence GYSITSGYSWH (SEQ ID NO: 9); a VHCDR2 having the amino acid sequence YIHYSGSTKYNPSLKS (SEQ ID NO: 10) and a VHCDR3 having the amino acid sequence GSNYGFDY (SEQ ID NO: 11); and (ii) a light chain variable domain comprising a VLCDR1 having the amino acid sequence KSSQSLLYSNDQKNYLA (SEQ ID NO: 12), a VLCDR2 having the amino acid sequence WASIRES (SEQ ID NO: 13), and a VLCDR3 having the amino acid sequence QQYYIYPLT (SEQ ID NO: 14), or
   b) (i) a heavy chain variable domain comprising a VHCDR1 having the amino acid sequence VYSITSGYSWH (SEQ ID NO: 21); a VHCDR2 having the amino acid sequence YIHYSGSTKYNPSLKS (SEQ ID NO: 10), and a VHCDR3 having the amino acid sequence GTDNAVDY (SEQ ID NO: 22); and (ii) a light chain variable domain comprising a VLCDR1 having the amino acid sequence KSSQSLLYSSNQKNYLA (SEQ ID NO: 23), a VLCDR2 having the amino acid sequence WASSRES (SEQ ID NO: 24), and a VLCDR3 having the amino acid sequence QQYYIYPLT (SEQ ID NO: 14), or
   c) (i) a heavy chain variable domain comprising a VHCDR1 having an amino acid sequence encoded by the nucleic acid sequence GCTACTCCATCACCAGTGGTTATAGCTGGCAC (SEQ ID NO: 15); a VHCDR2 having an amino acid sequence encoded by the nucleic acid sequence ACATACACTACAGTGGTAGCACTAAGTACAACCCATCTCTCAAAAGTC (SEQ ID NO: 16), and a VHCDR3 having an amino acid sequence encoded by the nucleic acid sequence GGAGTAACTACGGATTTGACTACT (SEQ ID NO: 17); and (ii) a light chain variable domain comprising a VLCDR1 having an amino acid sequence encoded by the nucleic acid sequence AGTCCAGTCAGAGCCTTTTATATAGTAACGATCAAAAGAACTACTTGGCCT (SEQ ID NO: 18), a VLCDR2 having an amino acid sequence encoded by the nucleic acid sequence GGGCATCTATTAGGGAATCTG (SEQ ID NO: 19), and a VLCDR3 having an amino acid sequence encoded by the nucleic acid sequence AGCAATATTATATCTATCCTCTCACGT (SEQ ID NO: 20), or
   d) (i) a heavy chain variable domain comprising a VHCDR1 having an amino acid sequence encoded by the nucleic acid sequence TCTACTCCATCACCAGTGGTTATAGCTGGCACT (SEQ ID NO: 25); a VHCDR2 having an amino acid sequence encoded by the nucleic acid sequence ACATACACTACAGTGGTAGTACTAAGTACAACCCATCTCTCAAAAGTC (SEQ ID NO: 26), and a VHCDR3 having an amino acid sequence encoded by the nucleic acid sequence GGACCGACAATGCTGTGGACTACT (SEQ ID NO: 27); and (ii) a light chain variable domain comprising a VLCDR1 having an amino acid sequence encoded by the nucleic acid sequence AGTCCAGTCAGAGCCTTTTATATAGTAGCAAT- CAAAAGAACTACTTGGCC T (SEQ ID NO: 28), a VLCDR2 having an amino acid sequence encoded by the nucleic acid sequence GGGCATCCAGTAGG-GAATCTG (SEQ ID NO: 29), and a VLCDR3 having an amino acid sequence encoded by the nucleic acid sequence AGCAATATTATATCTATCCTCTCACGT (SEQ ID NO: 20).

2. The method as claimed in claim 1, wherein the N-linked glycan is located at amino acid residue 62 of ANXA2.

3. The method as claimed in claim 1, wherein the heavy chain variable domain of (a) comprises the amino acid sequence set forth in SEQ ID NO:1, or wherein the heavy chain variable domain of (b) comprises the amino acid sequence set forth in SEQ ID NO:5.

4. The method as claimed in claim 1, wherein the light chain variable domain of (a) comprises the amino acid sequence set forth in SEQ ID NO:2, or wherein the light chain variable domain of (b) comprises the amino acid sequence set forth in SEQ ID NO: 6.

5. The method as claimed in claim 1, wherein the heavy chain variable domain of (c) is encoded by the nucleic acid sequence set forth in SEQ ID NO:3, or wherein the heavy chain variable domain of (d) is encoded by the nucleic acid sequence set forth in SEQ ID NO:7.

6. The method as claimed in claim 2, wherein the light chain variable domain of (c) is encoded by the nucleic acid sequence set forth in SEQ ID NO:4, or wherein the light chain variable domain of (d) is encoded by the nucleic acid sequence set forth in SEQ ID NO: 8.

7. The method as claimed in claim 1, wherein the antigen binding protein is selected from the group consisting of monoclonal, recombinant, polyclonal, chimeric, humanised, bispecific and heteroconjugate antibodies; a chimeric antigen receptor (CAR), a single variable domain, a domain antibody, antigen binding fragments, immunologically effective fragments, single chain Fv, a single chain antibody, a univalent antibody lacking a hinge region, a minibody and diabodies; optionally wherein the binding protein is a monoclonal antibody; optionally wherein the monoclonal antibody is 2448 or C51; optionally wherein the monoclonal antibody is humanized; optionally wherein the monoclonal antibody is chimeric; optionally wherein the monoclonal antibody is defucosylated; optionally wherein the degree of fucosylation is less than 10%, preferably less than 5%, and more preferably is less than 1.5% relative to the wild-type antibody.

8. The method as claimed in claim 1, wherein the antigen-binding protein, or antigen-binding fragment thereof further comprises a radioisotope or a cytotoxin conjugated thereto; optionally wherein the antibody is conjugated with a cytotoxin selected from the group consisting of monomethyl auristatin E (MMAE-1), mertansine (DM-1) and saporin; optionally wherein the antigen-binding protein, or an antigen-binding fragment is internalized into a cell upon binding to ANXA2; optionally wherein the antigen-binding protein, or an antigen-binding fragment thereof has a cytotoxic activity selected from one or more of the group consisting of complement dependent cytotoxic (CDC) activity, antibody dependent cellular cytotoxic (ADCC) activity and oncolytic activity.

9. The method as claimed in claim 1, wherein the composition comprises a further active pharmaceutical ingredient selected from the group consisting of bevacizumab, carboplatin, paclitaxel or gefitinib.

10. The method as claimed in claim 1, comprising administering the antigen-binding protein or antigen-binding fragment thereof or composition with a further active pharmaceutical ingredient or with chemotherapy.

11. The method as claimed in claim 10, comprising administering the further pharmaceutical agent or chemotherapy separately, simultaneously or sequentially.

12. The method as claimed in claim 1, wherein the cancer is selected from the group consisting of breast cancer, ovarian cancer and teratoma.

13. A method for detecting cancer in a subject or identifying a subject susceptible to cancer, comprising:
obtaining a sample from the subject
contacting the sample with an antigen-binding protein, or an antigen-binding fragment thereof, wherein said antigen-binding protein or antigen-binding fragment thereof binds to an N-linked glycan on annexin A2 (ANXA2);
detecting the binding of the antigen-binding protein or antigen-binding fragment thereof in the sample;
correlating the binding with a level of binding in a control sample to determine the level of binding in the sample, wherein an increase in the level of binding in the sample relative to the control sample is indicative of cancer or identifies a subject susceptible to cancer,
wherein said antigen-binding protein or antigen-binding fragment thereof comprises:
a) (i) a heavy chain variable domain comprising a VHCDR1 having the amino acid sequence GYSITSGYSWH (SEQ ID NO: 9); a VHCDR2 having the amino acid sequence YIHYSGSTKYNPSLKS (SEQ ID NO: 10) and a VHCDR3 having the amino acid sequence GSNYGFDY (SEQ ID NO: 11); and (ii) a light chain variable domain comprising a VLCDR1 having the amino acid sequence KSSQSLLYSNDQK-NYLA (SEQ ID NO: 12), a VLCDR2 having the amino acid sequence WASIRES (SEQ ID NO: 13), and a VLCDR3 having the amino acid sequence QQYYIY-PLT (SEQ ID NO: 14), or
b) (i) a heavy chain variable domain comprising a VHCDR1 having the amino acid sequence VYSITSGYSWH (SEQ ID NO: 21); a VHCDR2 having the amino acid sequence YIHYSGSTKYNPSLKS (SEQ ID NO: 10), and a VHCDR3 having the amino acid sequence GTDNAVDY (SEQ ID NO: 22); and (ii) a light chain variable domain comprising a VLCDR1 having the amino acid sequence KSSQSLLYSSNQK-NYLA (SEQ ID NO: 23), a VLCDR2 having the amino acid sequence WASSRES (SEQ ID NO: 24), and a VLCDR3 having the amino acid sequence QQYYIY-PLT (SEQ ID NO: 14), or
c) (i) a heavy chain variable domain comprising a VHCDR1 having an amino acid sequence encoded by the nucleic acid sequence GCTACTCCAT-CACCAGTGGTTATAGCTGGCAC (SEQ ID NO: 15); a VHCDR2 having an amino acid sequence encoded by the nucleic acid sequence ACATACACTA-CAGTGGTAGCACTAAGTACAACCCATCTCT-CAAAAGTC (SEQ ID NO: 16), and a VHCDR3 having an amino acid sequence encoded by the nucleic acid sequence GGAGTAACTACGGATTTGACTACT (SEQ ID NO: 17); and (ii) a light chain variable domain comprising a VLCDR1 having an amino acid sequence encoded by the nucleic acid sequence AGTCCAGTCAGAGCCTTTTATATAGTAACGAT-CAAAAGAACTACTTGGCCT (SEQ ID NO: 18), a VLCDR2 having an amino acid sequence encoded by the nucleic acid sequence GGGCATCTATTAGG-GAATCTG (SEQ ID NO: 19), and a VLCDR3 having an amino acid sequence encoded by the nucleic acid sequence AGCAATATTATATCTATCCTCTCACGT (SEQ ID NO: 20), or d) (i) a heavy chain variable domain comprising a VHCDR1 having an amino acid sequence encoded by the nucleic acid sequence TCTACTCCATCACCAGTGGTTATAGCTGGCACT (SEQ ID NO: 25); a VHCDR2 having an amino acid sequence encoded by the nucleic acid sequence ACATACACTACAGTGGTAGTACTAAGTACAACCCATCTCTCAAAAGTC (SEQ ID NO: 26), and a VHCDR3 having an amino acid sequence encoded by the nucleic acid sequence GGACCGACAATGCTGTGGACTACT (SEQ ID NO: 27); and (ii) a light chain variable domain comprising a VLCDR1 having an amino acid sequence encoded by the nucleic acid sequence AGTCCAGTCAGAGCCTTTTATATAGTAGCAATCAAAAGAACTACTTGGCC T (SEQ ID NO: 28), a VLCDR2 having an amino acid sequence encoded by the nucleic acid sequence GGGCATCCAGTAGGGAATCTG (SEQ ID NO: 29), and a VLCDR3 having an amino acid sequence encoded by the nucleic acid sequence AGCAATATTATATCTATCCTCTCACGT (SEQ ID NO: 20).

14. The method as claimed in claim 13, wherein the N-linked glycan is located at amino acid residue 62 of ANXA2.

15. The method as claimed in claim 13, wherein the control sample is from the same subject or from a different subject.

16. The method as claimed in claim 13, wherein the antigen-binding protein, or antigen-binding fragment thereof, comprises a detectable label.

17. The method as claimed in claim 13, wherein the cancer is selected from the group consisting of breast cancer, liver cancer, kidney cancer, colorectal cancer, ovarian cancer and teratoma.

* * * * *